US012263326B2

(12) United States Patent
Uber, III et al.

(10) Patent No.: US 12,263,326 B2
(45) Date of Patent: Apr. 1, 2025

(54) METHODS AND SYSTEMS FOR VERIFYING THE CONTENTS OF A SYRINGE USED FOR MEDICAL FLUID DELIVERY

(71) Applicant: BAYER HEALTHCARE LLC, Whippany, NJ (US)

(72) Inventors: Arthur Uber, III, Pittsburgh, PA (US); Michael Spohn, Fenelton, PA (US); David Griffiths, Pittsburgh, PA (US); Ralph Schriver, Tarentum, PA (US)

(73) Assignee: BAYER HEALTHCARE LLC, Whippany, NJ (US)

(*) Notice: Subject to any disclaimer, the term of this patent is extended or adjusted under 35 U.S.C. 154(b) by 1128 days.

(21) Appl. No.: 16/349,314

(22) PCT Filed: Nov. 13, 2017

(86) PCT No.: PCT/US2017/061268
§ 371 (c)(1),
(2) Date: May 13, 2019

(87) PCT Pub. No.: WO2018/089882
PCT Pub. Date: May 17, 2018

(65) Prior Publication Data
US 2020/0230317 A1  Jul. 23, 2020

Related U.S. Application Data

(60) Provisional application No. 62/421,661, filed on Nov. 14, 2016.

(51) Int. Cl.
*A61M 5/168* (2006.01)
*A61M 5/00* (2006.01)
*G16H 20/17* (2018.01)

(52) U.S. Cl.
CPC ........ *A61M 5/16854* (2013.01); *A61M 5/007* (2013.01); *G16H 20/17* (2018.01);
(Continued)

(58) Field of Classification Search
CPC .............. A61M 5/16854; A61M 5/007; A61M 2205/18; A61M 2205/332;
(Continued)

(56) References Cited

U.S. PATENT DOCUMENTS

| 383,858 A | 6/1888 | Campbell |
| 508,584 A | 11/1893 | Stevens |

(Continued)

FOREIGN PATENT DOCUMENTS

| CA | 2045070 A1 | 2/1992 |
| CA | 2077712 A1 | 12/1993 |

(Continued)

OTHER PUBLICATIONS

Angelini, P., "Use of mechanical injectors during percutaneous transluminal coronary angioplasty (PTCA)," Catheterization and Cardiovascular Diagnosis, vol. 16, Issue 3, pp. 193-194, Mar. 1989.

(Continued)

*Primary Examiner* — James D Ponton
*Assistant Examiner* — Hong-Van N Trinh
(74) *Attorney, Agent, or Firm* — Joseph L. Kent; James R. Stevenson

(57) ABSTRACT

A fluid delivery system and method for determining whether the correct fluid is being drawn into and/or dispensed from a syringe. The system includes a syringe, a fluid injector for drawing fluid into and dispensing fluid from the syringe, one or more sensors adapted to measure a force required to draw the fluid into and/or dispense the fluid from the syringe, a processor in communication with the one or more sensors, and a non-transitory, computer-readable storage medium in (Continued)

operable communication with the processor. The computer-readable storage medium contains one or more programming instructions that, when executed, cause the processor to receive from the one or more sensors one or more measurements of the force required to draw the fluid into and/or dispense the fluid from the syringe and determine from the one or more measurements whether a correct fluid is being drawn into and/or dispensed from the syringe.

9 Claims, 31 Drawing Sheets

(52) U.S. Cl.
CPC ... *A61M 2205/18* (2013.01); *A61M 2205/332* (2013.01); *A61M 2205/52* (2013.01)

(58) Field of Classification Search
CPC .. A61M 2205/52; A61M 5/14546; A61J 1/20; G16H 20/10; G16H 20/13; G16H 20/17
See application file for complete search history.

(56) References Cited

U.S. PATENT DOCUMENTS

| | | | |
|---|---|---|---|
| 945,143 A | 1/1910 | Iacques |
| 1,020,166 A | 3/1912 | Tibbott |
| 2,511,291 A | 6/1950 | Mueller |
| 2,583,206 A | 1/1952 | Borck et al. |
| 3,156,236 A | 11/1964 | Williamson |
| 3,159,312 A | 12/1964 | Van Sciver, II |
| 3,276,472 A | 10/1966 | Jinkens et al. |
| 3,349,713 A | 10/1967 | Fassbender |
| 3,520,295 A | 7/1970 | Kelly |
| 3,523,523 A | 8/1970 | Heinrich et al. |
| 3,623,474 A | 11/1971 | Heilman et al. |
| 3,635,444 A | 1/1972 | Potter |
| 3,671,208 A | 6/1972 | Medsker |
| 3,701,345 A | 10/1972 | Heilman |
| 3,719,207 A | 3/1973 | Takeda |
| 3,755,655 A | 8/1973 | Senecal |
| 3,769,976 A | 11/1973 | Victory |
| 3,793,600 A | 2/1974 | Grosbard |
| 3,812,843 A | 5/1974 | Wootten et al. |
| 3,817,843 A | 6/1974 | Barrett |
| 3,839,708 A | 10/1974 | Lyons et al. |
| 3,868,967 A | 3/1975 | Harding |
| 3,888,239 A | 6/1975 | Rubinstein |
| 3,895,220 A | 7/1975 | Nelson et al. |
| 3,898,983 A | 8/1975 | Elam |
| 3,927,955 A | 12/1975 | Spinosa et al. |
| 3,941,126 A | 3/1976 | Dietrich et al. |
| 3,958,103 A | 5/1976 | Oka et al. |
| 3,968,195 A | 7/1976 | Bishop |
| 3,995,381 A | 12/1976 | Manfred et al. |
| 4,001,549 A | 1/1977 | Corwin |
| 4,006,736 A | 2/1977 | Kranys et al. |
| 4,038,981 A | 8/1977 | LeFevre et al. |
| 4,044,757 A | 8/1977 | McWhorter et al. |
| 4,090,502 A | 5/1978 | Tajika |
| 4,135,247 A | 1/1979 | Gordon et al. |
| 4,151,845 A | 5/1979 | Clemens |
| 4,187,057 A | 2/1980 | Xanthopoulos |
| 4,191,183 A | 3/1980 | Mendelson |
| 4,199,000 A | 4/1980 | Edstrom |
| 4,204,775 A | 5/1980 | Speer |
| 4,207,871 A | 6/1980 | Jenkins |
| 4,208,136 A | 6/1980 | King et al. |
| 4,223,675 A | 9/1980 | Williams |
| 4,262,824 A | 4/1981 | Hrynewycz |
| 4,263,916 A | 4/1981 | Brooks et al. |
| 4,280,494 A | 7/1981 | Cosgrove, Jr. et al. |
| 4,284,073 A | 8/1981 | Krause et al. |
| 4,315,247 A | 2/1982 | Germanton |
| 4,319,568 A | 3/1982 | Tregoning |
| 4,329,067 A | 5/1982 | Goudy, Jr. |
| 4,340,153 A | 7/1982 | Spivey |
| 4,341,153 A | 7/1982 | Bowser |
| 4,392,847 A | 7/1983 | Whitney et al. |
| 4,392,849 A | 7/1983 | Petre et al. |
| 4,396,385 A | 8/1983 | Kelly et al. |
| 4,402,310 A | 9/1983 | Kimura |
| 4,409,966 A | 10/1983 | Lambrecht et al. |
| 4,434,820 A | 3/1984 | Glass |
| 4,434,822 A | 3/1984 | Bellamy et al. |
| 4,441,823 A | 4/1984 | Power et al. |
| 4,444,198 A | 4/1984 | Petre |
| 4,447,230 A | 5/1984 | Gula et al. |
| 4,448,200 A | 5/1984 | Brooks et al. |
| 4,474,476 A | 10/1984 | Thomsen |
| 4,477,923 A | 10/1984 | Baumann et al. |
| 4,479,760 A | 10/1984 | Bilstad et al. |
| 4,479,761 A | 10/1984 | Bilstad et al. |
| 4,479,762 A | 10/1984 | Bilstad et al. |
| 4,504,908 A | 3/1985 | Riederer et al. |
| 4,509,526 A | 4/1985 | Barnes et al. |
| 4,512,764 A | 4/1985 | Wunsch |
| 4,542,459 A | 9/1985 | Riederer |
| 4,544,949 A | 10/1985 | Kurihara |
| 4,551,133 A | 11/1985 | Zegers de Beyl et al. |
| 4,552,130 A | 11/1985 | Kinoshita |
| 4,559,036 A | 12/1985 | Wunsch |
| 4,563,175 A | 1/1986 | LaFond |
| 4,578,802 A | 3/1986 | Itoh |
| 4,585,009 A | 4/1986 | Barker et al. |
| 4,585,941 A | 4/1986 | Bergner |
| 4,610,670 A | 9/1986 | Spencer |
| 4,610,790 A | 9/1986 | Reti et al. |
| 4,611,340 A | 9/1986 | Okazaki |
| 4,612,572 A | 9/1986 | Komatsu et al. |
| 4,625,494 A | 12/1986 | Iwatschenko et al. |
| 4,626,144 A | 12/1986 | Berner |
| 4,633,307 A | 12/1986 | Honda |
| 4,634,426 A | 1/1987 | Kamen |
| 4,636,144 A | 1/1987 | Abe et al. |
| 4,655,197 A | 4/1987 | Atkinson |
| 4,662,906 A | 5/1987 | Matkovich et al. |
| 4,672,651 A | 6/1987 | Horiba et al. |
| 4,676,776 A | 6/1987 | Howson |
| 4,682,170 A | 7/1987 | Kubota et al. |
| 4,689,670 A | 8/1987 | Okazaki |
| 4,710,166 A | 12/1987 | Thompson et al. |
| 4,723,261 A | 2/1988 | Janssen et al. |
| 4,750,643 A | 6/1988 | Wortrich |
| 4,754,786 A | 7/1988 | Roberts |
| 4,781,687 A | 11/1988 | Wall |
| 4,783,273 A | 11/1988 | Knutsson et al. |
| 4,789,014 A | 12/1988 | DiGianfilippo et al. |
| 4,793,357 A | 12/1988 | Lindstrom |
| 4,795,429 A | 1/1989 | Feldstein |
| 4,798,590 A | 1/1989 | O'Leary et al. |
| 4,804,454 A | 2/1989 | Asakura et al. |
| 4,823,833 A | 4/1989 | Hogan et al. |
| 4,835,521 A | 5/1989 | Andrejasich et al. |
| 4,836,187 A | 6/1989 | Iwakoshi et al. |
| 4,838,856 A | 6/1989 | Mulreany et al. |
| 4,840,620 A | 6/1989 | Kobayashi et al. |
| 4,844,052 A | 7/1989 | Iwakoshi et al. |
| 4,853,521 A | 8/1989 | Claeys et al. |
| 4,854,301 A | 8/1989 | Nakajima |
| 4,854,324 A | 8/1989 | Hirschman et al. |
| 4,857,056 A | 8/1989 | Talonn |
| 4,874,359 A | 10/1989 | White et al. |
| 4,879,880 A | 11/1989 | Harrison |
| 4,880,014 A | 11/1989 | Zarowitz et al. |
| 4,887,208 A | 12/1989 | Schneider et al. |
| 4,887,554 A | 12/1989 | Whitford |
| 4,901,731 A | 2/1990 | Millar |
| 4,903,705 A | 2/1990 | Imamura et al. |
| 1,913,154 A | 4/1990 | Ermert et al. |
| 4,922,916 A | 5/1990 | Ermert et al. |
| 4,925,444 A | 5/1990 | Orkin et al. |
| 4,929,818 A | 5/1990 | Bradbury et al. |

(56) References Cited

U.S. PATENT DOCUMENTS

| | | |
|---|---|---|
| 4,935,005 A | 6/1990 | Haines |
| 4,936,832 A | 6/1990 | Vaillancourt |
| 4,943,279 A | 7/1990 | Samiotes et al. |
| 4,943,779 A | 7/1990 | Pedersen et al. |
| 4,943,987 A | 7/1990 | Asahina et al. |
| 4,946,256 A | 8/1990 | Woodruff |
| 4,946,439 A | 8/1990 | Eggers |
| 4,947,412 A | 8/1990 | Mattson |
| 4,950,245 A | 8/1990 | Brown et al. |
| 4,952,068 A | 8/1990 | Flint |
| 4,954,129 A | 9/1990 | Giuliani et al. |
| 4,965,726 A | 10/1990 | Heuscher et al. |
| 4,966,579 A | 10/1990 | Polaschegg |
| 4,976,687 A | 12/1990 | Martin |
| 4,978,335 A | 12/1990 | Arthur, III |
| 4,981,467 A | 1/1991 | Bobo, Jr. et al. |
| 4,995,064 A | 2/1991 | Wilson et al. |
| 5,002,055 A | 3/1991 | Merki et al. |
| 5,004,472 A | 4/1991 | Wallace et al. |
| 5,009,654 A | 4/1991 | Minshall et al. |
| 5,010,473 A | 4/1991 | Jacobs |
| 5,013,173 A | 5/1991 | Shiraishi |
| 5,018,173 A | 5/1991 | Komai et al. |
| 5,032,112 A | 7/1991 | Fairchild et al. |
| 5,034,987 A | 7/1991 | Fujimoto et al. |
| 5,040,537 A | 8/1991 | Katakura |
| 5,053,002 A | 10/1991 | Barlow |
| 5,054,044 A | 10/1991 | Audon et al. |
| 5,056,568 A | 10/1991 | DiGianfilippo et al. |
| 5,059,171 A | 10/1991 | Bridge et al. |
| 5,059,173 A | 10/1991 | Sacco |
| 5,061,243 A | 10/1991 | Winchell et al. |
| 5,069,662 A | 12/1991 | Bodden |
| 5,078,683 A | 1/1992 | Sancoff et al. |
| 5,088,981 A | 2/1992 | Howson et al. |
| 5,100,380 A | 3/1992 | Epstein et al. |
| 5,104,374 A | 4/1992 | Bishko et al. |
| 5,104,387 A | 4/1992 | Pokorney et al. |
| 5,108,365 A | 4/1992 | Woods, Jr. |
| 5,111,492 A | 5/1992 | Klausz |
| 5,113,905 A | 5/1992 | Pruitt et al. |
| 5,123,056 A | 6/1992 | Wilson |
| 5,123,121 A | 6/1992 | Broersma |
| 5,125,018 A | 6/1992 | Asahina |
| 5,128,121 A | 7/1992 | Berg et al. |
| 5,133,336 A | 7/1992 | Savitt et al. |
| 5,135,000 A | 8/1992 | Akselrod et al. |
| 5,140,862 A | 8/1992 | Pappalardo |
| 5,150,292 A | 9/1992 | Hoffmann et al. |
| 5,166,961 A | 11/1992 | Brunnett et al. |
| 5,180,895 A | 1/1993 | Briggs et al. |
| 5,180,896 A | 1/1993 | Gibby et al. |
| 5,190,744 A | 3/1993 | Rocklage et al. |
| 5,191,878 A | 3/1993 | Iida et al. |
| 5,196,007 A | 3/1993 | Ellman et al. |
| 5,199,604 A | 4/1993 | Palmer et al. |
| 5,207,642 A | 5/1993 | Orkin et al. |
| 5,215,095 A | 6/1993 | Macvicar et al. |
| 5,228,070 A | 7/1993 | Mattson |
| 5,230,614 A | 7/1993 | Zanger et al. |
| 5,242,390 A | 9/1993 | Goldrath |
| 5,249,122 A | 9/1993 | Stritzke |
| 5,249,579 A | 10/1993 | Hobbs et al. |
| 5,262,946 A | 11/1993 | Heuscher |
| 5,267,174 A | 11/1993 | Kaufman et al. |
| 5,269,756 A | 12/1993 | Dryden |
| 5,273,537 A | 12/1993 | Haskvitz et al. |
| 5,274,218 A | 12/1993 | Urata et al. |
| 5,276,614 A | 1/1994 | Heuscher |
| 5,286,252 A | 2/1994 | Tuttle et al. |
| 5,287,273 A | 2/1994 | Kupfer et al. |
| 5,295,967 A | 3/1994 | Rondelet et al. |
| 5,300,031 A | 4/1994 | Neer et al. |
| 5,301,656 A | 4/1994 | Negoro et al. |
| 5,301,672 A | 4/1994 | Kalender |
| 5,304,126 A | 4/1994 | Epstein et al. |
| 5,310,997 A | 5/1994 | Roach et al. |
| 5,311,568 A | 5/1994 | McKee, Jr. et al. |
| 5,313,992 A | 5/1994 | Grabenkort |
| 5,317,506 A | 5/1994 | Coutre et al. |
| 5,328,463 A | 7/1994 | Barton et al. |
| 5,329,459 A | 7/1994 | Kaufman et al. |
| 5,334,141 A | 8/1994 | Carr et al. |
| 5,339,799 A | 8/1994 | Kami et al. |
| 5,349,625 A | 9/1994 | Born et al. |
| 5,349,635 A | 9/1994 | Scott |
| 5,352,979 A | 10/1994 | Conturo |
| 5,354,273 A | 10/1994 | Hagen |
| 5,361,761 A | 11/1994 | Van Lysel et al. |
| 5,362,948 A | 11/1994 | Morimoto |
| 5,368,562 A | 11/1994 | Blomquist et al. |
| 5,368,567 A | 11/1994 | Lee |
| 5,368,570 A | 11/1994 | Thompson et al. |
| 5,373,231 A | 12/1994 | Boll et al. |
| 5,376,070 A | 12/1994 | Purvis et al. |
| 5,378,231 A | 1/1995 | Johnson et al. |
| 5,382,232 A | 1/1995 | Hague et al. |
| 5,383,231 A | 1/1995 | Yamagishi |
| 5,383,858 A | 1/1995 | Reilly et al. |
| 5,385,540 A | 1/1995 | Abbott et al. |
| 5,388,139 A | 2/1995 | Beland |
| 5,392,849 A | 2/1995 | Matsunaga et al. |
| 5,400,792 A | 3/1995 | Hoebel et al. |
| 5,417,213 A | 5/1995 | Prince |
| 5,431,627 A | 7/1995 | Pastrone et al. |
| 5,433,704 A | 7/1995 | Ross et al. |
| 5,445,621 A | 8/1995 | Poli et al. |
| 5,450,847 A | 9/1995 | Kaempfe et al. |
| 5,453,639 A | 9/1995 | Cronin et al. |
| 5,456,255 A | 10/1995 | Abe et al. |
| 5,458,128 A | 10/1995 | Polanyi et al. |
| 5,459,769 A | 10/1995 | Brown |
| 5,460,609 A | 10/1995 | O'Donnell |
| 5,464,391 A | 11/1995 | DeVale |
| 5,468,240 A | 11/1995 | Gentelia et al. |
| 5,469,769 A | 11/1995 | Sawada et al. |
| 5,469,849 A | 11/1995 | Sasaki et al. |
| 5,472,403 A | 12/1995 | Cornacchia et al. |
| 5,474,683 A | 12/1995 | Bryant et al. |
| 5,485,831 A | 1/1996 | Holdsworth et al. |
| 5,489,265 A | 2/1996 | Montalvo et al. |
| 5,494,036 A | 2/1996 | Uber, III et al. |
| 5,494,822 A | 2/1996 | Sadri |
| 5,496,273 A | 3/1996 | Pastrone et al. |
| 5,507,412 A | 4/1996 | Ebert et al. |
| 5,515,851 A | 5/1996 | Goldstein |
| 5,522,798 A | 6/1996 | Johnson et al. |
| 5,531,679 A | 7/1996 | Schulman et al. |
| 5,531,697 A | 7/1996 | Olsen et al. |
| 5,533,978 A | 7/1996 | Teirstein |
| 5,544,215 A | 8/1996 | Shroy, Jr. et al. |
| 5,547,470 A | 8/1996 | Johnson et al. |
| 5,552,130 A | 9/1996 | Kraus et al. |
| 5,553,619 A | 9/1996 | Prince |
| 5,560,317 A | 10/1996 | Bunyan et al. |
| 5,566,092 A | 10/1996 | Wang et al. |
| 5,569,181 A | 10/1996 | Heilman et al. |
| 5,569,208 A | 10/1996 | Woelpper et al. |
| 5,573,515 A | 11/1996 | Wilson et al. |
| 5,579,767 A | 12/1996 | Prince |
| 5,583,902 A | 12/1996 | Bae |
| 5,590,654 A | 1/1997 | Prince |
| 5,592,940 A | 1/1997 | Kampfe et al. |
| 5,601,086 A | 2/1997 | Pretlow, III et al. |
| 5,611,344 A | 3/1997 | Bernstein et al. |
| 5,616,124 A | 4/1997 | Hague et al. |
| 5,681,285 A | 10/1997 | Ford et al. |
| 5,687,208 A | 11/1997 | Bae et al. |
| 5,687,708 A | 11/1997 | Farnsworth et al. |
| 5,713,358 A | 2/1998 | Mistretta et al. |
| 5,724,976 A | 3/1998 | Mine et al. |
| 5,725,500 A | 3/1998 | Micheler |
| 5,739,508 A | 4/1998 | Uber, III |
| 5,743,266 A | 4/1998 | Levene et al. |

(56) References Cited

U.S. PATENT DOCUMENTS

| | | |
|---|---|---|
| 5,768,405 A | 6/1998 | Makram-Ebeid |
| 5,796,862 A | 8/1998 | Pawlicki et al. |
| 5,799,649 A | 9/1998 | Prince |
| 5,800,397 A | 9/1998 | Wilson et al. |
| 5,806,519 A | 9/1998 | Evans, III et al. |
| 5,808,203 A | 9/1998 | Nolan, Jr. et al. |
| 5,827,219 A | 10/1998 | Uber, III et al. |
| 5,827,504 A | 10/1998 | Yan et al. |
| 5,840,026 A | 11/1998 | Uber, III et al. |
| 5,843,037 A | 12/1998 | Uber, III |
| 5,846,517 A | 12/1998 | Unger |
| 5,865,744 A | 2/1999 | Lemelson |
| 5,873,861 A | 2/1999 | Hitchins et al. |
| 5,881,124 A | 3/1999 | Giger et al. |
| 5,882,343 A | 3/1999 | Wilson et al. |
| 5,902,054 A | 5/1999 | Coudray |
| 5,903,454 A | 5/1999 | Hoffberg et al. |
| 5,916,165 A | 6/1999 | Duchon et al. |
| 5,920,054 A | 7/1999 | Uber, III |
| 5,947,935 A | 9/1999 | Kazousky et al. |
| 5,987,347 A | 11/1999 | Khoury et al. |
| 5,988,587 A | 11/1999 | Duchon et al. |
| 6,046,225 A | 4/2000 | Maddock |
| 6,055,985 A | 5/2000 | Bae et al. |
| 6,056,902 A | 5/2000 | Hettinga |
| 6,063,052 A | 5/2000 | Uber, III et al. |
| 6,073,042 A | 6/2000 | Simonetti |
| 6,099,502 A | 8/2000 | Duchon et al. |
| 6,113,568 A | 9/2000 | Olaussen |
| 6,132,396 A | 10/2000 | Antanavich et al. |
| 6,149,627 A | 11/2000 | Uber, III |
| 6,186,146 B1 | 2/2001 | Glickman |
| 6,201,889 B1 | 3/2001 | Vannah |
| 6,221,045 B1 | 4/2001 | Duchon et al. |
| 6,236,706 B1 | 5/2001 | Hsieh |
| 6,248,093 B1 | 6/2001 | Moberg |
| 6,306,117 B1 | 10/2001 | Uber, III |
| 6,313,131 B1 | 11/2001 | Lawyer |
| 6,317,623 B1 | 11/2001 | Griffiths et al. |
| 6,322,535 B1 | 11/2001 | Hitchins et al. |
| 6,344,030 B1 | 2/2002 | Duchon et al. |
| 6,381,486 B1 | 4/2002 | Mistretta et al. |
| 6,387,098 B1 | 5/2002 | Cole et al. |
| 6,397,093 B1 | 5/2002 | Aldrich |
| 6,397,097 B1 | 5/2002 | Requardt |
| 6,402,697 B1 | 6/2002 | Calkins et al. |
| 6,423,719 B1 | 7/2002 | Lawyer |
| 6,442,418 B1 | 8/2002 | Evans, III et al. |
| 6,470,889 B1 | 10/2002 | Bae et al. |
| 6,471,674 B1 | 10/2002 | Emig et al. |
| 6,478,735 B1 | 11/2002 | Pope et al. |
| 6,503,226 B1 | 1/2003 | Martinell et al. |
| 6,520,930 B2 | 2/2003 | Critchlow et al. |
| 6,527,718 B1 | 3/2003 | Connor et al. |
| 6,554,819 B2 | 4/2003 | Reich |
| 6,556,695 B1 | 4/2003 | Packer et al. |
| 6,572,851 B2 | 6/2003 | Muramatsu et al. |
| 6,574,496 B1 | 6/2003 | Golman et al. |
| 6,575,930 B1 | 6/2003 | Trombley, III et al. |
| 6,597,938 B2 | 7/2003 | Liu |
| 6,626,862 B1 | 9/2003 | Duchon et al. |
| 6,635,030 B1 | 10/2003 | Bae et al. |
| 6,643,537 B1 | 11/2003 | Zatezalo et al. |
| 6,652,489 B2 | 11/2003 | Trocki et al. |
| 6,656,157 B1 | 12/2003 | Duchon et al. |
| 6,673,033 B1 | 1/2004 | Sciulli et al. |
| 6,685,733 B1 | 2/2004 | Dae et al. |
| 6,691,047 B1 | 2/2004 | Fredericks |
| 6,699,219 B2 | 3/2004 | Emig et al. |
| 6,731,971 B2 | 5/2004 | Evans et al. |
| 6,754,521 B2 | 6/2004 | Prince |
| 6,775,764 B1 | 8/2004 | Batcher |
| 6,776,764 B2 | 8/2004 | Pinsky |
| 6,866,653 B2 | 3/2005 | Bae |
| 6,876,720 B2 | 4/2005 | Tsuyuki |
| 6,879,853 B2 | 4/2005 | Meaney et al. |
| 6,983,590 B2 | 1/2006 | Roelle et al. |
| 7,094,216 B2 | 8/2006 | Trombley, III et al. |
| 7,267,666 B1 | 9/2007 | Duchon et al. |
| 7,267,667 B2 | 9/2007 | Houde et al. |
| 7,292,720 B2 | 11/2007 | Horger et al. |
| 7,351,221 B2 | 4/2008 | Trombley, III et al. |
| 7,553,294 B2 | 6/2009 | Lazzaro et al. |
| 7,553,295 B2 | 6/2009 | Susi |
| 7,556,619 B2 | 7/2009 | Spohn et al. |
| 7,563,249 B2 | 7/2009 | Schriver et al. |
| 7,666,169 B2 | 2/2010 | Cowan et al. |
| 7,688,057 B2 | 3/2010 | Foss et al. |
| 7,861,893 B2 | 1/2011 | Voegele et al. |
| 7,925,330 B2 | 4/2011 | Kalafut et al. |
| 8,007,487 B2 | 8/2011 | Patrick et al. |
| 8,147,464 B2 | 4/2012 | Spohn et al. |
| 8,162,903 B2 | 4/2012 | Reilly et al. |
| 8,295,914 B2 | 10/2012 | Kalafut et al. |
| 8,337,456 B2 | 12/2012 | Schriver et al. |
| 8,377,003 B2 | 2/2013 | Wagner |
| 8,403,909 B2 | 3/2013 | Spohn et al. |
| 8,439,863 B2 | 5/2013 | Fago et al. |
| 8,486,017 B2 | 7/2013 | Masuda et al. |
| 8,540,698 B2 | 9/2013 | Spohn et al. |
| 8,905,969 B2 | 12/2014 | Nystrom et al. |
| 9,101,708 B2 | 8/2015 | Small et al. |
| 9,173,995 B1 | 11/2015 | Tucker et al. |
| 9,199,033 B1 | 12/2015 | Cowan et al. |
| 9,238,099 B2 | 1/2016 | Kalafut et al. |
| 9,242,083 B2 | 1/2016 | Fago et al. |
| 9,259,527 B2 | 2/2016 | Spohn et al. |
| 9,314,749 B2 | 4/2016 | Yagi et al. |
| 9,333,293 B2 | 5/2016 | Williams, Jr. et al. |
| 9,474,857 B2 | 10/2016 | Riley et al. |
| 9,480,788 B2 | 11/2016 | Wagner |
| 9,480,791 B2 | 11/2016 | Reilly |
| 9,555,379 B2 | 1/2017 | Schriver et al. |
| 9,566,381 B2 | 2/2017 | Barron et al. |
| 9,861,752 B2 | 1/2018 | Buder et al. |
| 9,901,671 B2 | 2/2018 | Toews et al. |
| 9,987,413 B2 | 6/2018 | Seibold et al. |
| 10,041,483 B2 | 8/2018 | Chappel et al. |
| 10,112,008 B2 | 10/2018 | Neftel et al. |
| D847,985 S | 5/2019 | Neff et al. |
| 10,391,234 B2 | 8/2019 | Sams et al. |
| 10,420,902 B2 | 9/2019 | Cowan et al. |
| 10,549,084 B2 | 2/2020 | Sokolov et al. |
| 2001/0018937 A1 | 9/2001 | Nemoto |
| 2001/0027265 A1 | 10/2001 | Prince |
| 2001/0056233 A1 | 12/2001 | Uber et al. |
| 2002/0007116 A1 | 1/2002 | Zatezalo et al. |
| 2002/0010551 A1 | 1/2002 | Wang et al. |
| 2002/0026148 A1 | 2/2002 | Uber et al. |
| 2002/0099254 A1 | 7/2002 | Movahed |
| 2002/0123702 A1 | 9/2002 | Cho |
| 2002/0151854 A1 | 10/2002 | Duchon et al. |
| 2003/0050556 A1 | 3/2003 | Uber et al. |
| 2003/0120171 A1 | 6/2003 | Diamantopoulos et al. |
| 2003/0195462 A1 | 10/2003 | Mann et al. |
| 2003/0212364 A1 | 11/2003 | Mann et al. |
| 2003/0216683 A1 | 11/2003 | Shekalim |
| 2003/0226539 A1 | 12/2003 | Kim et al. |
| 2004/0011740 A1 | 1/2004 | Bernard et al. |
| 2004/0025452 A1 | 2/2004 | McLean |
| 2004/0044302 A1 | 3/2004 | Bernard et al. |
| 2004/0064041 A1 | 4/2004 | Lazzaro et al. |
| 2004/0092905 A1 | 5/2004 | Azzolini |
| 2004/0097806 A1 | 5/2004 | Hunter et al. |
| 2004/0154788 A1 | 8/2004 | Symonds |
| 2004/0162484 A1 | 8/2004 | Nemoto |
| 2004/0163655 A1 | 8/2004 | Gelfand et al. |
| 2004/0167415 A1 | 8/2004 | Gelfand et al. |
| 2004/0215144 A1 | 10/2004 | Duchon et al. |
| 2004/0253183 A1 | 12/2004 | Uber, III et al. |
| 2004/0254533 A1 | 12/2004 | Schriver et al. |
| 2005/0107697 A1 | 5/2005 | Berke et al. |
| 2005/0113754 A1 | 5/2005 | Cowan |
| 2005/0113766 A1 | 5/2005 | Mottola et al. |

(56) References Cited

U.S. PATENT DOCUMENTS

| | | |
|---|---|---|
| 2005/0171487 A1 | 8/2005 | Haury et al. |
| 2005/0234407 A1 | 10/2005 | Spohn et al. |
| 2005/0234428 A1 | 10/2005 | Spohn et al. |
| 2006/0052794 A1 | 3/2006 | McGill et al. |
| 2006/0079765 A1 | 4/2006 | Neer et al. |
| 2006/0079843 A1 | 4/2006 | Brooks et al. |
| 2006/0135940 A1 | 6/2006 | Joshi |
| 2006/0167415 A1 | 7/2006 | Nemoto |
| 2006/0276936 A1* | 12/2006 | Vanderveen ........... G16H 20/17 700/282 |
| 2007/0068964 A1 | 3/2007 | Tanaami et al. |
| 2007/0129705 A1 | 6/2007 | Trombley, III et al. |
| 2007/0161970 A1 | 7/2007 | Spohn et al. |
| 2007/0219496 A1 | 9/2007 | Kamen et al. |
| 2007/0276327 A1 | 11/2007 | Kalafut et al. |
| 2008/0015406 A1 | 1/2008 | Dlugos et al. |
| 2008/0045925 A1 | 2/2008 | Stepovich et al. |
| 2008/0086087 A1 | 4/2008 | Spohn et al. |
| 2008/0167621 A1 | 7/2008 | Wagner et al. |
| 2008/0183131 A1 | 7/2008 | Duchon et al. |
| 2009/0112164 A1 | 4/2009 | Reilly et al. |
| 2009/0216192 A1 | 8/2009 | Schriver et al. |
| 2009/0234226 A1 | 9/2009 | Nemoto |
| 2009/0247865 A1 | 10/2009 | Spohn et al. |
| 2009/0247961 A1 | 10/2009 | Carlyon |
| 2009/0312744 A1 | 12/2009 | Keeley et al. |
| 2010/0113887 A1 | 5/2010 | Kalafut et al. |
| 2010/0114064 A1 | 5/2010 | Kalafut et al. |
| 2010/0130809 A1 | 5/2010 | Morello |
| 2010/0222768 A1 | 9/2010 | Spohn et al. |
| 2010/0249586 A1 | 9/2010 | Cocker et al. |
| 2010/0262078 A1 | 10/2010 | Blomquist |
| 2010/0331779 A1 | 12/2010 | Nystrom et al. |
| 2011/0275988 A1 | 11/2011 | Davis et al. |
| 2012/0089114 A1 | 4/2012 | Hemond et al. |
| 2012/0101472 A1 | 4/2012 | Schroeder et al. |
| 2012/0123257 A1 | 5/2012 | Stokes, Jr. et al. |
| 2012/0178629 A1 | 7/2012 | Hudson et al. |
| 2012/0203177 A1 | 8/2012 | Lanier, Jr. et al. |
| 2012/0204997 A1 | 8/2012 | Winn et al. |
| 2012/0217231 A1 | 8/2012 | Moore et al. |
| 2012/0245560 A1 | 9/2012 | Hochman |
| 2013/0030290 A1 | 1/2013 | Nemoto |
| 2013/0245604 A1 | 9/2013 | Kouyoumjian et al. |
| 2013/0261993 A1* | 10/2013 | Ruchti ................ F04B 43/0081 702/50 |
| 2013/0274599 A1 | 10/2013 | Bouton et al. |
| 2014/0027009 A1 | 1/2014 | Riley et al. |
| 2014/0142537 A1 | 5/2014 | Gibson et al. |
| 2014/0276550 A1 | 9/2014 | Uram et al. |
| 2016/0030662 A1 | 2/2016 | Uber, III et al. |
| 2016/0114109 A1* | 4/2016 | Lavi .................. A61M 5/31596 604/82 |
| 2016/0278725 A1 | 9/2016 | Van Nijnatten |
| 2016/0346485 A1 | 12/2016 | Mohr et al. |
| 2017/0056603 A1 | 3/2017 | Cowan et al. |
| 2017/0136424 A1 | 5/2017 | Schriver et al. |
| 2017/0143898 A1 | 5/2017 | Grosse-Wentrup et al. |
| 2017/0196702 A1 | 7/2017 | Agarwal et al. |
| 2017/0258982 A1 | 9/2017 | Kemper |
| 2017/0290971 A1 | 10/2017 | Hedmann et al. |
| 2017/0343446 A1 | 11/2017 | Ciolkosz et al. |
| 2017/0361017 A1 | 12/2017 | Verma et al. |
| 2018/0015274 A1 | 1/2018 | Haury et al. |
| 2018/0133392 A1 | 5/2018 | Dembo et al. |
| 2018/0161496 A1 | 6/2018 | Berry et al. |
| 2019/0083699 A1 | 3/2019 | Spohn et al. |
| 2019/0201082 A1 | 7/2019 | Shelton, IV et al. |
| 2024/0131268 A1 | 4/2024 | Uber, III et al. |

FOREIGN PATENT DOCUMENTS

| | | |
|---|---|---|
| CA | 2234050 A1 | 4/1997 |
| CN | 1671428 A | 9/2005 |
| DE | 3726452 A1 | 2/1989 |
| DE | 4426387 A1 | 8/1995 |
| DE | 19702896 A1 | 7/1997 |
| DE | 19647701 A1 | 5/1998 |
| DE | 19919572 A1 | 11/2000 |
| EP | 0121216 A1 | 10/1984 |
| EP | 0129910 A1 | 1/1985 |
| EP | 0189491 A1 | 8/1986 |
| EP | 0192786 A2 | 9/1986 |
| EP | 0245160 A1 | 11/1987 |
| EP | 0319275 A1 | 6/1989 |
| EP | 0337924 A2 | 10/1989 |
| EP | 0343501 A2 | 11/1989 |
| EP | 0364966 A1 | 4/1990 |
| EP | 0365301 A1 | 4/1990 |
| EP | 0372152 A1 | 6/1990 |
| EP | 0378896 A2 | 7/1990 |
| EP | 0429191 A2 | 5/1991 |
| EP | 0471455 A2 | 2/1992 |
| EP | 0475563 A1 | 3/1992 |
| EP | 0595474 A2 | 5/1994 |
| EP | 0600448 A2 | 6/1994 |
| EP | 0619122 A1 | 10/1994 |
| EP | 0439711 B1 | 5/1995 |
| EP | 0869738 A1 | 10/1998 |
| EP | 1016427 A2 | 7/2000 |
| EP | 1769849 A1 | 4/2007 |
| EP | 1800704 A1 | 6/2007 |
| EP | 1870121 A1 | 12/2007 |
| EP | 2692375 A1 | 2/2014 |
| EP | 2990073 A1 | 3/2016 |
| EP | 1838365 B1 | 2/2019 |
| FR | 2493708 A1 | 5/1982 |
| FR | 2561949 A1 | 10/1985 |
| GB | 201800 A | 8/1923 |
| GB | 2252656 A | 8/1992 |
| GB | 2328745 A | 3/1999 |
| JP | S5017781 A | 2/1975 |
| JP | S5815842 A | 1/1983 |
| JP | S59214432 A | 12/1984 |
| JP | S60194934 A | 10/1985 |
| JP | S60194935 A | 10/1985 |
| JP | S60253197 A | 12/1985 |
| JP | S62216199 A | 9/1987 |
| JP | S6340538 A | 2/1988 |
| JP | S63290547 A | 11/1988 |
| JP | H01207038 A | 8/1989 |
| JP | H02224647 A | 9/1990 |
| JP | H02234747 A | 9/1990 |
| JP | H0355040 A | 3/1991 |
| JP | H04115677 A | 4/1992 |
| JP | H0584296 A | 4/1993 |
| JP | H07178169 A | 7/1995 |
| JP | H0849598 A | 2/1996 |
| JP | H10211198 A | 8/1998 |
| JP | 2000175900 A | 6/2000 |
| JP | 2003102724 A | 4/2003 |
| JP | 2003116843 A | 4/2003 |
| JP | 2003210456 A | 7/2003 |
| JP | 2003225234 A | 8/2003 |
| JP | 2004174008 A | 6/2004 |
| JP | 2004236849 A | 8/2004 |
| JP | 2004298550 A | 10/2004 |
| JP | 4960180 B2 | 6/2012 |
| JP | 5063593 B2 | 10/2012 |
| JP | 5203971 B2 | 6/2013 |
| JP | 5227791 B2 | 7/2013 |
| JP | 5485885 B2 | 5/2014 |
| JP | 5490840 B2 | 5/2014 |
| JP | 5511409 B2 | 6/2014 |
| JP | 5882595 B2 | 3/2016 |
| JP | 5897798 B2 | 3/2016 |
| WO | 8001754 A1 | 9/1980 |
| WO | 8500292 A1 | 1/1985 |
| WO | 8803815 A1 | 6/1988 |
| WO | 9114232 A1 | 9/1991 |
| WO | 9114233 A1 | 9/1991 |
| WO | 9315658 A1 | 8/1993 |
| WO | 9325141 A1 | 12/1993 |

(56) References Cited

FOREIGN PATENT DOCUMENTS

| | | |
|---|---|---|
| WO | 9415664 A1 | 7/1994 |
| WO | 9632975 A1 | 10/1996 |
| WO | 9712550 A1 | 4/1997 |
| WO | 9820919 A1 | 5/1998 |
| WO | 9924095 A2 | 5/1999 |
| WO | 0061216 A1 | 10/2000 |
| WO | 0141835 A2 | 6/2001 |
| WO | 03015633 A1 | 2/2003 |
| WO | 2004012787 A2 | 2/2004 |
| WO | 2004035116 A1 | 4/2004 |
| WO | 2004091688 A2 | 10/2004 |
| WO | 2005016165 A1 | 2/2005 |
| WO | 2005035995 A1 | 4/2005 |
| WO | 2006042093 A1 | 4/2006 |
| WO | 2006074415 A2 | 7/2006 |
| WO | 2007079016 A2 | 7/2007 |
| WO | 2007092618 A2 | 8/2007 |
| WO | 2007116840 A1 | 10/2007 |
| WO | 2007116862 A1 | 10/2007 |
| WO | 2007116891 A1 | 10/2007 |
| WO | 2007133942 A2 | 11/2007 |
| WO | 2008078604 A1 | 7/2008 |
| WO | 2008106108 A1 | 9/2008 |
| WO | 2008153831 A2 | 12/2008 |
| WO | 2009026420 A1 | 2/2009 |
| WO | 2009042577 A2 | 4/2009 |
| WO | 2009051995 A1 | 4/2009 |
| WO | 2010027636 A1 | 3/2010 |
| WO | 2010117841 A1 | 10/2010 |
| WO | 2011011346 A1 | 1/2011 |
| WO | 2011125303 A1 | 10/2011 |
| WO | 2012048277 A2 | 4/2012 |
| WO | 2012155035 A1 | 11/2012 |
| WO | 2013043868 A1 | 3/2013 |
| WO | 2014049656 A1 | 4/2014 |
| WO | 2014144651 A2 | 9/2014 |
| WO | 2014179326 A1 | 11/2014 |
| WO | 2014190264 A1 | 11/2014 |
| WO | WO-2015081109 A1 * | 6/2015 ............ A61M 5/007 |
| WO | 2015106107 A1 | 7/2015 |
| WO | 2015164783 A1 | 10/2015 |
| WO | 2016004329 A1 | 1/2016 |
| WO | 2016112163 A1 | 7/2016 |
| WO | 2016172467 A1 | 10/2016 |
| WO | 2016191485 A1 | 12/2016 |
| WO | 2017152036 A1 | 9/2017 |
| WO | 2018060505 A1 | 4/2018 |
| WO | 2018075386 A1 | 4/2018 |
| WO | 2018089882 A1 | 5/2018 |

OTHER PUBLICATIONS

Awai, K., et al., "Effect of contrast material injection duration and rate on aortic peak time and peak enhancement at dynamic CT involving injection protocol with dose tailored to patient weight," Radiology, vol. 230, Issue 1, pp. 142-150, 2004.

Bae, et al. "Aortic and Hepatic Contrast Medium Enhancement at CT—Part I, Prediction with a Computer Model", Radiology 1998;207:647-655.

Bae, K.T., et al., "Multiphasic Injection Method for Uniform Prolonged Vascular Enhancement at CT Angiography: Pharmacokinetic Analysis and Experimental Porcine Model," Radiology, vol. 216, Issue 3, pp. 872-880 (Sep. 2000).

Bae, K.T. et al, "Peak Contrast Enhancement in CT and MR Angiography: When Does it Occur and Why? Pharmacokinetic Study in a Porcine Model", Radiology, vol. 227, Jun. 2003, pp. 809-816.

Bae, K.T., et al., "Uniform vascular contrast enhancement and reduced contrast medium volume achieved by using exponentially decelerated contrast material injection method," Radiology, vol. 231, Issue 3, pp. 732-736, 2004.

Baker, Aaron; et al. "Fluid Mechanics Analysis of a Spring-Loaded Jet Injector." IEEE Transactions on Biomedical Engineering, vol. 46, No. 2, Feb. 1999.

Becker, C.R., et al., "Optimal contrast application for cardiac 4-detector-row computed tomography," Investigative Radiology, vol. 38, Issue 11, pp. 690-694 (Nov. 2003).

Blomley, M.J.K. and Dawson, P., "Bolus Dynamics: Theoretical and Experimental Aspects," The Brit. J. ofRadiology, vol. 70, No. 832, pp. 351-359 (Apr. 1997).

Brunette J.; et al, "Comparative rheology of low- and iso-osmolarity contrast agents at different temperature", Catheterization and Cardiovascular Interventions, 2008, vol. 71 Issue No. 1, 78-83.

Cademartiri, F. and Luccichenti, G., et al. "Sixteen-row multislice computed tomography: basic concepts, protocols, and enhanced clinical applications," Seminars in Ultrasound, CT and MRI, vol. 25, Issue 1, pp. 2-16, 2004.

Dardik, H. et al., "Remote Hydraulic Syringe Actuator," Arch. Surg., vol. 115, Issue 1, Jan. 1980.

Dawson, P. and Blomley, M., "The value of mathematical modelling in understanding contrast enhancement in CT with particular reference to the detection of hypovascular liver metastases," European Journal of Radiology, vol. 41, Issue 3, pp. 222-236 (Mar. 2002).

"Digital Injector for Angiography", Sias. (Sep. 7, 1993).

Disposable Low-Cost Catheter Tip Sensor Measures Blood Pressure during Surgery, Sensor (Jul. 1989).

EZ Chem Brochure, E-Z-EM, Inc. (Jul. 2007).

Fisher, M.E. and Teo, K.L., "Optimal insulin infusion resulting from a mathematical model of blood glucose dynamics", IEEE Transactions on Biomedical Engineering, vol. 36, Issue 4, pp. 479-486, 1989.

Flegal, K.M., et al., "Prevalence and trends in obesity among US adults," JAMA, 2002, vol. 288, Issue 14, pp. 1-4, (1999-2000).

Fleischmann, D. and Hittmair, K., "Mathematical analysis of arterial enhancement and optimization of bolus geometry for CT angiography using the discrete Fourier transform," Journal of Computer Assisted Tomography, vol. 23, Issue 3, pp. 474-484 (May/Jun. 1999).

Fleischmann, D., "Contrast Medium Injection Technique," In: U. Joseph Schoepf: "Multidetector-Row CT of The Thorax," pp. 47-59 (Jan. 22, 2004).

Fleischmann, D., "Present and Future Trends in Multiple Detector-Row CT Applications; CT Angiography", European Radiology, vol. 12, Issue 2, Supplement 2, Jul. 2002, pp. s11-s15.

Gardiner, G. A., et al., "Selective Coronary Angiography Using a Power Injector," AJR Am J Roentgenol., vol. 146, Issue 4, pp. 831-833 (Apr. 1986).

Garrett, J. S., et al., "Measurement of cardiac output by cine computed tomography," The American Journal of Cardiology, vol. 56, Issue 10, pp. 657-661, 1985.

Gembicki, F.W., "Vector Optimization for Control with Performance and Parameter Sensitivity Indices," PhD Thesis Case Western Reserve University, 1974.

Gentilini A., et al., "A new paradigm for the closed-loop intraoperative administration of analgesics in humans," IEEE Transactions on Biomedical Engineering, vol. 49, Issue 4, pp. 289-299 (Apr. 2002).

Gerlowski L.E. and Jain R.K., "Physiologically Based Pharmacokinetic Modeling: Principles and Applications," Journal of Pharmaceutical Sciences, vol. 72, pp. 1104-1125, Oct. 1983.

Goss, J. E., et al., "Power injection of contrast media during percutaneous transluminal coronary artery angioplasty," Catheterization and Cardiovascular Diagnosis, vol. 16, Issue 3, pp. 195-198 (Mar. 1989).

Grant, S.C.D. et al., "Reduction of Radiation Exposure to the Cardiologist during Coronary Angiography by the Use of A Remotely Controlled Mechanical Pump for Injection of Contrast Medium," Catheterization and Cardiovascular Diagnosis, vol. 25, Issue 2, pp. 107-109 (Feb. 1992).

Tackstein, N. et al., "Glomerular Filtration Rate Measured by Using Triphasic Helical CT with a Two-Point Patlak Plot Technique," Radiology, vol. 230, Issue 1, pp. 221-226, Jan. 2004.

Hansen, P.C, Regularization tools: a MATLAB package for analysis and solution of discrete ill-posed problems, Numerical Algorithms, vol. 6, Issue 1, pp. 35, 1994.

(56) References Cited

OTHER PUBLICATIONS

Hansen, P.C., "The truncated SVD as a method for regularization," BIT Numerical Mathematics, vol. 27, Issue 4, pp. 534-555, 1987.
Harris P., H. D. "The Human Pulmonary Circulation," Edinburgh, Churchill Livingstone, (Appendix I), 1986.
Hayes, M., "Statistical Digital Signal Processing and Modeling", New York, New York, Wiley and Sons, 1996, pp. 154-177, (Prony's method).
Heiken; J.P. et al., "Dynamic Contrast-Enhanced CT of the Liver: Comparison of Contrast Medium Injection Rates and Uniphasic and Biphasic Injection Protocols", Radiology, May 1993, vol. 187, No. 2, pp. 327-331.
"Infus O.R. Multi-Drug Syringe Pump with Smart Labels," Bard MedSystems Division Inc., pp. 2693-2696 (2005).
Ireland, M.A., et al., "Safety and Convenience of a Mechanical Injector Pump for Coronary Angiography," Catheterization and Cardiovascular Diagnosis, vol. 16, Issue 3, pp. 199-201 (1989).
Jacobs, J.R., "Algorithm for optimal linear model-based control with application to pharmacokinetic model-driven drug delivery," IEEE Transactions on Biomedical Engineering, vol. 37, Issue 1, pp. 107-109 (Jan. 1990).
Korosec, F.R., "Physical Principles of Phase-Contrast, Time-of-Flight, and Contrast-Enhanced MR Angiography," 41st Annual Meeting of American Association of Physicists in Medicine, Jul. 25-29, 1999.
Korosec, Frank, "Basic Principles of Phase-contrast, Time-of-flight, and Contrast-enhanced MR Angiography", 1999.
Krause, W, "Application of pharmacokinetics to computed tomography: injection rates and schemes: mono-, bi-, or multiphasic?," Investigative Radiology, vol. 31, Issue 2, pp. 91-100, Feb. 1996.
Krieger, R. A., "CO2-Power-Assisted Hand-Held Syringe: Better Visualization during Diagnostic and InterventionalAngiography," Cathet Cardiovasc Diagn., vol. 19, Issue 2, pp. 123-128 (Feb. 1990).
Liebel-Flarsheim Company, "Angiomat 6000 Digital Injection System—Operator's Manual", Document No. 600950, Rev. 1, Jan. 1990.
Mahnken, A. H., et al., "Determination of cardiac output with multislice spiral computed tomography: a validation study," Investigative Radiology, vol. 39, Issue 8, pp. 451-454, Aug. 2004.
Mahnken, A. H., et al., "Measurement of cardiac output from a test-bolus injection in multislice computed tomography," European Radiology, vol. 13, Issue 11, pp. 2498-2504, 2003.
Mark V/Mark V Plus Injector Operation Manual KMP 805P Rev. B. Medrad, Inc, 1990.
McClellan, J.H., "Parametric Signal Modeling," Chapter 1 in Advanced Topics in Signal Processing, Pentice-Hall, Englewood Cliffs, NJ (1988).
MCT and MCT Plus Injection Systems Operation Manual KMP 810P, Medrad, Inc, 1991.

Morden Peter.; et al., "The Role of Saline Flush Injection Rate in Displacement of CT Injectable Peripherally Inserted Central Catheter Tip During Power Injection of Contrast Material", AJR, Jan. 2014, 202, W13-W18.
Neatpisarnvanit, C. and Boston, J.R., "Estimation of plasma insulin from plasma glucose", IEEE Transactions on Biomedical Engineering, vol. 49, Issue 11, pp. 1253-1259, 2002.
Ostergaard, L., et al., "High resolution measurement of cerebral blood flow using intravascular tracer boluspassages. Part 1: Mathematical approach and statistical analysis," Magnetic Resonance in Medicine, vol. 36, Issue 5,pp. 715-725 (Nov. 1996).
"International Preliminary Report on Patentability from PCT Application No. PCT/US2017/061268", May 23, 2019.
Ostergaard, L., et al., "High resolution measurement of cerebral blood flow using intravascular tracer boluspassages. Part II: Experimental comparison and preliminary results," Magn Reson Med, vol. 36, Issue 5, pp. 726-736(Nov. 1996).
Parker, K.J., et al., "A Particulate Contrast Agent With Potential For Ultrasound Imaging of Liver," Ultrasound in Medicine & Biology, vol. 13, Issue 9, pp. 555-566 (Sep. 1987).
Rosen, B.R. et al., "Perfusion Imaging with NMR Contrast Agents," Magentic Resonance in Medicine, vol. 14, No. 2, pp. 249-265, May 1, 1990.
Sablayrolles, J-L, "Cardiac CT: Experience from Daily Practice", Advance CT, A GE Healthcare Publication. Aug. 2004.
Stevens, M.A., et al. "A Prospective Randomized Trial of Prevention Measures in Patients at High Risk for Contrast Nephropathy," J. of the ACC, vol. 33, Issue 2, pp. 403-411, Feb. 1999.
Swiss; Medical Care., "CT Expres Contrast Media Delivery System Operation Manual Rev 1", 2004.
"The Solution for Your IV Formulas", Valley Lab. Inc., E-39-15, 3399, 3400, 2646.
Ulrich; Medical., "Instructions for Use for ulrichInject CT motion—CT Contrast Media Injector", 2018.
Wada D.R. and Ward; D.S., "The hybrid model: a new pharmacokinetic model for computer-controlled infusion pumps", IEEE Transactions on Biomedical Engineering, 1994, vol. 41, Issue 2, pp. 134-142.
Wada, D.R. and Ward, D.S., "Open loop control of multiple drug effects in anesthesia", IEEE Transactions on Biomedical Engineering, vol. 42, Issue 7, pp. 666-677, 1995.
Yamashita, Y. et al., "Abdominal Helical CT: Evaluation of Optimal Doses of Intravenous Contrast Material—A Prospective Randomized Study," Radiology, vol. 216, Issue 3, pp. 718-723, Sep. 1, 2000.
Krieger, Richard; et al. "CO2 Power-Assisted Hand-Held Syringe: Better Visualization During Diagnostic and Interventional Angiography," Catheterization and Cardiovascular Diagnosis, vol. 19, pp. 123-128, 1990.
Awai Kazuo; et al, "Aortic and Hepatic Enhancement and Tumor-to-Liver Contrast: Analysis of the Effect of Different Concentrations of Contrast Material at Multi-Detector Row Helical CT.", Radiology, 2002, vol. 224; Issue 3., 757-763.
"The Solution for Our IV Formulas", IV 6500 Formulator Volumetric Pump, Valley Lab Inc., 39C 9410976 0000071 s, E-39-15, pp. 3399-3400, As early as 1980.

* cited by examiner

| | Volume offset (AO) in mL | | | | | | |
|---|---|---|---|---|---|---|---|
| Amt air | Regular* | No Silicon* | H2O* | H2O+soap* | Glycerol* | Fwd** | Back** | Mean | ±SD |
| 0 | 0.42 | 0.53 | 0.53 | 0.74 | 0.53 | 0.44 | 3.65 | 0.98 | 1.27 |
| 1 | 0.53 | 0.53 | 0.42 | 1.27 | 0.53 | | | 0.66 | 0.39 |
| 2 | 0.53 | 0.42 | 0.53 | 0.63 | 0.42 | 1.23 | 4.04 | 1.11 | 1.42 |
| 5 | 0.63 | 0.42 | 0.53 | 0.53 | 0.42 | | 2.96 | 0.92 | 1.11 |
| Mean | 0.53 | 0.48 | 0.50 | 0.79 | 0.48 | 0.84 | 3.55 | | |
| ±SD | 0.09 | 0.06 | 0.06 | 0.33 | 0.06 | 0.56 | 0.55 | | |

* Plunger position 150mL, flow rate 1.0 mL/s, fit over 7-100 psi, AO not varied
** Plunger position > 190mL, flow rate 0.2 mL/s, fit over 25-100 psi, AO varied

| Amt air | Volume offset (A0) in mL | | | | |
|---|---|---|---|---|---|
| | Regular | No Silicon | H2O | H2O+soap | Glycerol | Mean | ±SD |
| 0 | 0.31 | 0.31 | 0.42 | 0.53 | 0.21 | 0.36 | 0.12 |
| 1 | 0.31 | 0.31 | 0.42 | 1.53 | 0.31 | 0.38 | 0.10 |
| 2 | 0.42 | 0.42 | 0.31 | 0.31 | 0.42 | 0.38 | 0.06 |
| 5 | 0.53 | 0.42 | 0.31 | 0.53 | 0.31 | 0.42 | 0.11 |
| Mean | 0.39 | 0.37 | 0.37 | 0.48 | 0.31 | | |
| ±SD | 0.11 | 0.06 | 0.06 | 0.11 | 0.09 | | |

*Plunger position 150mL, flow rate 1.0 mL/s, fit over 7-100 psi, A0 not varied*

| | nRT (A1) in psi-mL | | | | | | |
|---|---|---|---|---|---|---|---|
| Amt air | Regular* | No Silicon* | H2O* | H2O+soap | Glycerol* | Fwd** | Back** | Mean | ±SD |
| 0 | 27.96 | 22.2 | 26.52 | 34.8 | 15.74 | 34.08 | 40.92 | 28.09 | 9.27 |
| 1 | 48.48 | 39.48 | 24.72 | 28.68 | 46.68 | | | 37.61 | 10.03 |
| 2 | 59.28 | 58.92 | 55.32 | 55.32 | 61.44 | 55.32 | 42.72 | 55.47 | 6.45 |
| 5 | 92.4 | 93.12 | 101.4 | 80.16 | 116.16 | | 84.48 | 94.62 | 14.34 |
| Mean | 57.03 | 53.43 | 51.99 | 49.74 | 60.01 | 44.70 | 56.04 | | |
| ±SD | 26.92 | 30.42 | 35.80 | 23.26 | 42.00 | 15.02 | 24.65 | | |

\* Plunger position 150mL, flow rate 1.0 mL/s, fit over 7-100 psi, AO not varied
\*\* Plunger position > 190mL, flow rate 0.2 mL/s, fit over 25-100 psi, AO varied

| Amt air | nRT (A1) in psi-mL | | | | | |
| --- | --- | --- | --- | --- | --- | --- |
| | Regular | No Silicon | H2O | H2O+soap | Glycerol | Mean | ±SD |
| 0 | 8.88 | 20.04 | 21.48 | 26.16 | 6.36 | 16.58 | 8.54 |
| 1 | 33 | 38.76 | 29.4 | 36.6 | 23.64 | 32.28 | 6.00 |
| 2 | 37.32 | 55.68 | 42 | 44.88 | 33.36 | 42.65 | 8.51 |
| 5 | 67.2 | 102.84 | 86.28 | 97.44 | 44.52 | 79.66 | 23.91 |
| Mean | 36.60 | 54.33 | 44.79 | 51.27 | 26.97 | | |
| ±SD | 23.93 | 35.46 | 28.92 | 31.72 | 16.17 | | |

*Plunger position 150mL, flow rate 1.0 mL/s, fit over 7-100 psi, A0 not varied*

| Amt air | Pfriction (A2) in psi ||||||| |
|---|---|---|---|---|---|---|---|
| | Regular* | No Silicon* | H2O* | H2O+soap* | Glycerol* | Fwd** | Back** | Mean | ±SD |
| 0 | 10.92 | 14.52 | 13.08 | 7.86 | 15.96 | 14.16 | 20.28 | 13.83 | 4.04 |
| 1 | 19.11 | 13.66 | 13.89 | 10.38 | 12.09 | | | 13.83 | 1.63 |
| 2 | 16.05 | 15.79 | 15.96 | 9.61 | 13.17 | 21.09 | 16.32 | 15.43 | 3.80 |
| 5 | 14.83 | 13.84 | 13.26 | 11.37 | 10.2 | 17.63 | 11.28 | 12.46 | 1.51 |
| Mean | 15.23 | 14.45 | 14.05 | 9.81 | 12.86 | 17.63 | 15.96 | | |
| ±SD | 3.39 | 0.97 | 1.32 | 1.48 | 2.41 | 4.90 | 4.51 | | |

\* Plunger position 150mL, flow rate 1.0 mL/s, fit over 7-100 psi, A0 not varied
\*\* Plunger position > 190mL, flow rate 0.2 mL/s, fit over 25-100 psi, A0 varied

| | Stiffness (A3) in psi/mL | | | | | | | |
|---|---|---|---|---|---|---|---|---|
| Amt air | Regular* | No Silicon* | H2O* | H2O+soap* | Glycerol* | Fwd** | Back** | Mean | ±SD |
| 0 | 69.31 | 44.08 | 52.78 | 70.18 | 48.43 | 44.08 | 56.26 | 55.02 | 9.85 |
| 1 | 712.24 | 55.39 | 52.78 | 47.12 | 99.76 | | | 193.46 | 24.25 |
| 2 | 141.5 | 61.48 | 176.32 | 65.83 | 110.2 | 80.62 | 38.86 | 96.40 | 48.89 |
| 5 | 56.26 | 37.99 | 294.64 | 31.03 | 145 | | 19.72 | 97.44 | 117.04 |
| Mean | 244.83 | 49.74 | 144.13 | 53.54 | 100.85 | 62.35 | 38.28 | | |
| ±SD | 313.86 | 10.64 | 116.02 | 18.04 | 39.94 | 25.84 | 18.28 | | |

\* Plunger position 150mL, flow rate 1.0 mL/s, fit over 7-100 psi, AO not varied
\*\* Plunger position > 190mL, flow rate 0.2 mL/s, fit over 25-100 psi, AO varied

| | Stiffness (A3) in psi/mL | | | | | |
|---|---|---|---|---|---|---|
| Amt air | Regular | No Silicon | H2O | H2O+soap | Glycerol | Mean | ±SD |
| 0 | 80.62 | 92.8 | 120.64 | 162.4 | 57.13 | 102.72 | 40.46 |
| 1 | 315.52 | 151.96 | 190.24 | 134.56 | 77.14 | 173.88 | 89.04 |
| 2 | 80.62 | 406 | 99.76 | 82.36 | 58 | 145.35 | 146.46 |
| 5 | 31.03 | 475.6 | 85.84 | 120.64 | 19.06 | 146.43 | 188.57 |
| Mean | 126.95 | 281.59 | 124.12 | 124.99 | 52.83 | | |
| ±SD | 127.87 | 187.58 | 46.34 | 33.30 | 24.34 | | |

*Plunger position 150mL, flow rate 1.0 mL/s, fit over 7-100 psi, A0 not varied*

| Amt air | Slope (mL/psi, over 20-35 psi) | | | | | | | |
|---|---|---|---|---|---|---|---|---|
| | Regular* | No Silicon* | H2O* | H2O+soap* | Glycerol* | Fwd** | Back** | Mean | ±SD |
| 0 | 0.058 | 0.072 | 0.061 | 0.050 | 0.051 | 0.093 | 0.093 | 0.068 | 0.018 |
| 1 | 0.102 | 0.093 | 0.051 | 0.067 | 0.066 | | | 0.076 | 0.021 |
| 2 | 0.109 | 0.138 | 0.072 | 0.066 | 0.065 | 0.107 | 0.114 | 0.096 | 0.028 |
| 5 | 0.145 | 0.162 | 0.150 | 0.101 | 0.129 | 0.150 | 0.150 | 0.141 | 0.020 |
| Mean | 0.104 | 0.116 | 0.084 | 0.071 | 0.078 | 0.117 | 0.119 | | |
| ±SD | 0.036 | 0.041 | 0.045 | 0.021 | 0.035 | 0.030 | 0.128 | | |

* Plunger position 150mL, flow rate 1.0 mL/s
** Plunger position > 190mL, flow rate 0.2 mL/s

| | Slope (mL/psi, over 20-35 psi) | | | | | |
|---|---|---|---|---|---|---|
| Amt air | Regular | No Silicon | H2O | H2O+soap | Glycerol | Mean | ±SD |
| 0 | 0.015 | 0.051 | 0.045 | 0.022 | 0.036 | 0.034 | 0.015 |
| 1 | 0.037 | 0.051 | 0.037 | 0.044 | 0.058 | 0.045 | 0.009 |
| 2 | 0.051 | 0.050 | 0.059 | 0.068 | 0.073 | 0.060 | 0.010 |
| 5 | 0.108 | 0.143 | 0.104 | 0.109 | 0.161 | 0.125 | 0.026 |
| Mean | 0.053 | 0.074 | 0.061 | 0.061 | 0.082 | | |
| ±SD | 0.040 | 0.046 | 0.030 | 0.037 | 0.055 | | |

*Plunger position 50mL, flow rate 1.0 mL/s*

METHODS AND SYSTEMS FOR VERIFYING THE CONTENTS OF A SYRINGE USED FOR MEDICAL FLUID DELIVERY

CROSS REFERENCE TO RELATED APPLICATIONS

The present application is a 371 national phase application of PCT International Application No. PCT/US2017/061268, filed Nov. 13, 2017, and claims priority to U.S. Provisional Patent Application No. 62/421,661, filed Nov. 14, 2016, the disclosures of which is hereby incorporated herein by reference in their entirety.

BACKGROUND OF THE DISCLOSURE

Field of the Disclosure

The present disclosure is directed to medical fluid delivery applications and, particularly, to apparatuses and techniques for verifying the contents of a syringe used in delivering a medical fluid to a patient.

Description of Related Art

In many medical diagnostic and therapeutic procedures, a medical practitioner, such as a physician, injects a patient with a medical fluid. In recent years, a number of injector-actuated syringes and powered injectors for pressurized injection of fluids, such as contrast solution (often referred to simply as "contrast"), have been developed for use in procedures such as angiography, computed tomography (CT), ultrasound, nuclear medicine, molecular imaging, and NMR/MRI. In general, these powered injectors are designed to deliver a preset amount of contrast at a preset flow or delivery rate.

In a typical angiographic procedure, the medical practitioner places a cardiac catheter into a vein or artery. The catheter is connected to either a manual or to an automatic fluid injection mechanism. A typical manual fluid injection mechanism includes a syringe in fluid connection with a catheter connection. The fluid path may also include, for example, a source of contrast, a source of flushing fluid, typically saline, and a pressure transducer to measure patient blood pressure. In a typical system, the source of contrast is connected to the fluid path via a valve, for example, a three-way stopcock. The source of saline and the pressure transducer may also be connected to the fluid path via additional valves, such as stopcocks. The operator of the manual contrast injection mechanism controls the syringe and each of the valves to draw saline or contrast into the syringe and to inject the contrast or saline into the patient through the catheter connection.

Automatic fluid injection mechanisms typically include a syringe connected to one or more powered injectors having, for example, a powered linear actuator. Typically, an operator enters settings into an electronic control system of the powered injector for a fixed volume of contrast and/or saline, and a fixed rate of injection for each. Automatic fluid injection mechanisms provide improved control over manual apparatus where successful use of such manual devices is dependent on the skill of the medical practitioner operating the device. As in a manual system, the fluid path from the automatic fluid injection mechanism to the patient includes, for example, a source of contrast, a source of flushing fluid, typically saline, and a pressure transducer. The source of contrast is connected to the fluid path via a valve, for example, a three-way stopcock. The source of saline and the pressure transducer may also be connected to the fluid path via additional valves, such as stopcocks.

The injected contrast and/or saline are delivered to a patient's vasculature through the catheter inserted into the patient's body, such as the patient's groin area. A dose of contrast is referred to as a bolus. Once the bolus of contrast is delivered to the desired site, that area is imaged using a conventional imaging technique, such as angiography imaging or scanning, CT, MRI, ultrasound, or other imaging modalities. The contrast becomes clearly visible against the background of the surrounding tissue.

One concern in any injection procedure is to ensure that the correct fluid is loaded into the syringe and injected into the patient. The use of automatic fluid injectors that can load injection syringes with the push of a button may exacerbate this issue as user errors in the setup or operation of the system may go unnoticed by an operator. For example, while allowing an injector to draw automatically from one of multiple fluid sources creates certain efficiencies in the injection process, incorrect configuration of the fluid sources may cause the injector to draw from and inject the wrong fluid. In addition, air trapped within a syringe that has been automatically loaded is not desired.

SUMMARY

In accordance with some aspects of this disclosure, described is a fluid delivery system that includes a syringe, a fluid injector for drawing fluid into and dispensing fluid from the syringe, one or more sensors adapted to measure a force required to draw the fluid into and/or dispensing fluid from the syringe, a processor in communication with the one or more sensors, and a non-transitory, computer-readable storage medium in operable communication with the processor. The computer-readable storage medium contains one or more programming instructions that, when executed, cause the processor to receive from the one or more sensors one or more measurements of the force required to draw the fluid into the syringe and determine from the one or more measurements of the force required to draw the fluid into and/or dispensing fluid from the syringe whether a correct fluid is being drawn into the syringe.

According to a non-limiting embodiment, the programming instructions, when executed, cause the processor to determine from the one or more measurements of the force required to draw the fluid into and/or dispensing fluid from the syringe whether the correct fluid is being drawn into the syringe by comparing at least one of the one or more measurements of the force required to draw the fluid into and/or dispensing fluid from the syringe to a predetermined steady state force value.

According to a non-limiting embodiment, the programming instructions, when executed, cause the processor to trigger an alarm if the at least one of the one or more measurements of the force required to draw the fluid into and/or dispensing fluid from the syringe is sufficiently different than the predetermined steady state force value.

In another non-limiting embodiment, the programming instructions, when executed, cause the processor to stop operation of the fluid injector if the at least one of the one or more measurements of the force required to draw the fluid into and/or dispensing fluid from the syringe is sufficiently different than the predetermined steady state force value.

In another non-limiting embodiment, the system further includes one or more sensors adapted to measure a force required to dispense the fluid from the syringe. The one or more programming instructions, when executed, cause the processor to receive one or more measurements of the force required to dispense the fluid from the syringe and determine from the one or more measurements of the force required to dispense the fluid from the syringe whether a correct fluid is being dispensed from the syringe.

According to another aspect of this disclosure, described is a method of verifying the contents of a syringe in a fluid delivery system. The method includes drawing a fluid into the syringe, obtaining, using one or more sensors, one or more measurements of the force required to draw the fluid into and/or dispensing fluid from the syringe, and determining, from the one or more measurements of the force required to draw the fluid into and/or dispensing fluid from the syringe, whether the fluid is a correct fluid.

In a non-limiting embodiment, determining from the one or more measurements of the force required to draw the fluid into and/or dispensing fluid from the syringe whether the fluid is the correct fluid includes comparing at least one of the one or more measurements of the force required to draw the fluid into the syringe to a predetermined steady state force value.

In a non-limiting embodiment, the method further includes receiving the predetermined steady state force value from a user interface associated with the fluid delivery system or from a database associated with the fluid delivery system.

In another non-limiting embodiment, the method includes triggering an alarm if it is determined that the fluid is not the correct fluid.

According to another aspect of this disclosure, described is a fluid delivery system that includes a syringe, a fluid injector for drawing fluid into and dispensing fluid from the syringe, one or more sensors adapted to measure a force required to dispense the fluid from the syringe, a processor in communication with the one or more sensors, and a non-transitory, computer-readable storage medium in operable communication with the processor. The computer-readable storage medium contains one or more programming instructions that, when executed, cause the processor to receive one or more measurements of the force required to dispense the fluid from the syringe from the one or more sensors and determine from the one or more measurements of the force required to dispense the fluid from the syringe whether a correct fluid is being dispensed from the syringe.

In a non-limiting embodiment, the programming instructions, when executed, cause the processor to determine from the one or more measurements of the force required to dispense the fluid from the syringe whether the correct fluid is being dispensed from the syringe by comparing at least one of the one or more measurements of the force required to dispense the fluid from the syringe to a predetermined steady state force value.

In another non-limiting embodiment, the programming instructions, when executed, cause the processor to trigger an alarm if the at least one of the one or more measurements of the force required to dispense the fluid from the syringe is sufficiently different than the predetermined steady state force value.

In a non-limiting embodiment, the programming instructions, when executed, cause the processor to stop operation of the fluid injector if the at least one of the one or more measurements of the force required to dispense the fluid from the syringe is sufficiently different than the predetermined steady state force value.

According to another aspect of this disclosure, described is a method of verifying the contents of a syringe in a fluid delivery system. The method includes dispensing a fluid from the syringe, obtaining, using one or more sensors, one or more measurements of the force required to dispense the fluid from the syringe, and determining, from the one or more measurements of the force required to dispense the fluid from the syringe, whether the fluid is a correct fluid.

In certain non-limiting embodiments, determining from the one or more measurements of the force required to dispense the fluid from the syringe whether the fluid is the correct fluid comprises comparing at least one of the one or more measurements of the force required to dispense the fluid from the syringe to a predetermined steady state force value.

In certain non-limiting embodiments, the method further includes receiving the predetermined steady state force value from a user interface associated with the fluid delivery system or from a database associated with the fluid delivery system.

In other non-limiting embodiments, the further includes triggering an alarm if it is determined that the fluid is not the correct fluid.

In one non-limiting embodiment, determining, from the one or more measurements of the force required to dispense the fluid from the syringe, whether the fluid is a correct fluid comprises determining whether the fluid comprises air.

In another non-limiting embodiment, determining, from the one or more measurements of the force required to dispense the fluid from the syringe, whether the fluid is a correct fluid comprises determining the compressibility of the fluid in the syringe.

Another aspect of this disclosure is a fluid delivery system that includes a fluid path set, a fluid injector for delivering a fluid through the fluid path set, one or more sensors adapted to measure the force required to deliver the fluid through the fluid path set, a processor in communication with the one or more sensors, and a non-transitory, computer-readable storage medium in operable communication with the processor. The computer-readable storage medium contains one or more programming instructions that, when executed, cause the processor to receive one or more measurements of the force required to deliver the fluid through the fluid path set from the one or more sensors and detect an increase in the force required to deliver the fluid through the fluid path set. The fluid path set includes a syringe, a purge tube, a connector tube creating a fluid path between the syringe and the purge tube, and a flow restrictor positioned in the purge tube and adapted to restrict fluid flow through the purge tube.

The present disclosure may be further described by the following clauses:

Clause 1: A fluid delivery system, comprising: a syringe; a fluid injector for drawing fluid into and dispensing fluid from the syringe; one or more sensors adapted to measure a force required to draw the fluid into the syringe; a processor in communication with the one or more sensors; and a non-transitory, computer-readable storage medium in operable communication with the processor, wherein the computer-readable storage medium contains one or more programming instructions that, when executed, cause the processor to receive from the one or more sensors one or more measurements of the force required to draw the fluid into the syringe and determine from the one or more measurements of the force required to draw the fluid into the syringe whether a correct fluid is being drawn into the syringe.

Clause 2: The system of clause 1, wherein the programming instructions, when executed, cause the processor to determine from the one or more measurements of the force required to draw the fluid into the syringe whether the correct fluid is being drawn into the syringe by comparing at least one of the one or more measurements of the force required to draw the fluid into the syringe to a predetermined steady state force value.

Clause 3: The system of clause 2, wherein the programming instructions, when executed, cause the processor to trigger an alarm if the at least one of the one or more measurements of the force required to draw the fluid into the syringe is sufficiently different than the predetermined steady state force value.

Clause 4: The system of clause 2 or 3, wherein the programming instructions, when executed, cause the processor to stop operation of the fluid injector if the at least one of the one or more measurements of the force required to draw the fluid into the syringe is sufficiently different than the predetermined steady state force value.

Clause 5: The system of any of clauses 1 to 4, further comprising one or more sensors adapted to measure a force required to dispense the fluid from the syringe, wherein the one or more programming instructions, when executed, cause the processor to receive one or more measurements of the force required to dispense the fluid from the syringe and determine from the one or more measurements of the force required to dispense the fluid from the syringe whether a correct fluid is being dispensed from the syringe.

Clause 6: A method of verifying the contents of a syringe in a fluid delivery system, comprising: drawing a fluid into the syringe; obtaining, using one or more sensors, one or more measurements of the force required to draw the fluid into the syringe; and determining, from the one or more measurements of the force required to draw the fluid into the syringe, whether the fluid is a correct fluid.

Clause 7: The method of clause 6, wherein determining from the one or more measurements of the force required to draw the fluid into the syringe whether the fluid is the correct fluid comprises comparing at least one of the one or more measurements of the force required to draw the fluid into the syringe to a predetermined steady state force value.

Clause 8: The method of clause 7, further comprising receiving the predetermined steady state force value from a user interface associated with the fluid delivery system or from a database associated with the fluid delivery system.

Clause 9: The method of any of clauses 6 to 8, further comprising triggering an alarm if it is determined that the fluid is not the correct fluid.

Clause 10: A fluid delivery system, comprising: a syringe; a fluid injector for drawing fluid into and dispensing fluid from the syringe; one or more sensors adapted to measure a force required to dispense the fluid from the syringe; a processor in communication with the one or more sensors; and a non-transitory, computer-readable storage medium in operable communication with the processor, wherein the computer-readable storage medium contains one or more programming instructions that, when executed, cause the processor to receive one or more measurements of the force required to dispense the fluid from the syringe from the one or more sensors and determine from the one or more measurements of the force required to dispense the fluid from the syringe whether a correct fluid is being dispensed from the syringe.

Clause 11: The system of clause 10, wherein the programming instructions, when executed, cause the processor to determine from the one or more measurements of the force required to dispense the fluid from the syringe whether the correct fluid is being dispensed from the syringe by comparing at least one of the one or more measurements of the force required to dispense the fluid from the syringe to a predetermined steady state force value.

Clause 12: The system of clause 11, wherein the programming instructions, when executed, cause the processor to trigger an alarm if the at least one of the one or more measurements of the force required to dispense the fluid from the syringe is sufficiently different than the predetermined steady state force value.

Clause 13: The system of clauses 11 or 12, wherein the programming instructions, when executed, cause the processor to stop operation of the fluid injector if the at least one of the one or more measurements of the force required to dispense the fluid from the syringe is sufficiently different than the predetermined steady state force value.

Clause 14: A method of verifying the contents of a syringe in a fluid delivery system, comprising: dispensing a fluid from the syringe; obtaining, using one or more sensors, one or more measurements of the force required to dispense the fluid from the syringe; and determining, from the one or more measurements of the force required to dispense the fluid from the syringe, whether the fluid is a correct fluid.

Clause 15: The method of clause 14, wherein determining from the one or more measurements of the force required to dispense the fluid from the syringe whether the fluid is the correct fluid comprises comparing at least one of the one or more measurements of the force required to dispense the fluid from the syringe to a predetermined steady state force value.

Clause 16: The method of clause 15, further comprising receiving the predetermined steady state force value from a user interface associated with the fluid delivery system or from a database associated with the fluid delivery system.

Clause 17: The method of any of clauses 14 to 16, further comprising triggering an alarm if it is determined that the fluid is not the correct fluid.

Clause 18: The method of any of clauses 14 to 17, wherein determining, from the one or more measurements of the force required to dispense the fluid from the syringe, whether the fluid is a correct fluid comprises determining whether the fluid comprises air.

Clause 19: The method of any of clauses 14 to 18, wherein determining, from the one or more measurements of the force required to dispense the fluid from the syringe, whether the fluid is a correct fluid comprises determining the compressibility of the fluid in the syringe.

Clause 20: A fluid delivery system, comprising: a fluid path set, comprising: a syringe; a purge tube; a connector tube creating a fluid path between the syringe and the purge tube; and a flow restrictor positioned in the purge tube and adapted to restrict fluid flow through the purge tube; a fluid injector for delivering a fluid through the fluid path set; one or more sensors adapted to measure the force required to deliver the fluid through the fluid path set; a processor in communication with the one or more sensors; and a non-transitory, computer-readable storage medium in operable communication with the processor, wherein the computer-readable storage medium contains one or more programming instructions that, when executed, cause the processor to receive one or more measurements of the force required to deliver the fluid through the fluid path set from the one or more sensors and detect an increase in the force required to deliver the fluid through the fluid path set.

These and other features and characteristics of the disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures.

DETAILED DESCRIPTION

Figure 1:
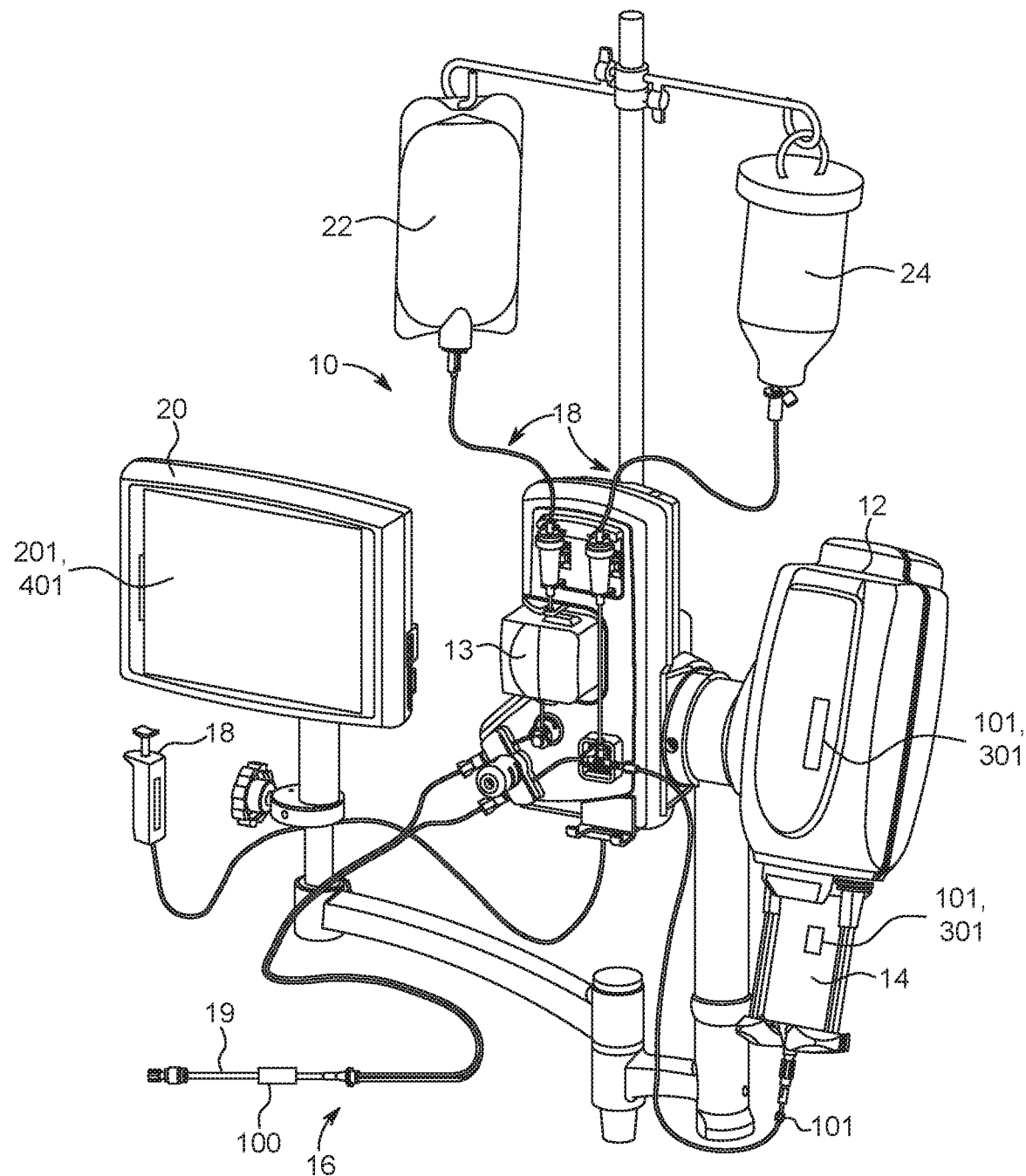
FIG. 1 is a perspective view of a fluid delivery system according to one embodiment.

For purposes of the description hereinafter, spatial orientation terms shall relate to the embodiment as it is oriented in the drawing figures. However, it is to be understood that the various embodiments of this disclosure may assume alternative variations and step sequences, except where expressly specified to the contrary. It is also to be understood that the specific devices and processes illustrated in the attached drawings, and described in the following specification, are simply exemplary. Hence, specific dimensions and other physical characteristics related to embodiments disclosed herein are not to be considered as limiting.

As used in the specification, the singular form of "a", "an", and "the" include plural referents unless the context clearly dictates otherwise.

Unless otherwise indicated, all ranges or ratios disclosed herein are to be understood to encompass any and all subranges or sub-ratios subsumed therein. For example, a stated range or ratio of "1 to 10" should be considered to include any and all subranges between (and inclusive of) the minimum value of 1 and the maximum value of 10; that is, all subranges or sub-ratios beginning with a minimum value of 1 or more and ending with a maximum value of 10 or less, such as but not limited to, 1 to 6.1, 3.5 to 7.8, and 5.5 to 10.

All documents, such as but not limited to issued patents and patent applications, referred to herein, and unless otherwise indicated, are to be considered to be "incorporated by reference" in their entirety.

Pressures as shown herein are the pressure differences that drive fluid motion through a fluid path, generally with the pressure at the outlet or receiving element of the fluid path being defined to be at zero pressure. When filling a syringe, there is a negative pressure within the syringe body with respect to the outside atmosphere, and the driving pressure difference P is defined as positive because the pressure in the source of the filling fluid is positive with respect to the outlet or receiving element and thus drives the fluid from the source to the outlet or receiving element. Similarly, when fluid is being dispensed the pressure at the outlet or receiving element is generally, but not necessarily, at or close to atmospheric pressure or blood pressure and a positive pressure at the source for that phase of operation (the delivery phase) drives the fluid to a corresponding outlet or receiving element.

FIG. 1 is a perspective view of a fluid delivery system 10. The fluid delivery system 10 is adapted for delivering fluids to a patient during a medical injection procedure. For example, the fluid delivery system 10 may be used during an angiographic or a similar medical imaging procedure to inject a contrast solution and/or a common flushing agent, such as saline, into the body of a patient. An example of such a fluid injection or delivery system is disclosed in U.S. Pat. No. 7,094,216, the disclosure of which is incorporated herein by reference in its entirety. Additional examples of fluid delivery systems are disclosed in the following references: U.S. Pat. Nos. 7,556,619; 8,337,456; 8,147,464; and 8,540,698, the disclosures of which are incorporated herein by reference in their entireties.

The fluid delivery system 10 generally includes a powered fluid injector 12 that is adapted to support and actuate a syringe 14 storing a first injection fluid 24, typically a contrast agent or medium, for injection to a patient during a medical imaging procedure. The fluid delivery system 10 further includes a second injection fluid 22, typically saline or other flushing fluid, stored in a second container that may be mixed with the first injection fluid 24 or delivered separately to the patient. The injector 12 is generally used to supply the first and second injection fluids 24, 22 under pressure to the fluid path set 16 and, ultimately, the patient. In one embodiment, the second injection fluid 22 may be delivered by way of a second powered injector, as described in greater detail below. In another embodiment, the second injection fluid 22 may be delivered by way of a pump, such as a piston pump or a peristaltic pump. The injector 12 may be controlled by a hand controller to supply the first and second injection fluids 24, 22 at discrete and preselected flow rates.

The construction and operation of syringe 14 is well known in the art. An example of a suitable high pressure syringe may be found in United States Patent Application Publication No. 2009/0216192, incorporated herein by reference for teachings related to the high pressure syringe and, further, the powered fluid injector 12. Syringe 14 generally comprises an elongated, cylindrical syringe body defining an injection section at the distal end and an expansion section for holding a fluid at the proximal end. The injection section tapers to form an elongated discharge neck, which has a relatively small inner diameter. The expansion section can accommodate a syringe plunger. Actuation of the syringe plunger, such as by injector 12, causes fluid to be drawn into or discharged from syringe 14, as is known in the art.

The injector 12 is operatively associated with a fluid control module 20. The fluid control module 20 may be adapted for controlling the operation of the fluid delivery system 10 by allowing the user to manually select the injection parameters, or select a pre-defined injection protocol. Alternatively, this functionality may reside with an external control unit or with the powered injector 12. In either case, the fluid control module 20 controls the injection pressure, the volume of the first and/or second injection fluids 24, 22 to be delivered to the patient, and the ratio of the first injection fluid 24 relative to the second injection fluid 22. Fluid control module 20 can also control the loading of syringe 14 with the first or second injection fluid 24, 22. Fluid control module 20 can include one or more processors that may have stored thereon, or be in communication with, program instructions that, when executed by the processor, cause the processor to control the operation of the fluid delivery system 10. For example, a computer-readable medium may be memory located in or in communication with fluid control module 20 for storing the program instructions.

The fluid delivery system 10 is generally adapted to connect to a fluid path set 16 for delivering the first and second injection fluids 24, 22. The flow of contrast and saline is regulated by the fluid control module 20 which controls the various valves and flow regulating structures in the fluid path set 16 to regulate the delivery of contrast and saline to the patient based on user selected injection parameters, such as total injection volume and ratio of contrast solution and saline. The fluid path set 16 can further connect the syringe 14 to a single-patient disposable set (SPDS) 19 which is associated with the patient for supplying the contrast and saline to the patient.

Figure 2:
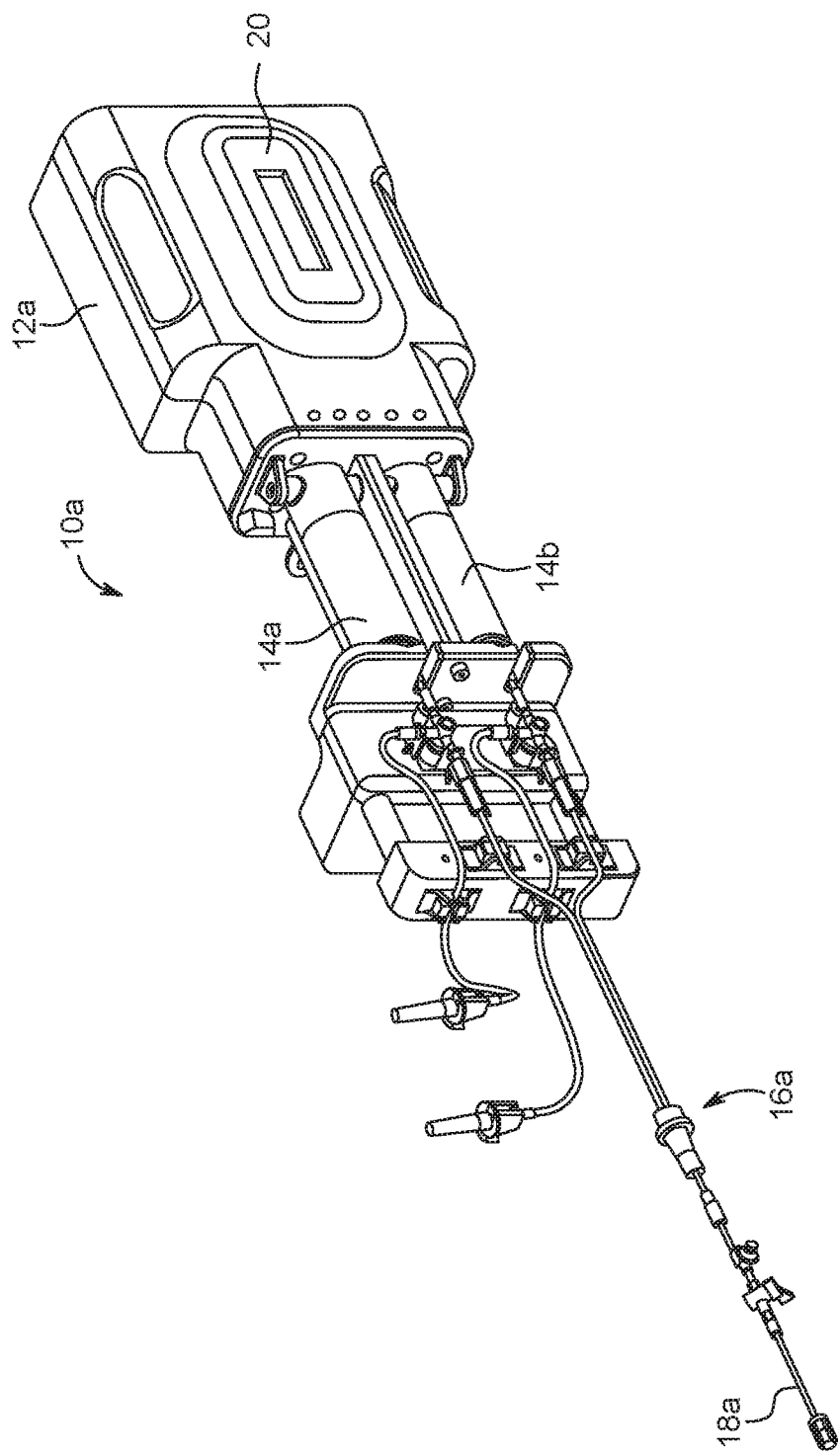
FIG. 2 is a perspective view of a fluid delivery system according to another embodiment.
Figure 3:
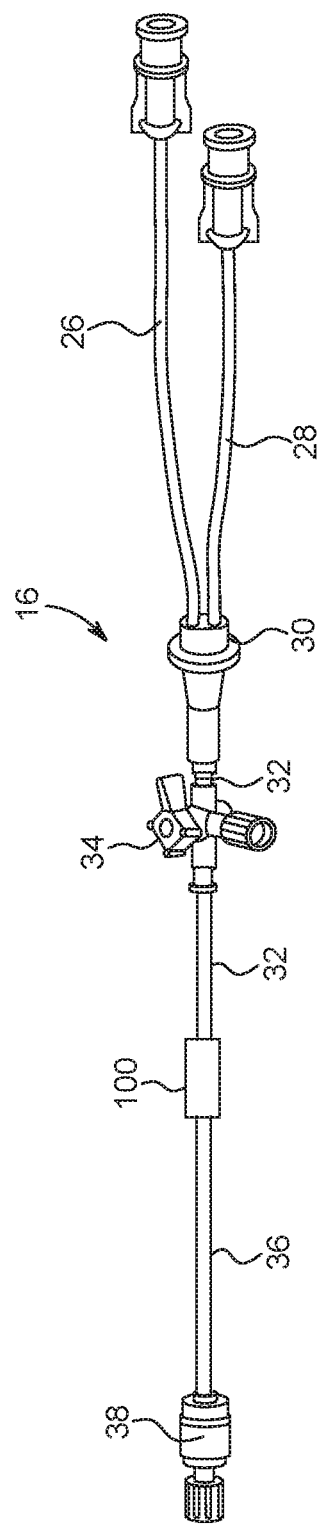
FIG. 3 is a schematic view of a fluid path set and a single-patient disposable set for use in a fluid delivery system in accordance with one embodiment.

FIG. 2 illustrates an alternative embodiment of a fluid delivery system 10a having a powered fluid injector 12a adapted to interface with two syringes 14a, 14b which may be fluidly connected to a source of first injection fluid 22 and a source of second injection fluid 24 or any two desired medical fluids. The injector 12a can be at least a dual-syringe injector, wherein two fluid delivery syringes 14a, 14b may be oriented in a side-by-side or other suitable relationship and which are separately actuated by respective piston elements associated with the injector 12a. In another embodiment, the injector 12a may be a dual-pump injector, wherein two pumps, such as piston pumps and/or peristaltic pumps, are separately actuated and controlled. The fluid path set 16a may be interfaced with the injector 12a in a similar manner to that described previously in connection with the fluid delivery system 10 described with reference to FIG. 1. In particular, the injector 12a is operatively associated with a fluid control module 20a (see FIG. 1). The fluid control module 20a is generally adapted to support a fluid path set 16a that is generally adapted to fluidly connect to the first syringe 14a having a first injection fluid 24, such a contrast solution. The fluid path set 16a is further connected to the second syringe 14b having a second injection fluid 22, such as saline. The first and second syringes 14a, 14b may have a different size relative to each other or may have the same size. One of the first syringe 14a and the second syringe 14b may be larger relative to the other of the first syringe 14a and the second syringe 14b to receive a larger volume of fluid therein. The flow of the first injection fluid 24 from the first syringe 14a and the second injection fluid 22 from the second syringe 14b is regulated by the fluid control module 20a, which controls the various valves and flow regulating structures to regulate the delivery of first and second medical fluids to the patient based on user selected injection parameters, such as total injection volume and ratio of contrast solution and saline. The fluid path set 16a further connects to a SPDS 18a which is associated with the patient for supplying the first and second medical fluids to the patient. A suitable multi-syringe fluid injector for use with the above-described system is described in U.S. Patent Application Publication No. 2012/0123257, the disclosure of which is incorporated herein by reference in its entirety. Other relevant multi-fluid delivery systems are found in U.S. Patent Application Publication Nos. U.S. 2004/0064041 and U.S. 2005/0113754, and International Application Publication WO 2012/155035, the disclosures of which are incorporated herein by reference.

In yet another embodiment, a three-fluid delivery system (not shown) may be provided. Similar to power-operated fluid delivery systems described with reference to FIGS. 1-2, a three-fluid delivery system may include a first injector or pump adapted to deliver a first injection fluid 24, such as a contrast medium, a second injector or pump adapted to deliver a second injection fluid 22, such as saline, and a third injector or pump adapted to deliver a third injection fluid, for example a second type or concentration of contrast medium compared to the first injection fluid 24. A fluid path set is provided for delivering and mixing the first, second, and third injection fluids in a desired ratio prior to being delivered to a patient. An exemplary three-fluid delivery system is disclosed in FIGS. 60-62 of U.S. Patent Application Publication No. 2012/0123257.

In another embodiment, a manually-controlled fluid delivery system (not shown) may be provided. Similar to power-operated fluid delivery systems described with reference to FIGS. 1-2, a manually-controlled fluid delivery system may include a first injector adapted to actuate a first syringe storing a first injection fluid 24, such as a contrast medium, for injection to a patient during a medical procedure. The manually-controlled fluid delivery system may also include a second injector adapted to actuate a second syringe storing a second injection fluid 22, such as saline. A fluid path set is provided for delivering and mixing the first injection fluid 24 and the second injection fluid 22 in a desired ratio prior to being delivered to a patient. An exemplary manually-controlled fluid delivery system is disclosed in U.S. Pat. No. 9,259,527, which disclosure is incorporated herein by reference.

In another embodiment, a manually-controlled fluid delivery system incorporating tactile feedback or control (not shown) may be provided. An exemplary manually-controlled fluid delivery system incorporating tactile feedback or control is disclosed in U.S. Pat. No. 5,840,026, incorporated herein by this reference. In another embodiment, a manually powered fluid delivery system (not shown) is disclosed. In such a system the sensor may incorporate at least a force sensor and a position sensor as shown in U.S. Pat. No. 5,840,026, which may be used to measurements of the force required to draw the fluid into and/or dispense the fluid from the syringe and the position of the manually activated plunger in the syringe and thus determine from the one or more measurements of the force required to draw the fluid into and/or dispense the fluid from the syringe whether a correct fluid is being drawn into and/or dispensed from the syringe.

Syringe 14 may be configured to deliver one or more injection fluids 24, 22, and may be in communication with a source of each injection fluid. In response to a command from, e.g., fluid control module 20, injector 12 can operate to load one or more syringe 14 by drawing one of these injection fluids (or a mixture of these fluids) into the one or more syringe 14 for delivery to a patient. According to the present disclosure, fluid delivery system 10 can be configured with a fluid input verification mechanism to verify that the fluid being drawn into syringe is correct. For example, fluid input verification mechanism can help verify that the fluid being drawn into each of the one or more syringe 14, such as in response to a command from fluid control module 20, is the fluid that is intended to be drawn into each of syringe 14. According to certain aspects, the fluid input verification mechanism may accomplish this, at least in part, by measuring the force or pressure required to draw the injection fluid 24, 22 into syringe 14 and comparing the measured force or pressure value with one or more of the expected force or pressure value for that particular fluid for example due to differences in fluid viscosities, the particular syringe and disposable fluid path set uses, and the particular fill conditions used, such as flow rate and/or vacuum applied. If there is a mismatch between actual expected pressure and/or force and measured pressure and/or force, appropriate indications, alarms, notifications and/or actions may be taken.

The following operational discussion of the fluid input verification mechanism according to various aspects will be made with exemplary reference to a fluid delivery system 10 having contrast as a first injection fluid 24 and saline as a second injection fluid 22. However, the basic discussion and operation of the fluid input verification mechanism disclosed herein could apply to other combinations of fluids as well, such as contrasts of different viscosities, contrast and air and/or vacuum, saline and air and/or vacuum, or air and vacuum.

By way of background, it is known that the viscosity of various contrast agents and the viscosity of saline may be very different, with the viscosity of most conventional contrast solutions being significantly more viscous, for example about 10 to 20 times that of saline. The viscosity of various contrasts also varies with the concentration and/or temperature of the contrast. It is also known that the viscosity of air is significantly lower than water. In addition, it is well recognized that, all other things being equal, the higher the viscosity, the greater the amount of pressure is required to move the fluid through a fluid path at a particular flow or fill rate. It is know that air generally behaves according to the idea gas law and that at relatively low gas concentrations or pressures, the negative pressure asymptotically approaches the negative of the surrounding air pressure. This is low, relatively constant negative pressure condition is commonly called a vacuum. It is against this general background that fluid input verification mechanism according to the present disclosure operates.

Referring back to FIG. 1, in certain aspects, the fluid input verification mechanism of the present disclosure may include one or more sensors 101 that measure the force and/or pressure required to draw fluid into syringe 14 and/or to expel fluid out of syringe 14. In one non-limiting embodiment, sensors 101 include one or more strain sensors associated with or in communication with the drive shaft of the injector 12 and/or in association with the internal structural frame of the injector 12. Such strain sensors may be incorporated into new injector configurations or integrated into existing injector designs, including those injectors discussed in various references incorporated herein. Strain sensors could also be configured to be associated with or in communication with another component of injector 12 that is involved in drawing fluid into the syringe 14 and/or expelling fluid out of syringe 14, such as those components that supply the power and/or force to actuate the plunger of syringe 14. The present disclosure also includes other possible configurations of strain sensors that operate consistent with the intended function discussed herein. The strain sensors can measure the force being applied by the drive shaft, or other component, to draw fluid into syringe 14 and/or to expel fluid out of syringe 14. Other possible types of sensors are envisioned, for example any sensor capable of measuring the force or pressure required to draw fluid into syringe 14 and/or to expel fluid out of syringe 14. For example, in-line pressure sensors 101 located in fluid input flow path 18 at or near the inlet/outlet to syringe 14, or within syringe 14 itself, may be used to measure the pressure applied within the fluid flow path 18 or within the syringe 14 while drawing fluid into syringe 14 and/or expelling fluid out of syringe 14.

In certain aspects, the fluid input verification mechanism can further include a processing unit 201 in electronic communication with sensors 101. Processing unit 201 is configured to receive measurements from sensors 101 and determine for example, based at least in part on the received information, whether the correct fluid is being drawn into syringe 14. In one non-limiting embodiment, processing unit 201 is configured as a component or module of fluid control module 20. However, processing unit 201 can be a stand-alone unit, such as a touch screen tablet computer connected to the system by a wireless connection, or can be integrated into another component of fluid delivery system 10, provided such component has sufficient computing power to accomplish the tasks required of processing unit 201.

Communication between sensors 101 and processing unit 201 can be accomplished using any suitable communication technique known in the art, including both wired and wireless (such as RF) communication. Short range RF communication techniques such as Bluetooth represent one non-limiting example. Sensors 101 may be configured to take measurements continuously or periodically while the syringe 14 is being loaded or when expelling fluid. Some or all of these measurements may be communicated to processing unit 201. In one non-limiting embodiment, sensors 101 continuously monitor and communicate to processing unit the retraction/extension force applied by the drive shaft while syringe 14 is being loaded/emptied. In other non-limiting embodiment, sensors 101 measure the retraction/injection force at one or more points in time after the fluid draw begins. As will become apparent below, it may only be necessary for sensors 101 to take and/or communicate measurements for a limited duration, or at limited points, of the syringe 14 loading/injection period.

Processing unit 201 can include one or more processors that may have stored thereon, or be in communication with, program instructions that, when executed by the processor, cause the processor to control the operation of processing unit 201. For example, the instructions, when executed, may allow processing unit 201 to determine whether the fluid being drawn into syringe 14 is the correct or expected fluid. This determination can be based, at least in part, on the force and/or pressure measurements taken by sensors 101. If processing unit 201 determines that the fluid being drawn into or expelled from syringe 14 is not correct, processing unit 201 can initiate an alert, flag, indicator, or other type of alarm to notify the operator of the discrepancy. Alarm can take on any readily perceptible form, and may include one or more of an audible component, a visual component, or a tactile component (for example on injector systems that utilize hand controlled injection protocols). In one non-limiting example, operator is notified that the fluid being drawn into or expelled from syringe 14 may be incorrect by a message rendered on a graphic user interface associated with fluid control module 20. Processing unit 201 can also automatically take an action to, for example, prevent further fluid draw into syringe 14 or stop an injection protocol by initiating a forced stop of the injector 12, such as by sending a signal to fluid control module 20 or directly to injector 12. A forced stop can allow the user an opportunity to assess the situation and correct the condition that caused the alarm.

Figure 4:
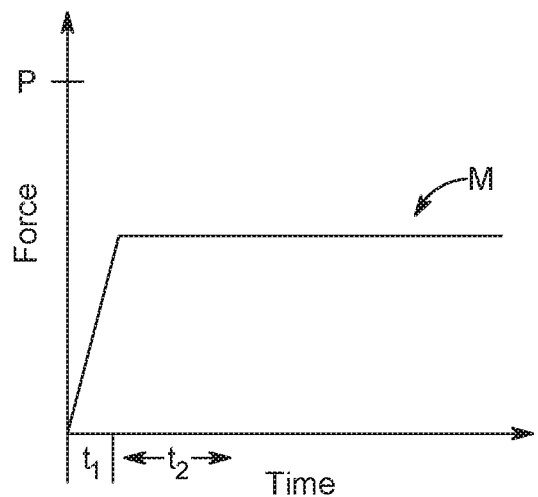
FIG. 4 illustrates a graph of the force required to load a syringe with a fluid as a function of time.
Figure 5:
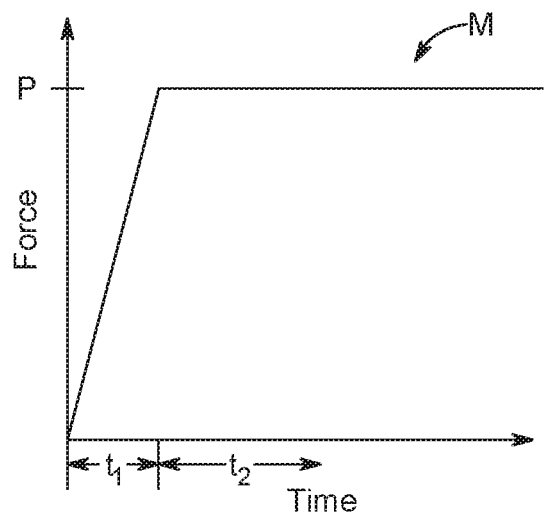
FIG. 5 illustrates graph of the force required to load a syringe with a fluid as a function of time.

A non-limiting embodiment of a process for verifying the fluid being drawn into syringe 14 according to one non-limiting embodiment is now described. This process can be embodied in programming instructions that are stored in memory associated with processing unit 201. Reference is made to FIGS. 4 and 5 to assist with the explanation of this process. FIG. 4 relates to a scenario in which the fluid being drawn into syringe 14 is determined to be incorrect, while FIG. 5 relates to a scenario in which the fluid being drawn is determined to be correct. It should be noted that in FIGS. 4 and 5, the fill pressure is the pressure difference between the contrast container and the interior of the syringe. The fill pressure is positive when the contrast container is at a higher pressure than the syringe, and thus fluid lows from the contrast container into the syringe. According to these examples, the syringe plunger is being pulled proximally and if the contrast container is at atmospheric pressure, there may be a negative pressure in the syringe compared to the atmospheric pressure. This may be understood as or called a reduced pressure, partial vacuum, or vacuum.

Once the fluid draw process begins, sensors 101 can begin taking measurements of the force or pressure required to draw fluid into syringe 14. At the onset of the fluid draw process, there will typically be an initial period of time to build up to the full force/pressure required to draw the fluid. This initial period is shown in FIGS. 4 and 5 as the steeply sloped line. This initial time period is denoted as $t_1$ in FIGS. 4 and 5. Sensor measurements during $t_1$ are not of particular importance, and sensor readings received by processing unit 201 during this initial stage may be ignored, or sensors 101 may be programmed to altogether avoid transmitting or taking measurements until time $t_1$ has elapsed. However, in some embodiments, the slope of this line and the time to reach steady state may be of value in determining whether the fluid being drawn into syringe 14 is correct. Eventually, the force/pressure required to draw fluid into syringe 14 will near steady state at which time the force measurement should remain fairly constant. This is denoted as $t_2$ in FIGS. 4 and 5. At least one, and preferably more than one, force measurement is taken during $t_2$ and communicated to processing unit 201.

Based on the data received from sensor 101, processing unit 201 determines whether the fluid being drawn is correct. As shown in FIG. 4, based on the particulars of the fluid input flow path 18 and the known viscosity of the fluid intended to be drawn into syringe 14, the force measurement is expected to reach a predetermined steady state value P. Thus, processing unit 201 is expecting to receive, from sensor 101, a force measurement that is at P or at least within a given tolerance of P after the elapse of $t_1$. As values are measured by sensor 101 and communicated to processing unit 201, processing unit compares those values with P and determines whether the actual values are within the requisite tolerance of P. This determination may involve processing unit 201 receiving and processing multiple force measurements over time, such as five measurements over the period of five seconds, in order to ensure consistency in the measurements and to guard against outliers in the data set. Processing unit 201 may also perform one or more calculations or transformations of the raw data received from sensors 101 as part of this comparison. For example, the raw data received from sensor 101 may be a measure of the force applied by the drive shaft of injector 12, and processing unit 201 may convert this to a measure of pressure within syringe 14 prior to performing the comparison with P.

If the measured force/pressure values received by processing unit 201 from sensors 101 are sufficiently different than P (such as outside of a tolerance range), processing unit 201 can trigger an alarm to alert the operator of the discrepancy and potentially stop further operation of the injector 12. For example, in FIG. 4, the measured force values, depicted with the line labeled M, does not reach P during $t_2$. This suggests that the fluid being drawn into syringe 14 is less viscous than expected. Such a result would be indicative of the scenario in which the fluid expected to be drawn into syringe 14 is contrast while the fluid actually being drawn into syringe 14 is saline or a diluted contrast. Based on this information, processing unit 201 can determine that the wrong fluid is being drawn into syringe 14. In response, processing unit 201 can issue an alarm and/or stop further fluid draw. On the other hand, in FIG. 5, the measured force values, again depicted with the line labeled M, reach the value P, suggesting that the fluid being drawn into syringe 14 is the correct fluid. Processing unit 201 does not issue an alarm in this scenario.

As will be appreciated, processing unit 201 must have knowledge of what force or pressure value is expected (i.e., P) for a particular syringe 14 loading cycle. Providing processing unit 201 with this knowledge can be accomplished in a variety of ways. In one embodiment, an operator can simply enter the expected value P directly into processing unit 201, such as by entering the value into a text box on an interface associated with processing unit 201. In another embodiment, processing unit 201, or a database with which processing unit 201 can communicate, can house information about the fluid input flow path 18, syringe 14, injector 12, and/or injection fluids 22, 24. Information about which fluid will be drawn at a given time can be entered into fluid control module 20 by an operator and communicated to processing unit 201. Processing unit 201 can then calculate an expected force or pressure value P based on some or all of this information. These calculations could also be performed in advance and stored in a database or other form of computer memory associated with processing unit 201. Information about a variety of different fluid input flow paths 18, syringes 14, injectors 12, and/or injection fluids 22, 24 can also be stored in memory associated with processing unit 201 for quick access should any of these aspects of fluid delivery system 10 change, such as if different fluids 24, 22 are used or if a different fluid input flow path 18 is used. Adjustments may also be needed to allow for greater tolerances depending on which components of fluid delivery system 10 are used, particularly if changes are made to the fluid input flow path 18, as the geometry and flow resistance of certain configurations of fluid delivery system 10 may yield more predictable results with less variation. In addition, time varying factors that affect fluid fill properties may be measured, accounted for, and/or input into the system 10. For example, in certain cases fluid temperature may affect viscosity. Therefore, if the fluid temperature is not known, a relatively larger tolerance on pressure may be allowed. Alternatively, the system may measure fluid temperature, for example with a thermocouple or solid state sensor, and therefore be able to use a narrower tolerance on acceptable pressure behavior. Alternatively, the user may indicate to the system whether the fluid is warmed or at room temperature, and optionally input the temperature of the fluid. Because user input may not be as reliable as measured fluid temperature, the acceptable pressure range may be intermediate in size, smaller than that needed with no temperature information but larger than that using actual temperature measurement.

The slope of the pressure change during the rising phase (the $t_1$ phase), or that time $t_1$ required to reach steady state pressure, may also be used to assess that the correct fluid is being filled or if at least a small volume of air or other gas is being drawn into the syringe. This can be especially useful if the fill process is chosen to be as fast as possible because, on a retraction of the syringe 14, the maximum pressure that can be achieved is typically one atmosphere. Thus, in that limiting condition, the pressure is not a function of the fluid. However, the fill rate at a given pressure less than one atmosphere is a function of the fluid. This mode may also be beneficial because it occurs at or near the beginning of the fill, and thus the alarm may be sounded or action may be taken earlier if conditions require it.

A third way to measure fluid properties during fill may be to assess the pullback rate or fill speed needed to create a fill pressure that is measurably less than one atmosphere. This can be done by assessing the pressure during the fill and adjusting, such as through the use of a servo mechanism and feedback data, the fill rate to maintain the desired filling pressure, for example at a substantially constant pressure.

A fourth way to measure the fill property may be to measure the time necessary to fill the syringe with a particular fluid at a given fill pressure P, pull back rate, and/or fill volume.

The expected pressure performance P may be assessed experimentally or theoretically, or both, using the known fluid path element dimensions and thus resistance to flow and the fluid properties, for example viscosity and/or temperature. In general, pressure is proportional to viscosity, flow rate, and fluid path resistance. With fluid path elements having directional symmetry, reversing the direction of fluid flow simply reverses the direction of the pressure drop. Thus, the assessments described herein for filling may also apply in the case of delivery when the fluid path is known.

Figure 6:
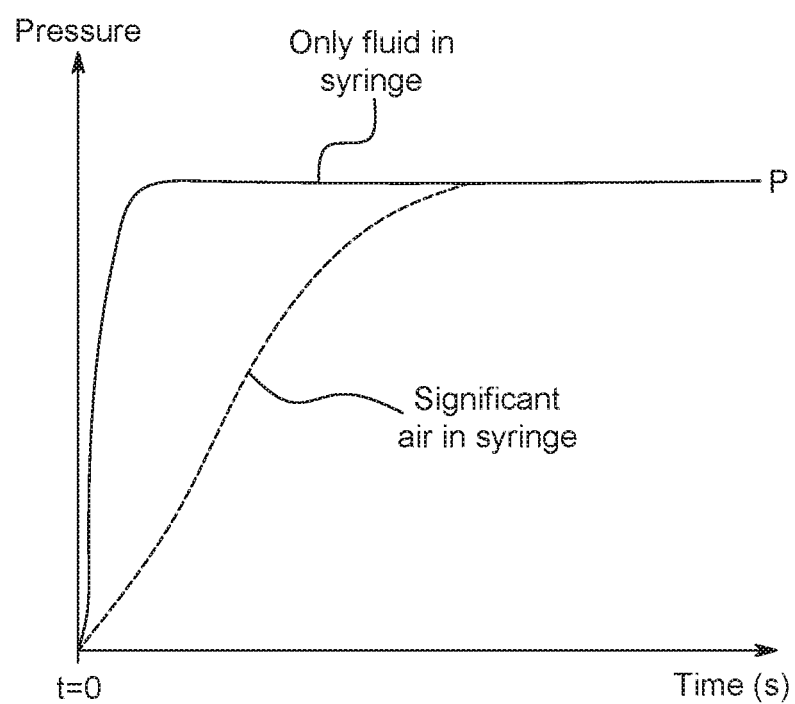
FIG. 6 illustrates a graph of the force applied to dispense the contents of a syringe as a function of time.

With reference to FIG. 6, during the fill cycle, if there is significant gas, for example air, in the recipient fluid path element and/or the syringe 14, the rise in the pressure difference will be more gradual because of the compressibility or expandability of the gas. The slowness, non-linearity, reduced maximum pressure achievable, and/or other differences in the pressure as compared with a completely liquid-filled syringe 14 may be sensed or detected by processing unit 201, resulting in an alarm or action if appropriate. This may be important because if there is sufficient air in the syringe, even if the air is removed before injection and thus the hazard to the patient is eliminated, the fill volume may be less than a desired or programmed fill volume due to the space occupied by the air, causing the desired procedure to be insufficiently completed without performing a further fill cycle. A further fill cycle may cause added time and inconvenience.

In addition, if air is introduced during the fill process, a transient and/or steady state dip in pressure may occur and be sensed, potentially indicating the emptying of the filling source or the introduction of an air leak in the system 10. In various aspects, this event may be detected by the fluid input mechanism and appropriate alarm or action may be taken by the system and/or operator.

In addition to, or alternatively to, the fluid input verification mechanism, fluid delivery system 10 may include a fluid output verification mechanism to verify that the fluid contained in syringe 14 that is set to be delivered to the patient is correct. According to aspects of the present disclosure, the fluid output verification mechanism may accomplish this, at least in part, by measuring the compressibility and/or viscosity of the fluid within syringe 14 (i.e., how compressible is the fluid within the syringe). In certain aspects, the fluid output verification mechanism has particular application in determining the presence, or absence, of air within syringe 14. Detection of air within syringe 14 is of particular importance given that an injection of air poses serious health risks to a patient.

The following operational discussion of an aspect of the fluid output verification mechanism will be made with exemplary reference to a syringe 14 containing an amount of saline or contrast and an amount of air. However, the basic discussion and operation of fluid output verification mechanism could apply to other combinations of materials within syringe 14 as well, and particularly to a combination of a gas, which is highly compressible, and a liquid, which is far less compressible.

By way of background, it is known that air is far more compressible than liquid. For example, the bulk modulus of air at room temperature is $\sim 1.42 \times 10^5$ Pa while that of water is $\sim 2.2 \times 10^9$ Pa, making air approximately 15,000 times as compressible as water at room temperature. Without intending to be limited by any theory, it is against this general background that the fluid output verification mechanism is believed to operate.

In certain aspects, the fluid output verification mechanism of the present disclosure may include one or more sensors 301 that can measure the force and/or pressure applied while dispensing (injecting) the contents of syringe 14, particularly at the onset of the injection. In one non-limiting embodiment, sensors 301 include one or more strain sensors associated with or in communication with the drive shaft and/or internal structural frame of the injector 12. Such strain sensors could be incorporated into new injector designs or integrated into existing injector designs, including those injectors discussed in the references that are incorporated herein. Strain sensors 301 could also be configured to be associated with or in communication with another component of injector 12 that is involved in dispensing the contents of syringe 14, such as those components that supply the power and/or force to actuate the plunger of syringe 14. Other possible configurations of strain sensors that operate consistent with the intended function discussed herein are within the scope of the present disclosure. The strain sensors can measure the force being applied by the drive shaft, or other component, to dispense the contents of syringe 14. Other possible types of sensors 301 are envisioned, so long as sensors 301 are capable of measuring the force or pressure required to dispense the syringe contents, for example at the onset of the injection. For example, in-line pressure sensors like those described herein located within syringe 14 may be used to measure the pressure within the fluid flow path 18 or within syringe 14 during the injection. In certain embodiments, sensors 301 may include at least some of the same sensors 101 that are used in the fluid input verification mechanism, and the same sensor can act as both sensor 301 and sensor 101. In various aspects sensors 301 that are highly accurate and sensitive so that slight variations in pressure over time can be detected. Alternatively, sensor 301 may alternatively measure motor current to estimate or determine the force on the system and/or the pressure in the syringe 14.

In various aspects, the fluid output verification mechanism further includes a processing unit 401 in electronic communication with sensors 301. Processing unit 401 is configured to receive measurements from sensors 301 and detect, based at least in part on the received information, the presence of air within syringe 14. Processing unit 401 can be configured similarly to processing unit 201, discussed above. In one non-limiting embodiment, processing unit 401 is configured as a component or module of fluid control module 20. Processing unit 401 and processing unit 201 (discussed above) may even be one in the same. However, processing unit 401 can also be a stand-alone unit or can be integrated into another component of fluid delivery system 10, provided such component has sufficient computing power to accomplish the tasks required of processing unit 401. Communication between sensors 301 and processing unit 401 can be accomplished using any suitable communication technique known in the art, including both wired and wireless (such as RF) communication. Short range RF communication means such as Bluetooth represent one non-limiting example. Sensors 301 may be configured to take measurements continuously or periodically while the syringe 14 contents are being dispensed. Some or all of these measurements may be communicated to processing unit 401. In one non-limiting aspect, sensors 301 continuously monitor and communicate to processing unit 401 the force applied to dispense the contents of syringe 14. As will become apparent below, it may only be necessary for sensors 301 to take and/or communicate measurements for a limited duration of the dispensing process, and particularly at the onset thereof. Optionally, sensors 301 may monitor the whole delivery process and thus be used to check for other situations such as unanticipated or incorrect fluids or fluid leaks via analysis of force and/or pressure changes.

Processing unit 401 can include a processor programmed with a set of computer-readable operating instructions that, when executed, allow processing unit 401 to determine the presence of air within syringe 14. This determination is based, at least in part, on the force and/or pressure measurements taken by sensors 401. If processing unit 401 determines that the syringe 14 includes air, processing unit 401 can initiate an alert, flag, indicator, or other alarm to notify the operator. Alarm can take on any readily perceptible form, and may include an audible component, a visual component, or both. In one non-limiting example, operator is notified of the presence of air by a message rendered on a graphic user interface associated with fluid control module 20. Processing unit 401 can also automatically prevent any further dispensing of the syringe contents by initiating a forced stop of the injector 12 and other equipment (e.g., a scanner), such as by sending a signal to fluid control module 20 or directly to injector 12. Alternatively, in certain embodiments, the system may perform an automatic prime operation to purge air out of the syringe and fluid line. Such automated prime operation would then recheck the system to confirm elimination of air by using the fluid output verification mechanism.

A non-limiting embodiment of a process for verifying the contents of syringe 14 according to one non-limiting embodiment is now described. This process can be embodied in programming logic that is incorporated into processing unit 401. Reference is made to FIG. 6 to assist with the explanation of this process.

At the onset of the injection, an initial force is required to overcome the friction of the plunger/piston against the syringe interior wall and start movement of the plunger/piston. Once movement begins, there is a period of time to build up to the steady state injection pressure. The steady state injection pressure is depicted as P in FIG. 6. The time to reach P is referred to herein as the onset period, and the rate of pressure change during the onset period is depicted in FIG. 6 as the sloped lines beginning near time=0 (t=0). In an exemplary syringe programmed to deliver 4-5 ml/s at a piston speed of 2 mm/s and a steady state pressure of 200 psi, the onset period to reach full pressure is about 2 seconds assuming very little air is present in the syringe. The rate at which the pressure rises during the onset period is dependent on the compressibility of the contents of the fluid path and the stiffness or flexibility of syringe 14, other fluid elements, and mounting system. For example, since air is highly compressible, the pressure rise (change in pressure over time) during the onset period will be slower if the syringe contains a significant amount of air, as shown by the dashed line in FIG. 6. On the other hand, if syringe 14 includes liquid only (or only trace amounts of air) the pressure within syringe 14 will rise much faster, as shown by the solid line in FIG. 6, since liquid is far less compressible than air. Comparison of the slope of the line during the onset period may provide data as to the presence of air and may even allow calculation of the volume of air present in the syringe.

During the onset period, sensors 301 measure the force or pressure applied to dispense the contents of syringe 14 and communicate these measurements to processing unit 401. Based on the data received from sensor 301, processing unit 401 can detect the presence of air within syringe 14. As shown in FIG. 6, if syringe 14 contains only fluid, the pressure is expected to sharply increase during the onset period. Thus, the measurements received by processing unit 401 during the onset period are expected to reflect a rapid pressure rise. As values are measured by sensor 301 and communicated to processing unit 401, processing unit 401 can compare the actual pressure measurements to an expected pressure at a given time for a given fluid to determine whether the pressure rise is indicative of a syringe 14 containing only fluid. For example, processing unit 401 can compare the actual pressure measurement for a fluid after one second to an expected pressure measurement for that fluid after one second, given a specific applied pressure to the plunger by the piston. If the actual pressure after one second is not within a certain tolerance of the expected pressure at that time, and particularly if the actual pressure is far less than expected, this suggests that syringe 14 contains a significant amount of air. By way of another example, processing unit 401 can also, or alternatively, compare consecutive pressure measurements, such as a series of measurements taken over a two second interval, to one another to determine the rate of pressure rise (change in pressure over time, shown by the slope of the line). Processing unit 401 can compare the measured rate of pressure rise with an expected rate of pressure rise for a fluid. If the actual rate of pressure rise is less than expected, this would suggest that syringe 14 contains a significant amount of air. If, through any calculation method, processing unit 401 determines that syringe 14 contains an unsafe amount of air, processing unit 401 can issue an alarm and/or stop the injector 12, preventing a dangerous amount of air from being injected into patient. If the data received from sensors 301 does not suggest that air is present or that the amount of air is far less than a threshold amount determined to be unsafe, no alarm activity is required of processing unit 401. Processing unit 401 may also account for the initial force required to overcome plunger stiction (static or breakaway friction) by disregarding any initial spike in the pressure that occurs immediately upon the initiation of the injection. In other embodiments, the processing unit 401 may account for capacitance (swelling due to increasing pressure of a contained fluid) of the syringe and/or fluid path during onset of injection and incorporate that into the calculation.

As will be appreciated, processing unit 401 should have knowledge of what force or pressure value is expected for a fluid of specific viscosity at various times throughout the onset period. In one embodiment, processing unit 401, or a database with which processing unit 401 can communicate, can house information about the performance of syringe 14, other fluid path elements, and injector 12 during the onset period, including a plot or table of the expected pressures at various times during the onset period. Processing unit 401 can then reference this information to determine whether the actual pressure rise is indicative of a syringe containing substantial amounts of air or only fluid.

Figure 7:
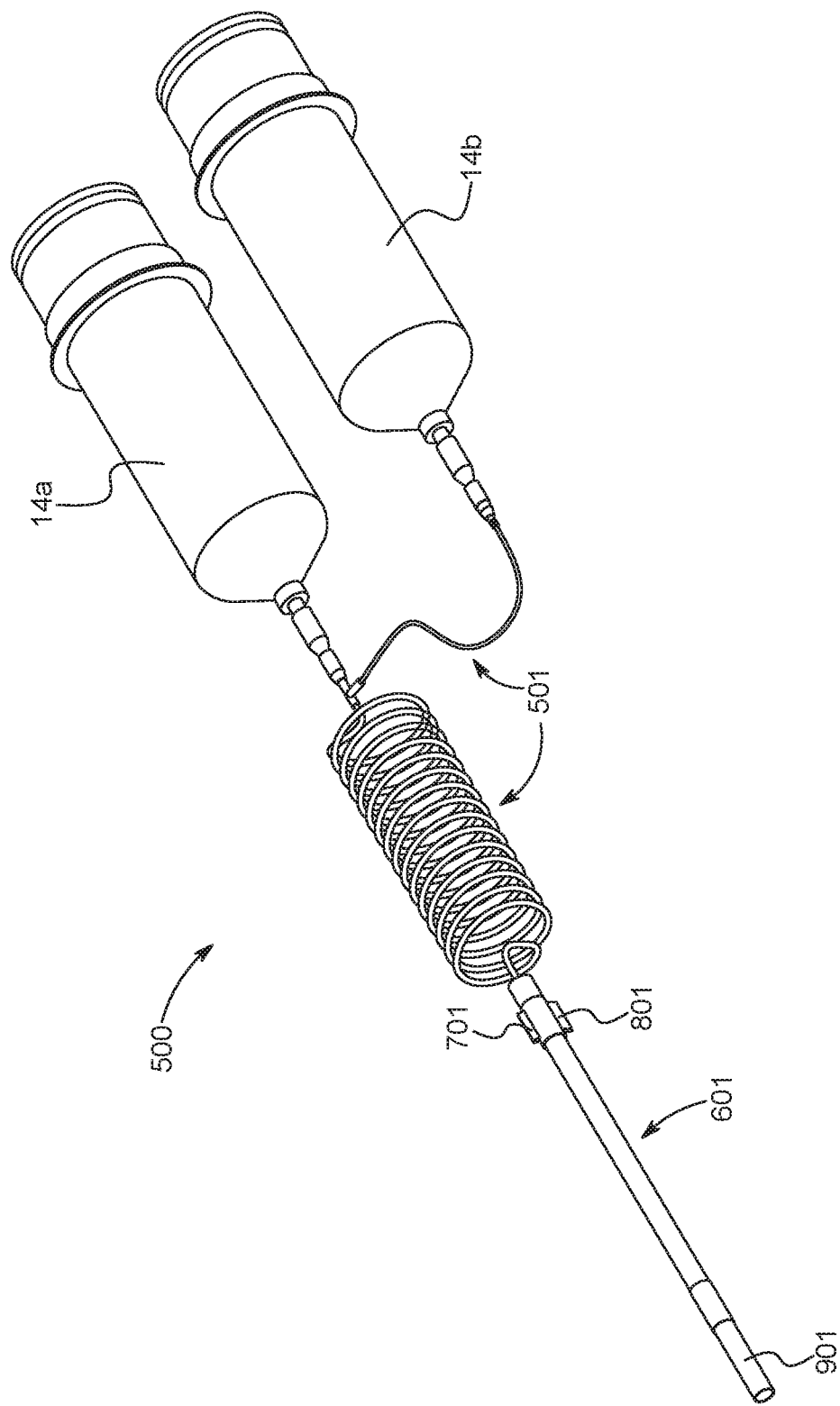
FIG. 7 is a perspective view of a single-patient disposable set for use in a fluid delivery system in accordance with another embodiment.
Figure 8:
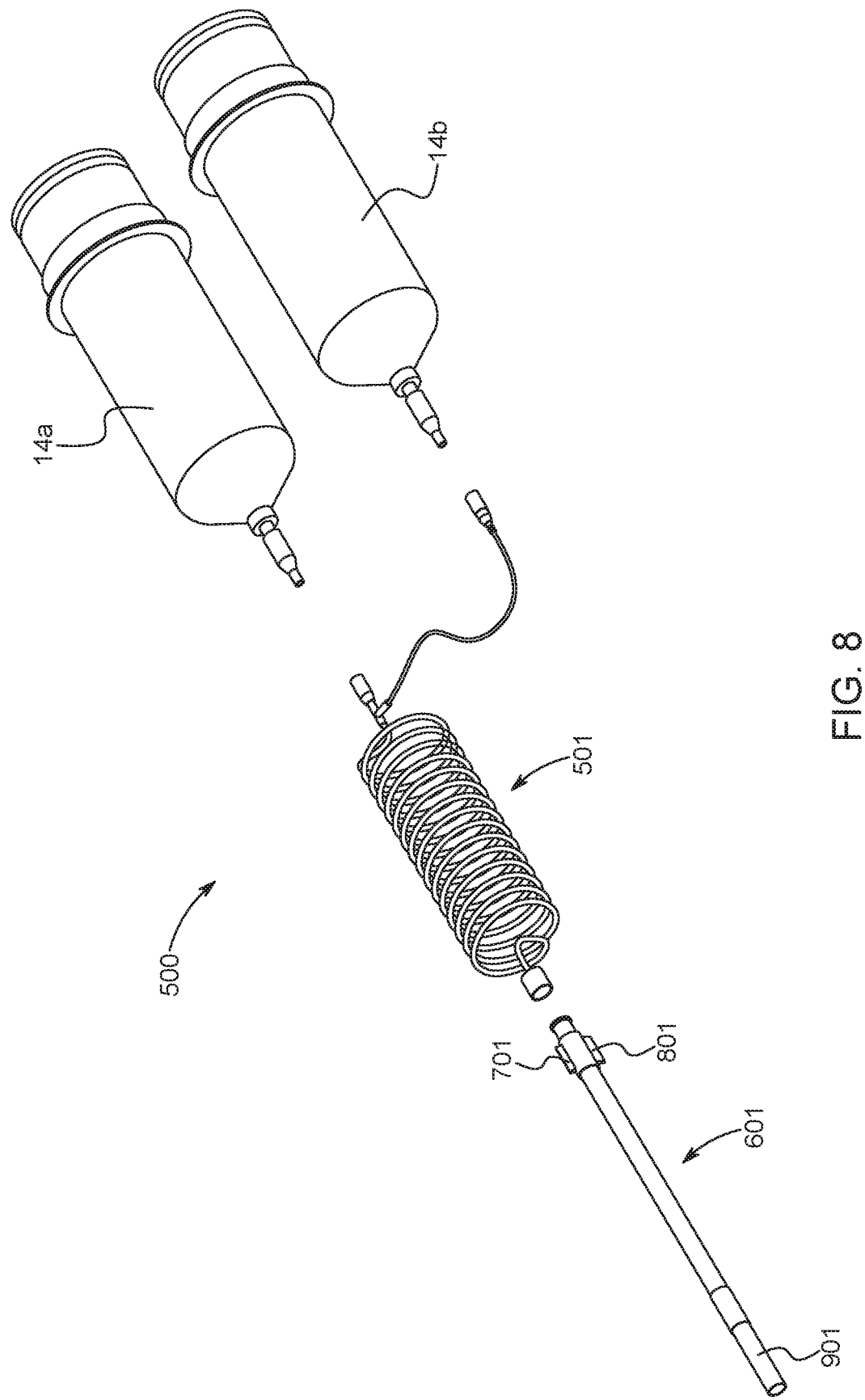
FIG. 8 is an exploded perspective view of the disposable set of FIG. 7.

A variation of the embodiments of the fluid output verification mechanism is depicted in FIGS. 7-8. With reference to FIGS. 7-8, a fluid path set 500 comprised of syringes 14a, 14b, and additional fluid path elements, such as connector tube 501, and purge tube 601 is shown. Connector tube 501 and purge tube 601 together create a fluid path between syringes 14a, 14b and the proximal end of purge tube 601. Purge tube 601 is depicted as including a luer 701 near the proximal end of purge tube 601, a flow restrictor 801 also near the proximal end of purge tube 601, such as within luer 701, and a filter or absorbent material 901 near the distal end of purge tube 601. The fluid path set 500 depicted in FIGS. 7-8 can be incorporated into a fluid delivery system 10 that includes additional components such as sensors, a processing unit, and an injector consistent with the description above. Processing unit can include a processor programmed with a set of computer-readable operating instructions that, when executed, can detect the presence of air within the syringe 14a, 14b, connector tube 501 and/or purge tube 601, as described below.

Luer 701 is designed to connect purge tube 601 to connector tube 501. In one embodiment, luer 701 is a female luer. Luer 701 engages with purge tube 601 to provide a secure connection between purge tube 601 and connector tube 501 and helps prevent purge tube 601 from disengaging with connector tube 501 during an air purge sequence or other operation that generates a pressure increase at the point of connection between purge tube 601 and connector tube 501. Purge tube 601 may be provided pre-attached to connector tube 501 to help ensure the fluid path remains sterile and for ease of use. Purge tube 601 may alternatively be connected to connector tube by a friction fit, though a locking mechanism such as luer 701 that provides a more secure connection.

Flow restrictor 801 is positioned within purge tube 601 and restricts the fluid flow through the purge tube 601, thereby, increasing the fluid pressure within purge tube 601 at points upstream of the flow restrictor 801. Non-limiting examples of flow restrictor 801 include a valve, filter, or small hole in the luer 701 or fluid path. In FIG. 8, flow restrictor 801 is positioned within luer 701, though flow restrictor 801 can be disposed anywhere within purge tube 601, or optionally at a known point elsewhere in the fluid path. In certain embodiments, flow restrictor 801 is positioned near the proximal end of the purge tube 601 where the connection tube 501 transitions to the purge tube 601.

Filter 901 is positioned within purge tube 601 near the distal end of purge tube 601. Between filter 901 and flow restrictor 801 is a length of purge tube 601 that can contain a volume of fluid. Filter 901 serves the purpose of preventing fluid contained in this length from dripping from the distal end of purge tube 601 when purge tube 601 is disconnected from connector tube 501. In certain embodiments, filter 901 may serve as flow restrictor 801.

Figure 9:
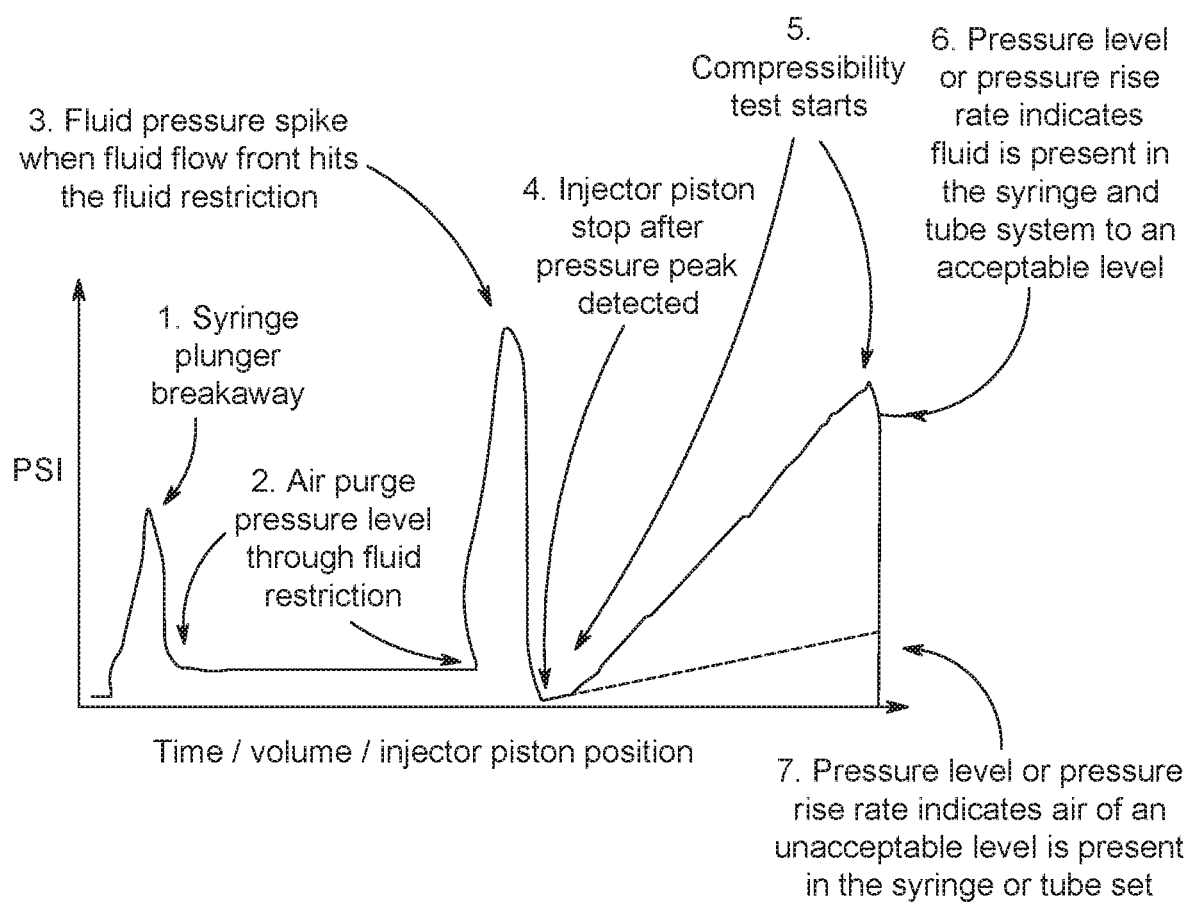
FIG. 9 illustrates a graph of the pressure applied to pass the contents of a syringe through a fluid restrictor as a function of time in accordance with an embodiment of FIG. 7.

According to embodiments of the fluid output verification mechanism, by measuring the changes in pressure being applied to pass fluid through the fluid path set 500 and past the flow restrictor 801, the presence of air in the connector tube 501 and syringe 14a, 14b can be detected according to various aspects herein. In addition, by monitoring pressure during an air purge sequence in which air contained in fluid path set 500 is purged to ready the syringe for injection of a fluid to a patient, the completion of an air purge process can be detected. A non-limiting description of the operation is now described. This process can be embodied in programming instructions that are incorporated into a processing unit associated with fluid output verification mechanism. Reference is made to FIG. 9 to assist with the explanation of this process.

In this embodiment, fluid path set 500 is incorporated into a fluid delivery system 10 that includes an injector for controlling the delivery of fluid from syringes 14a, 14b. The pressure applied to pass fluid through the fluid path set 500 can be determined by detecting changes in the measurements from a strain gage or motor current servo of the injector via one or more sensors, similar to those sensors described herein. However in other embodiments, the pressure could be measured using alternative arrangements as well, such as an inline sensor positioned to measure pressure at one or more known points in the syringe and/or fluid path, for example, distal to the flow restrictor 801, such as within purge tube 601 near flow restrictor 801.

First, the operation during an air purge sequence will be described, which generally precedes the injection of a fluid from syringe 14a, 14b to a patient. At the onset of the air purge sequence, an initial force is required to overcome the striction of the plunger/piston and start movement of the plunger/piston. This is represented in FIG. 9 as the "Syringe plunger breakaway" peak. Once movement begins, there will be a period of time necessary to purge the air from connector tube 501. This is represented in FIG. 9 as "Air purge pressure level through fluid restriction" portion. During this time period, liquid should be filling the line and air is passing through the flow restrictor 801. Because air is highly compressible and has a much lower viscosity than water or contrast, the pressure required to force air through flow restrictor 801 is relatively low. Once the air has been purged, a front surface of the liquid contained in syringe 14a, 14b will reach flow restrictor 801. Because liquid is less compressible and more viscous than air, the liquid front will generate a spike in the pressure when it reaches the flow restrictor 801 depicted in FIG. 9 at point 3. Once this pressure spike is detected, the air purge sequence can be considered complete and the injector is ready to inject the liquid to a patient. At this time, injector piston can be automatically or manually instructed to stop, as depicted in FIG. 9.

Once the purge sequence is complete, a compressibility test can be performed to ensure that no detectable or unacceptable amount of air remains in the connector tube 501 and/or syringes 14a, 14b. The compressibility test begins by performing a very slow rate, small volume injection of liquid through the flow restrictor 801 while the purge tube 601 is still connected. Because of the low compressibility of liquid, the passage of liquid through flow restrictor 801 will cause a steep rise in pressure over time. During the compressibility test, the pressure is monitored over time to determine the rate of pressure rise. The measured pressure and time values are used to calculate a measured pressure rise for the given liquid that is then be compared to an expected pressure rise for the given liquid to determine whether the measured pressure rise is within a set tolerance of the expected pressure rise. If the measured pressure rise is within the acceptable tolerance range, then it can be concluded that little to no air remains. This is depicted as the solid line in FIG. 9 between point 5 and point 6. On the other hand, if the measured pressure rise is outside the acceptable tolerance range, then it can be concluded that an unacceptable amount of air remains in the connector tube 501 and/or syringe 14a, 14b. Particularly, a measured pressure rise that is far below the expected pressure rise indicates that a more compressible material, like air, is being passed through the flow restrictor 801. This is depicted in FIG. 9 with the dashed line beginning after point 5. Rather than measuring the pressure rise and comparing it to an expected pressure rise value, the compressibility test can also (or alternatively) involve measuring the pressure at set points in time and then comparing the measured pressure value with an expected pressure value for the liquid at that point. Multiple pressure measurements at multiple time points can be utilized.

Following a successful result from the compressibility test indicating little or no air in the fluid path and/or syringe, the purge tube 501 can be removed. Because the purge tube 501 is capable of holding an amount of fluid between the proximal and distal ends, as described above, the fluid that is passed through the flow restrictor 801 during the compressibility test can preferably be held within purge tube 501. The purge tube 501 may then be discarded. The purge tube 501 may also be any other fluid receptacle, or the fluid beyond the flow restrictor 801 may be discharged into a separate waste receptacle or other vessel provided by the user.

Like with previously-described embodiments, various embodiments can have associated with it a processing unit programmed with a set of computer-readable operating instructions, one or more databases housing information about the expected pressure rise or pressure versus time values for various system components and injection fluids and temperatures, and an alarm unit programmed to alert an operator of any discrepancies between the measured and the expected pressure values as this would be indicative of the presence of air within the fluid path. Similarly, pressure measurements can be taken continuously or periodically during the relevant time periods. The aforementioned design could allow an auto purge to be used with any length of purge tube 601 and/or connector tube 501. Implementations of this concept should take into account all disposable system compliance and changes over manufacturing processes, sterilization, and time that could affect the expected or measured pressure values. Such changes can be addressed by updating the associated database or databases to include the updated information.

Figure 10:
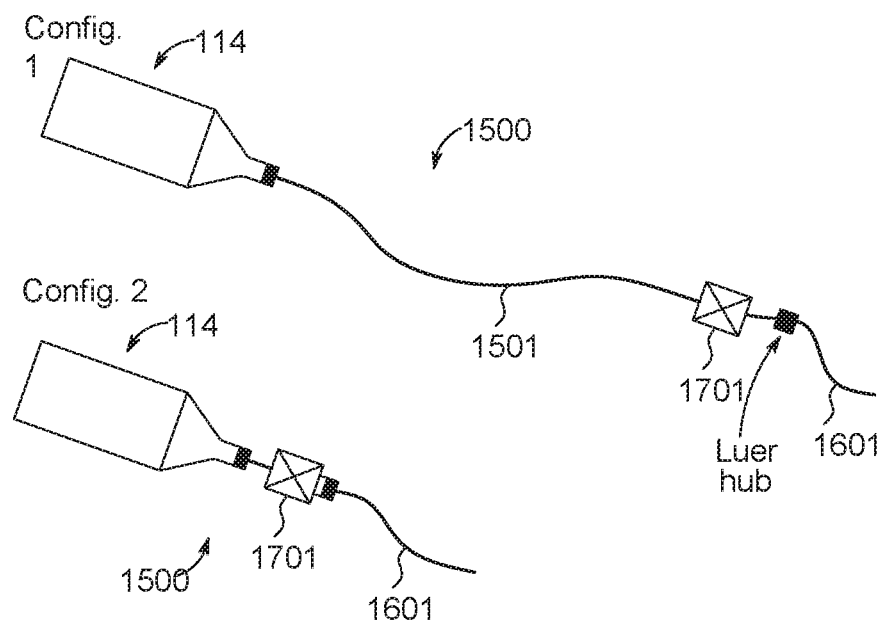
FIG. 10 is a perspective view of a fluid delivery system according to another embodiment.
Figure 11:
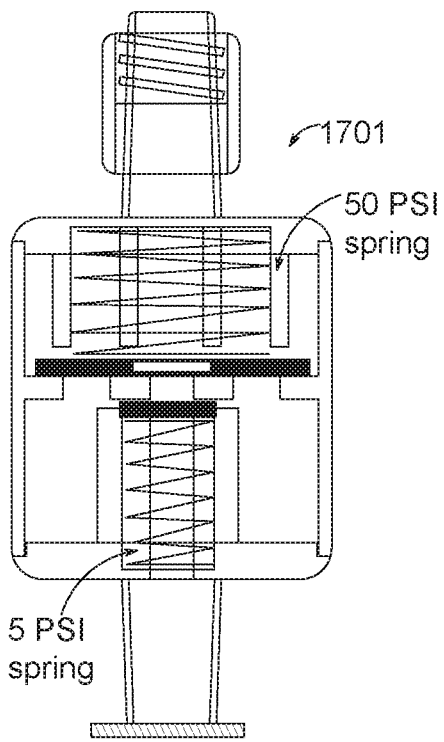
FIG. 11 is a cross-sectional view of an inline pressure valve according to one embodiment.

Another variation of the fluid output verification mechanism is depicted in FIG. 10. With reference to the first configuration of FIG. 10, a fluid path set 1500 comprised of syringes 114, connector tube 1501, and catheter tube 1601 is shown. Connector tube 1501 and catheter tube 1601 together create a fluid path between syringes 114 and the proximal end of catheter tube 1601. With reference to the configuration 2 of FIG. 10, no connector tube 1501 is present in fluid path set 1500. Fluid path set 1500 is depicted as including an inline valve 1701. The fluid path set 1500 depicted in FIG. 10 can be incorporated into a fluid delivery system that includes additional components such as sensors, a processing unit, and an injector consistent with the description herein. Processing unit can include a processor programmed with a set of computer-readable operating instructions that can be used to detect the presence of air within the syringe 114 or connector tube 1501, as described below. In certain embodiments, inline valve 1701 may be made from relatively inexpensive materials so that it can be disposable.

In addition, as discussed below, inline valve 1701 may be configured such that the valve remains in a closed position, preventing the fluid present in syringe 114 and connector tube 1501 from passing into catheter tube 1601 until a certain pressure threshold, or "trip pressure," is exceeded. Examples of similar valves are described in WO 2014/144651, the disclosure of which is incorporated herein by reference. Consistent with the principles discussed herein, pressure will build against inline valve 1701 quicker and reach a higher value if the connector tube 1501 and other portions upstream of inline valve 1701 are filled with an incompressible fluid such as a liquid, for example a contrast agent or saline, than if the connector tube 1501 or other portions upstream of inline valve 1701 is filled partially or completely with air.

Figure 12:
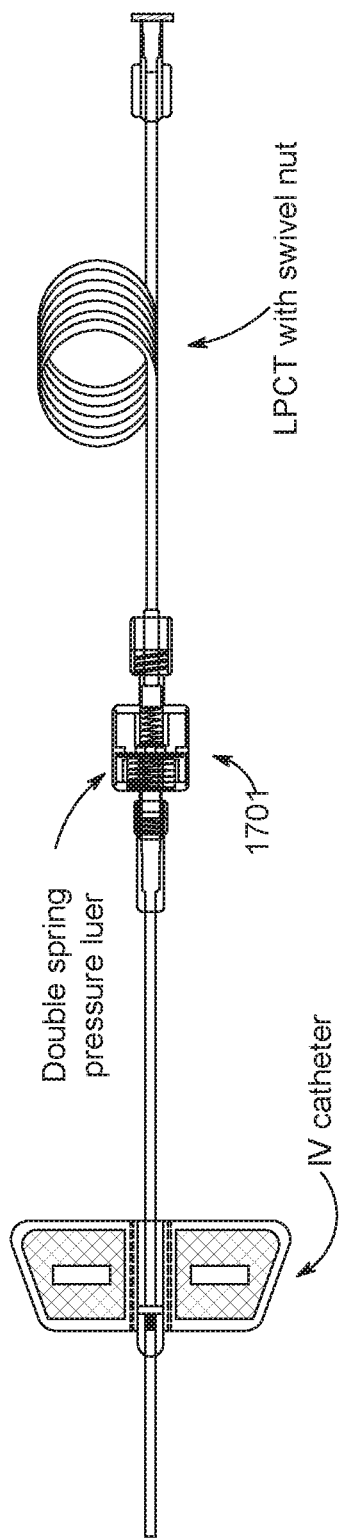
FIG. 12 is a schematic view of a fluid path set including the inline pressure valve of FIG. 11 according to one embodiment.
Figure 13:
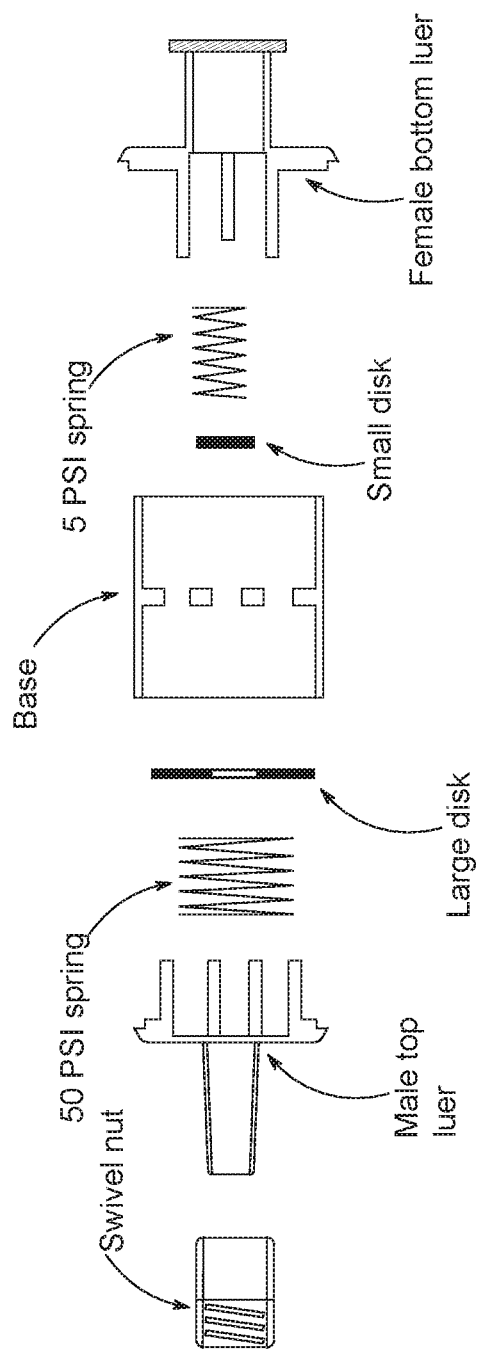
FIG. 13 is an exploded view of the inline pressure valve of FIG. 11.
Figure 14:
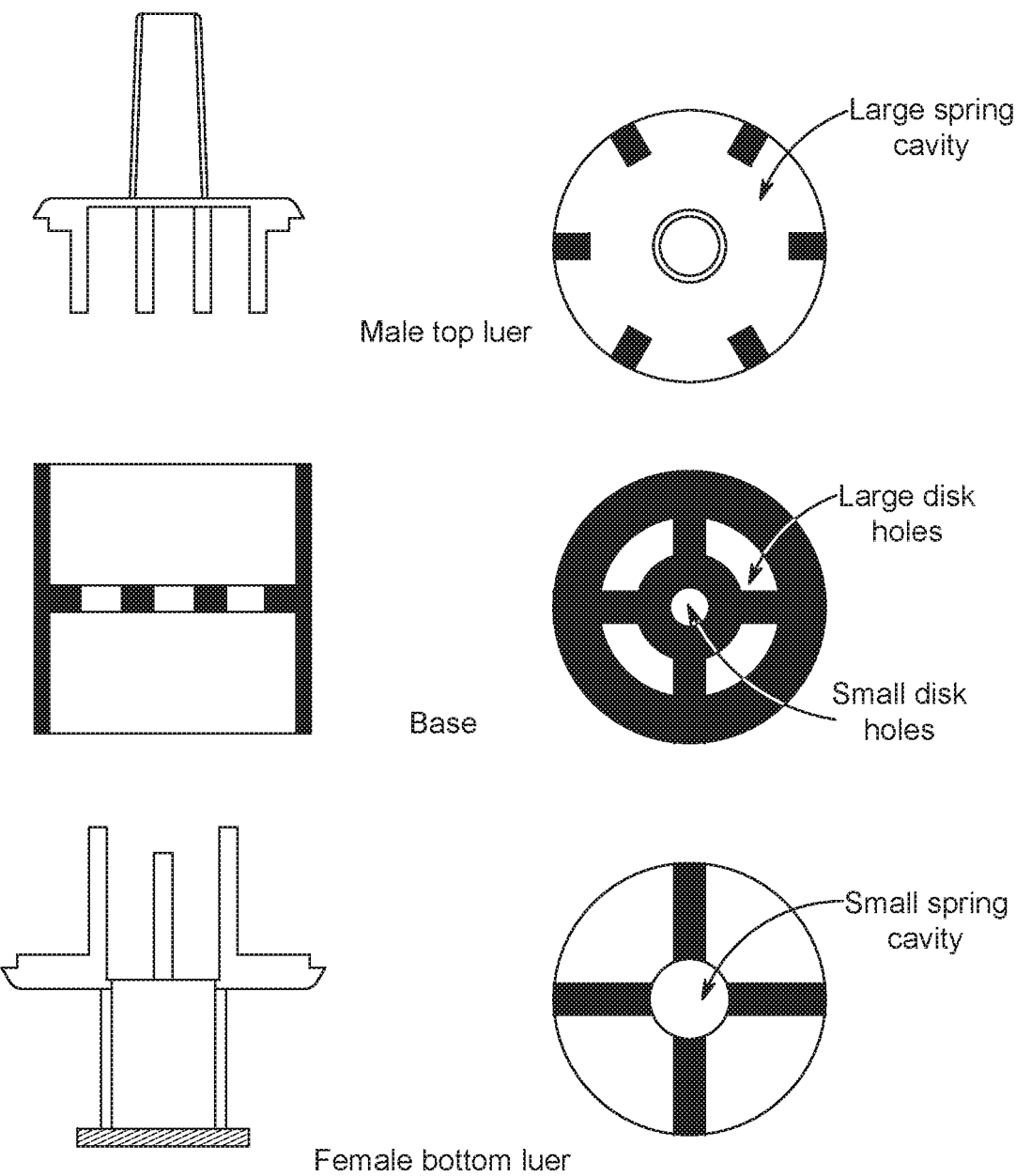
FIG. 14 is an exploded view of certain components of the inline pressure valve of FIG. 11.

In one non-limiting embodiment, inline valve 1701 is a spring-actuated pressure luer as depicted in FIGS. 11-14. The spring-actuated pressure luer can be disposed inline between, for example, a low pressure connecting tube (LPCT) equipped with a swivel nut and a catheter tube. One such embodiment, shown in FIG. 12, is a two-way (bidirectional), double spring pressure luer. With reference to FIGS. 13-14, the double spring pressure luer can include a swivel nut to connect the double spring pressure luer to the LPCT, a male top luer, a first spring, a large disk, a base, a small disk, a second spring, and a female bottom luer. The first spring can be rated at, for example, 50 psi and serves to regulate the injection pressure. In other words, an injection pressure of at least 50 psi is required to open the valve and allow the fluid to flow from the LPCT to the catheter. Springs having other injection pressure ratings as required for specific injection procedures can be used as well consistent with the scope of this disclosure. The rating of the spring to be used in terms of psi is determined based on, among other factors, the size of the tube, the compressibility of the fluid passing through the tube, and the minimum desired injection pressure. The second spring can be rated at, for example, 5 psi and serves to regulate the pullback pressure. The rating of the second spring, like that of the first, can be varied. Another embodiment of the spring-actuated pressure luer may be a single spring pressure luer which includes only the first spring but not the second spring. In such an embodiment, only the injection pressure is regulated by the pressure luer. In yet another non-limiting embodiment, the spring-actuated pressure luer can include a latch that engages once the valve is open due to the trip pressure being obtained, to retain the valve in an open position during the injection regardless of whether the necessary pressure is applied to the valve. Such a feature will lessen the load on the motor associated with an electronic injector.

If the fluid path set 1500 is to be disconnected from the patient prior to retracting the plunger, the system may remain pressurized, resulting in the release of the contents of the fluid path set 1500 once it is removed. This effect can be avoided by depressurizing the fluid path set 1500. This can be done by, for example, allowing the piston to automatically reverse at the end of the injection to an extent sufficient to close the valve; including the aforementioned latch in the valve that maintains the valve in the open position after initial pressurization; providing a small leak through the valve to slowly release pressure; and configuring the valve so that it includes a pressure release mechanism to permit pressure to be released when the valve is manually squeezed or turned.

As an alternative to the inline valve 1701 described herein, a pinch valve can be used. The pinch valve can be disposed on the outside of the connector tube 1501. Pinch valve can apply a pressure to the connector tube 1501, closing the tube by pinching the inner wall of the tube against itself until a sufficient pressure is applied from within the tube to overcome the pinching force applied by the pinch valve. The pinch valve works on the same principles discussed herein. For example, pinch valve can apply a pressure of 50 psi to the connector tube 1501. Only once this 50 psi trip pressure is overcome will fluid be allowed to flow past the location of the pinch valve. If the pressure is not overcome in a sufficient amount of time from the onset of the injection, an operator can be notified. At the end of the injection, a user can manually open the pinch valve to relieve pressure. Alternatively, the inline valve 1701 may be a stopcock which is switched between an open and a closed position. This may be user activated or may be controlled via a connection (not shown) to the fluid injector controller, for example processing unit 401.

As discussed herein, various embodiments of the fluid output verification mechanism can include a processing unit 401 configured to receive measurements from sensors and detect, based at least in part on received information, the presence of air within syringe 14, 14a, 14b, and/or 114. Processing unit 401 can include a processor programmed with a set of computer-readable operating instructions that, when executed, allow processing unit 401 to determine presence of air within syringe 14, 14a, 14b, and/or 114.

In one non-limiting embodiment, processing unit 401 can execute a detection algorithm developed through a curve fitting approach to determine if the volume of air within the syringe 14, 14a, 14b, or 114 is beyond a predetermined limit, and prevent the injection from proceeding if this limit is exceeded. The algorithm can be based on the least squares method to determine the coefficients for an equation that describes the relationship between volume displaced and pressure. The coefficients can represent initial volume, amount of air, pressure due to friction, and stiffness. The coefficients can then be compared to one or more thresholds to determine if air is or is not present in the syringe 14, 14a, 14b, or 114. A non-limiting example of the manner in which such a curve fitting algorithm can be developed is presented herein.

Figure 15:
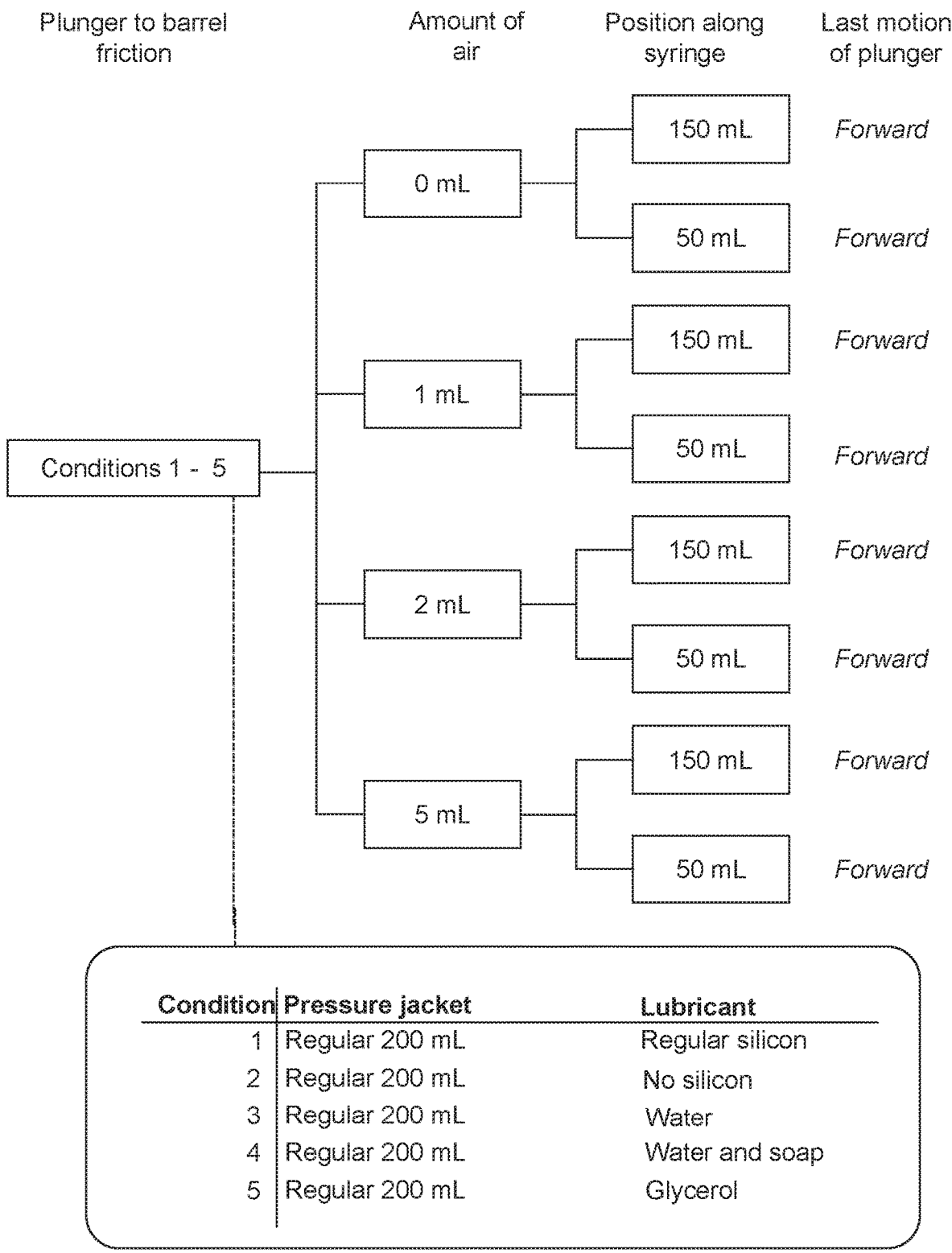
FIG. 15 is a summary of test conditions performed as part of a bench test.
Figure 16A:
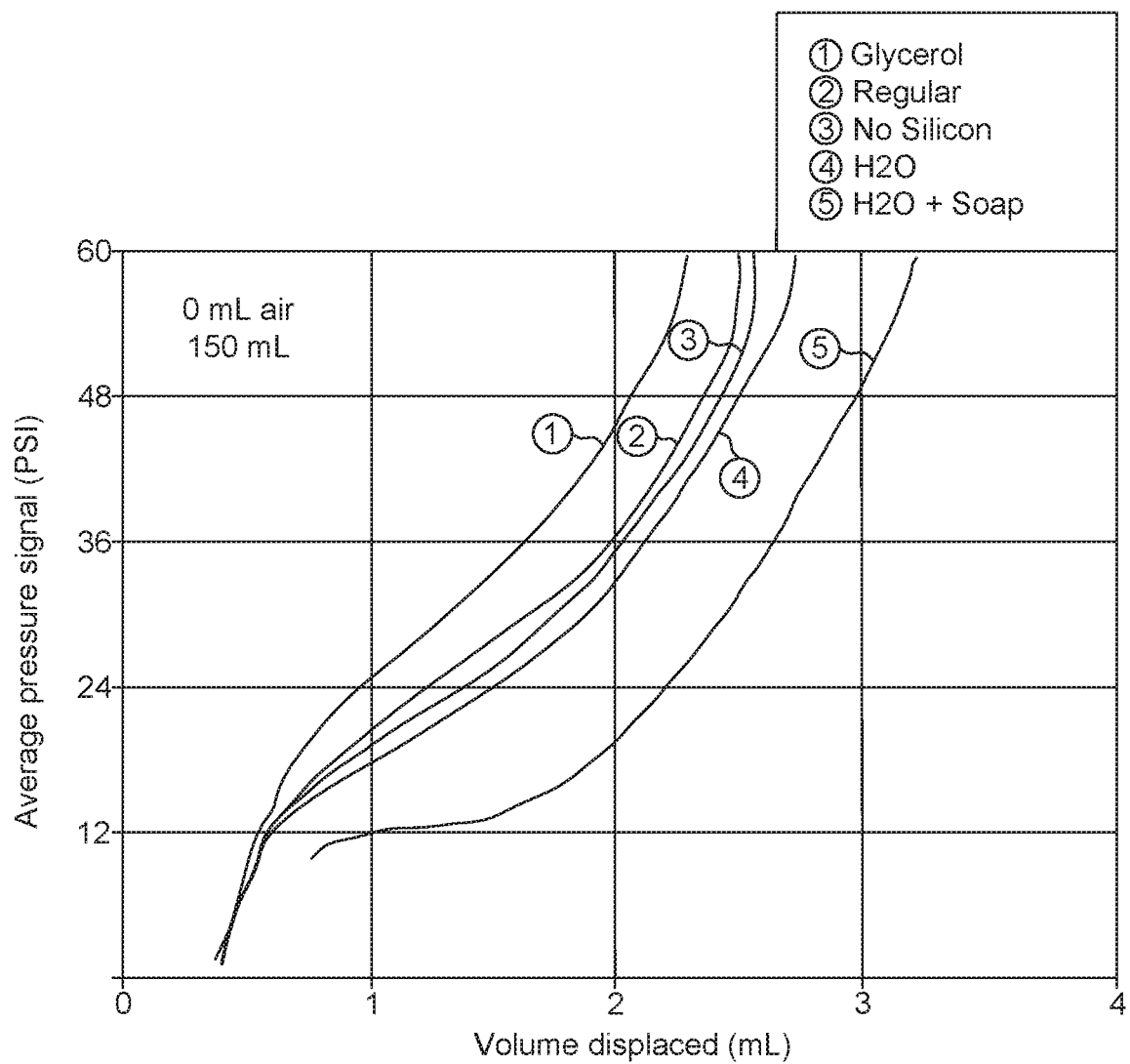
FIGS. 16A-16D illustrate graphs of the average pressure required to dispense the contents of a syringe as a function of the syringe volume displaced.
Figure 16B:
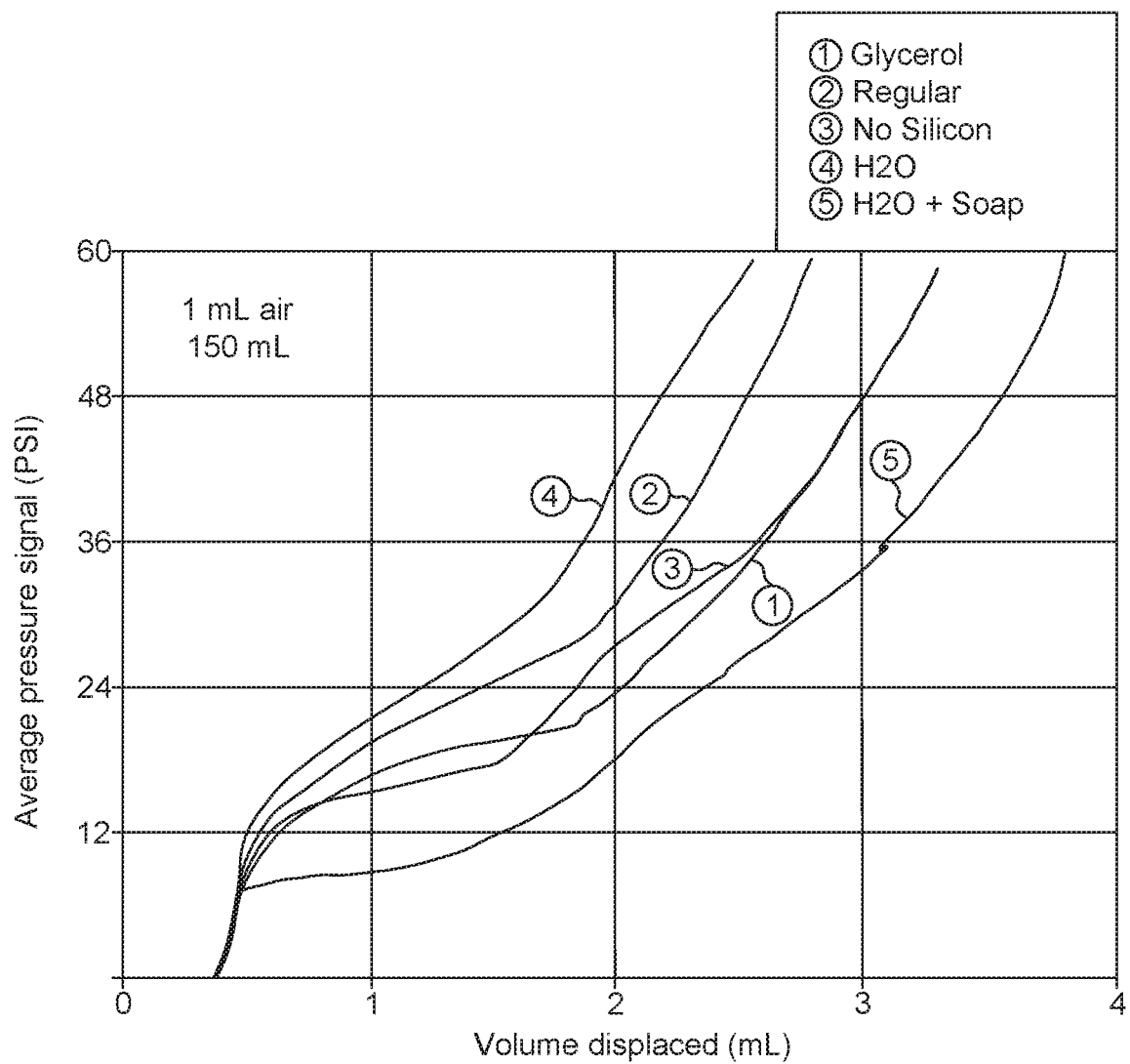
Figure 16C:
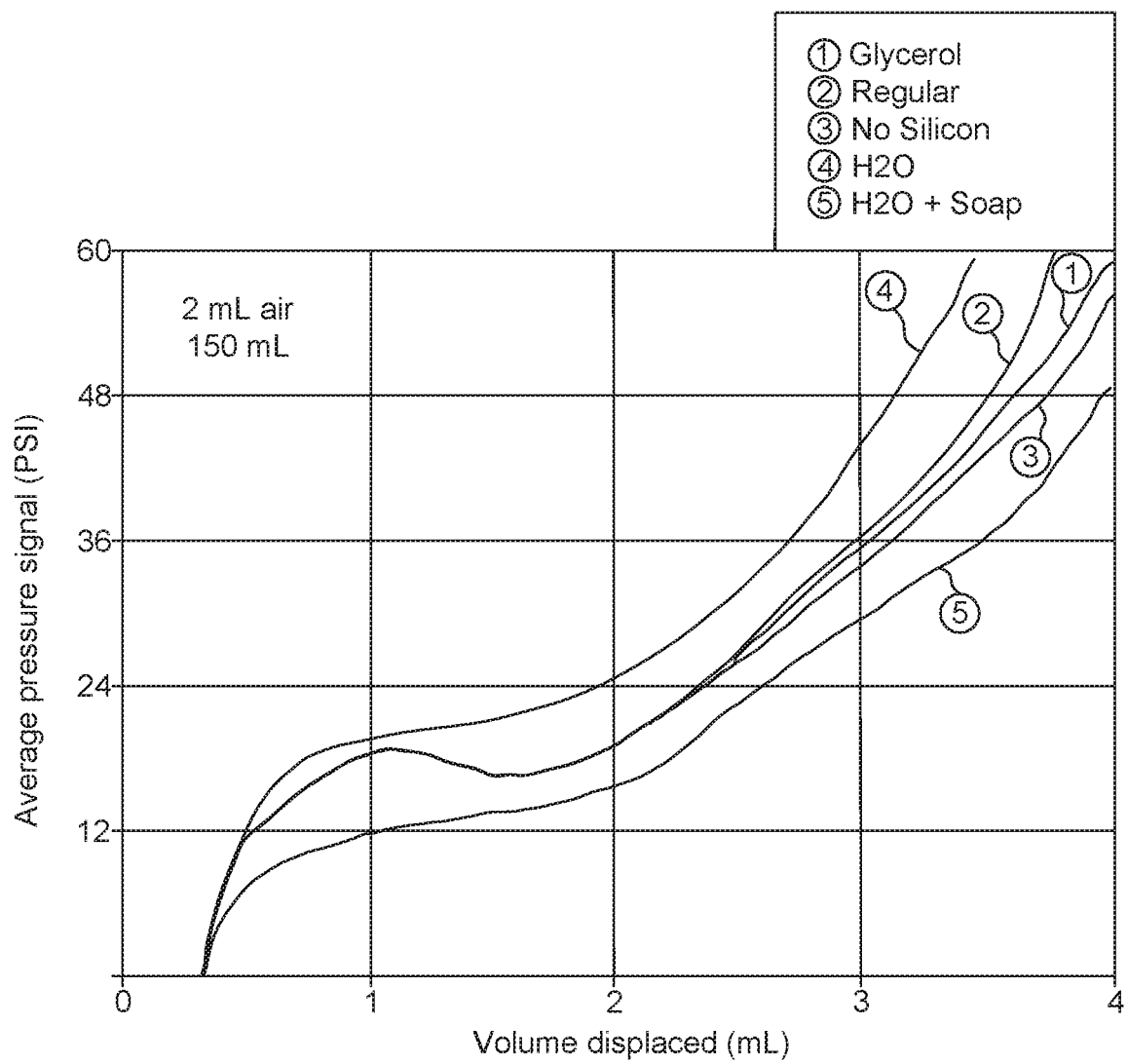
Figure 16D:
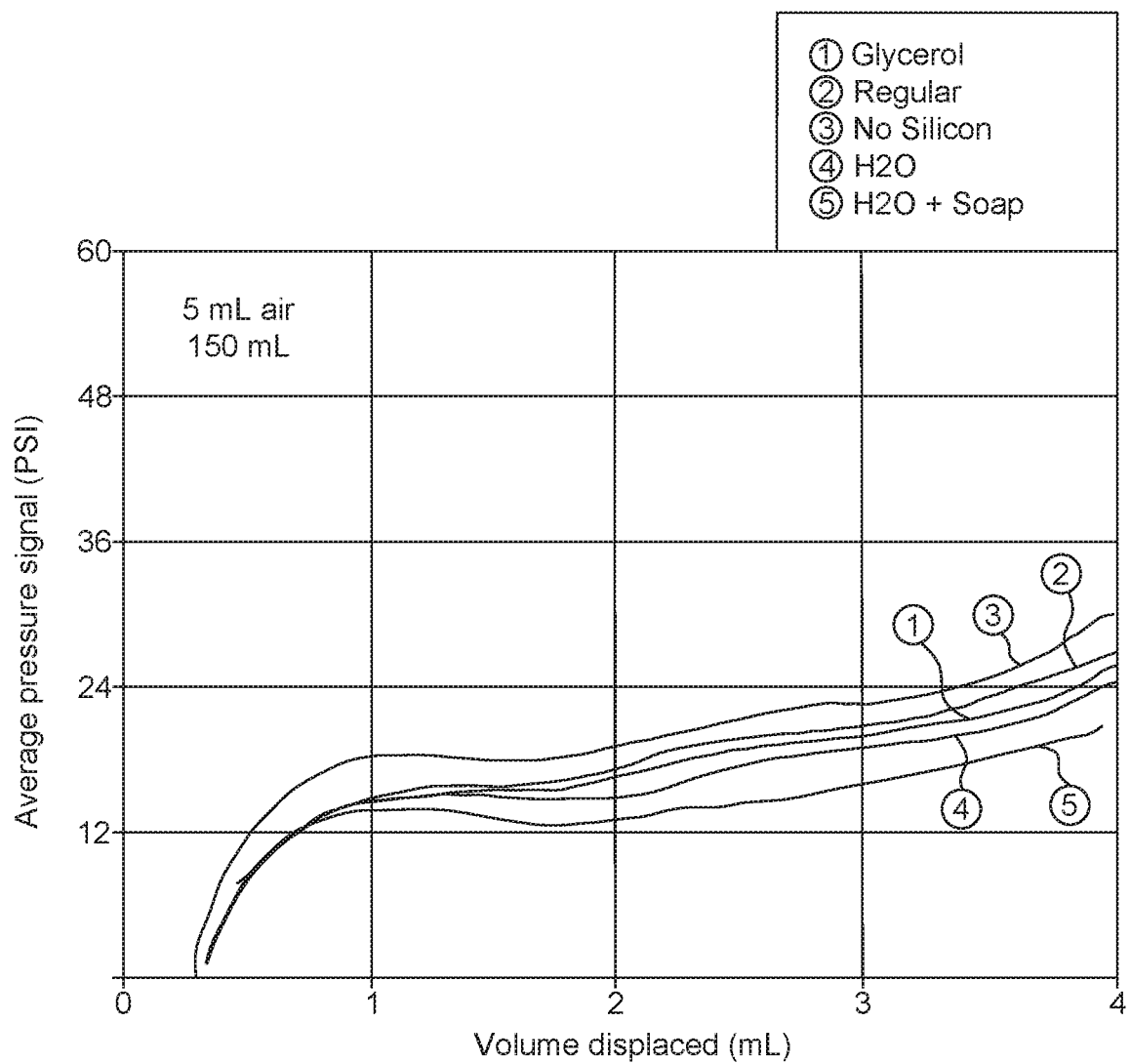

The experimental set-up included an MCT injector with a pressure jacketed 200 mL syringe connected directly to a pressure gauge restriction valve. The syringe was filled with water, the valve was closed, the injector was armed, and the injection was performed at the different test conditions set forth in FIG. 15. Various levels of plunger to barrel friction were created using two different techniques. A pressure jacket and syringes with different types of lubricants, including no silicon, water, soap and water, and glycerol were used. Hose clamps were placed along the length of the pressure jacket and tightened to 5, 7.5, and 10 in-lbs. of torque as measured with a torquemeter. Different amounts of air (0, 1, 2, 5 mL) were added to the syringe using a hand syringe and biopsy needle. Injections were done at 1.0 mL/s for 10 mL with an initial plunger position of 150 mL and 50 mL. The last motion of the plunger was forward for all tests. Data was acquired using a data acquisition system and software developed in-house. The results are reflected in FIGS. 16A-16B.

Figure 17A:
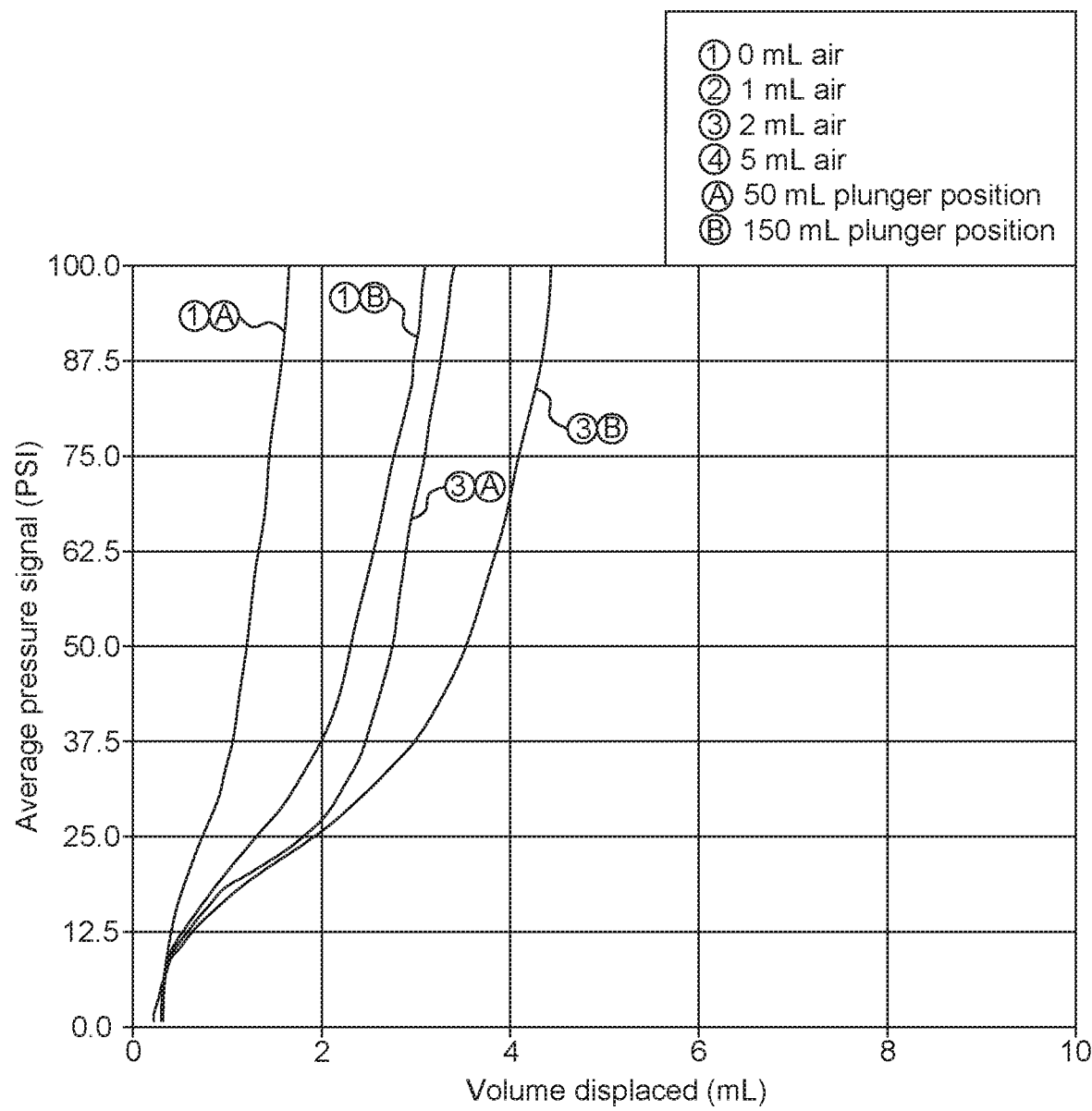
FIGS. 17A-17B illustrate graphs of the average pressure required to dispense the contents of a syringe as a function of the syringe volume displaced.
Figure 17B:
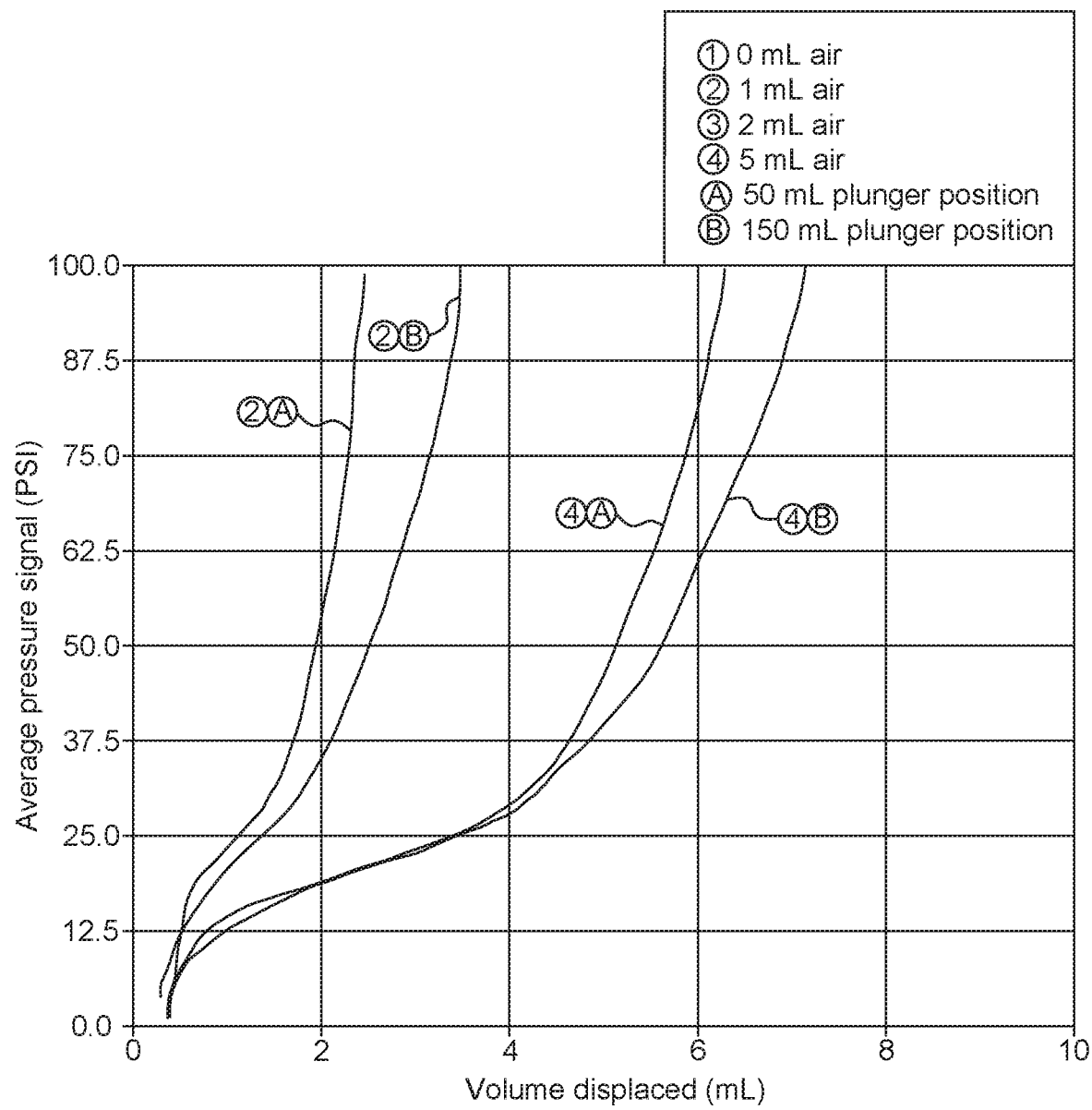

The injector's average pressure signal versus the volume displaced (change in plunger position) was plotted for each test. Averaging was done using a running average, the average of 30 points (0.6 mL) before and including the present measurement. This causes a ramp up at the beginning of the injection and a ramp down during the recoil. Curve fitting and slope calculations were performed on these p-v curves using data from test conditions 1-5. In general, plots of the averaged pressure (psi) versus volume displaced (mL) showed that increasing the amount of air in the syringe results in lower pressures and flatter curves, as evidenced in FIGS. 16A-16B. This was consistent for all tests. The various lubricants produced a range of syringe frictions, with the lower frictions (soap and water) exhibiting flatter curves and lower pressures. In addition, stiffness increased as the initial plunger position moved forward, as evidenced in FIGS. 17A-17B.

A curve fitting algorithm based on the least squares method was written assuming that a function describing the relationship between volume displaced and pressure was:

$$V_{displaced} = A0 + A1[(Pgauge)/(Pabs=Po)] + 1/A3 \, (Pguage),$$

where: A0=volume offset (mL)
A1=nRT, amount of gas (psi-mL)
A2=pressure due to friction (psi)
A3=k, stiffness (psi/mL)
Po=14.7, nominal atmospheric pressure (psi)
Pgauge=Pmotor−A2 (psi)
Pabs=Pgauge+Po (psi)

To find the best fit for this function, the coefficients (A's) were determined by minimizing the sum of the squares of the individual errors:

$$\Sigma[V_i - F(A0, A1, A2, A3, Pmotor]^2$$

Solving for these coefficients gives values for initial volume (A0), amount of air (A1), pressure due to friction (A2), and stiffness (A3). Curve fitting was performed over 7-100 psi.

Initially, a second order term was assumed in the equation. However, it was eliminated since it did not improve the fit and slowed the algorithm. Scatter plots of the fitter parameters versus the amount of air at various levels of syringe friction were done to examine the coefficient variability and trends.

Figure 18A:
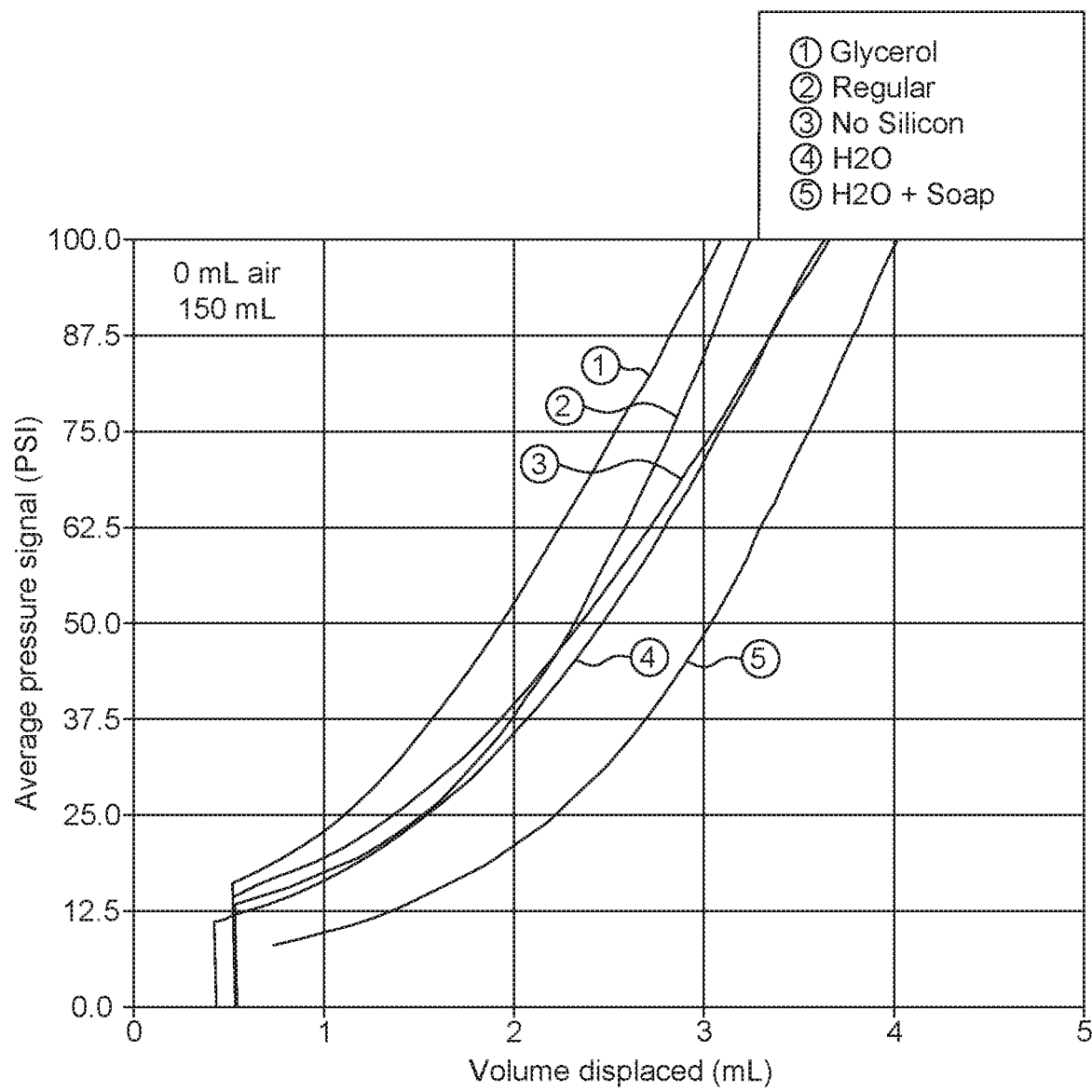
FIG. 18A-18B illustrate a graph of the fit of experimental data to an equation developed using a least squares approach.
Figure 18B:
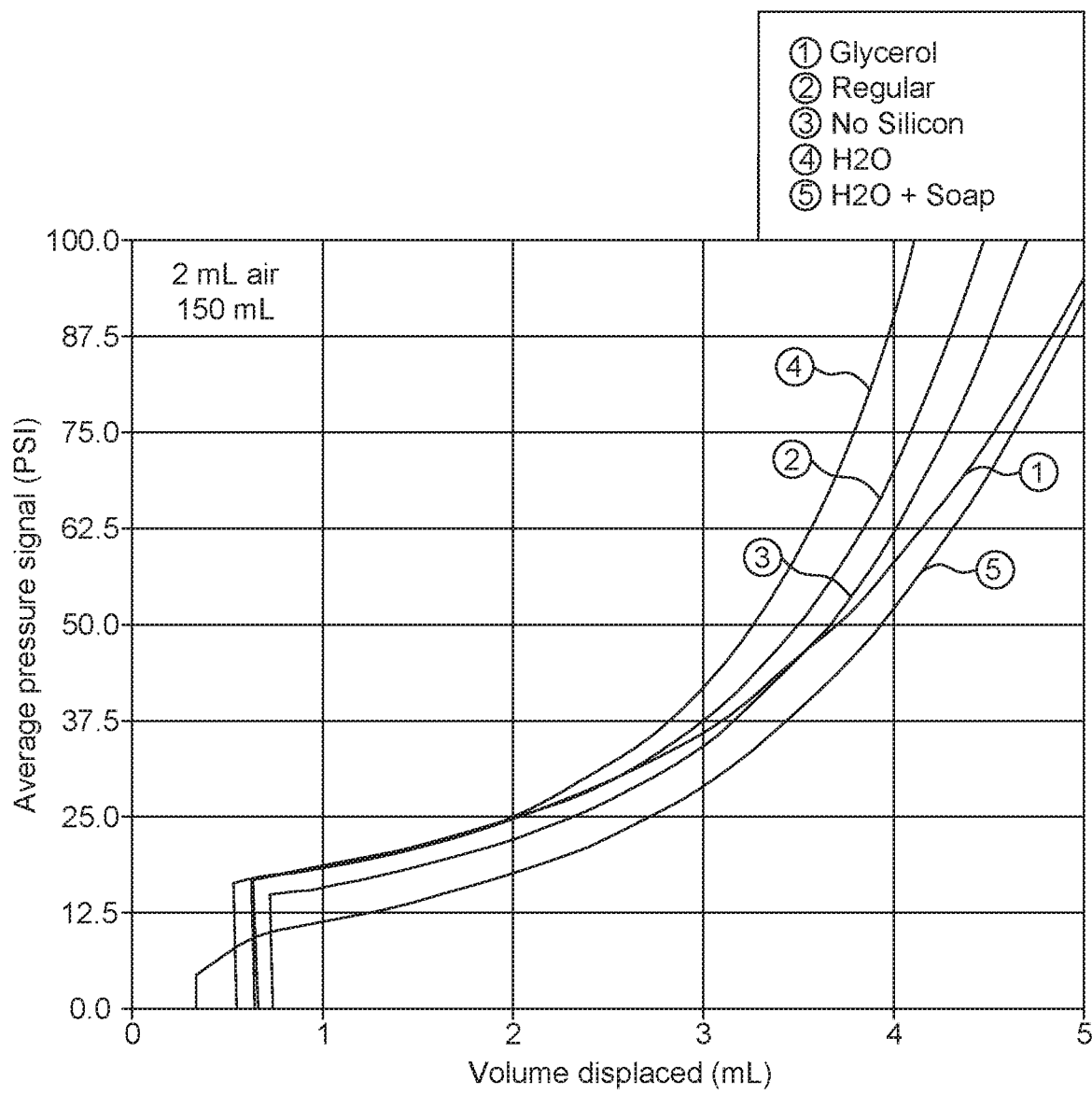
Figure 19A:
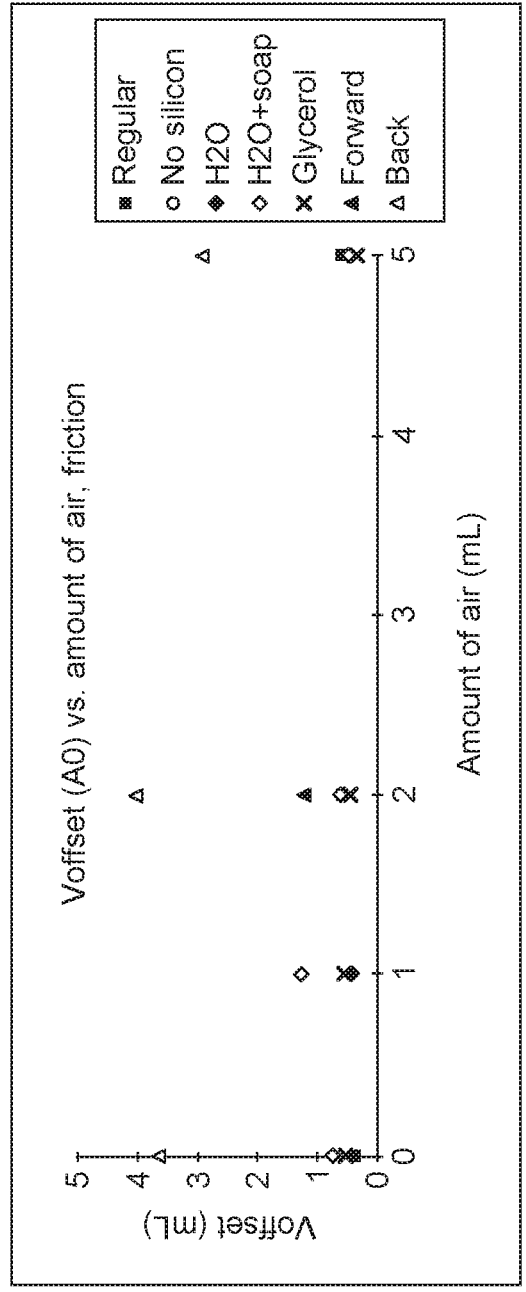
FIG. 19A-19B illustrate scatter plots of the coefficient A0 for different plunger positions.
Figure 19B:
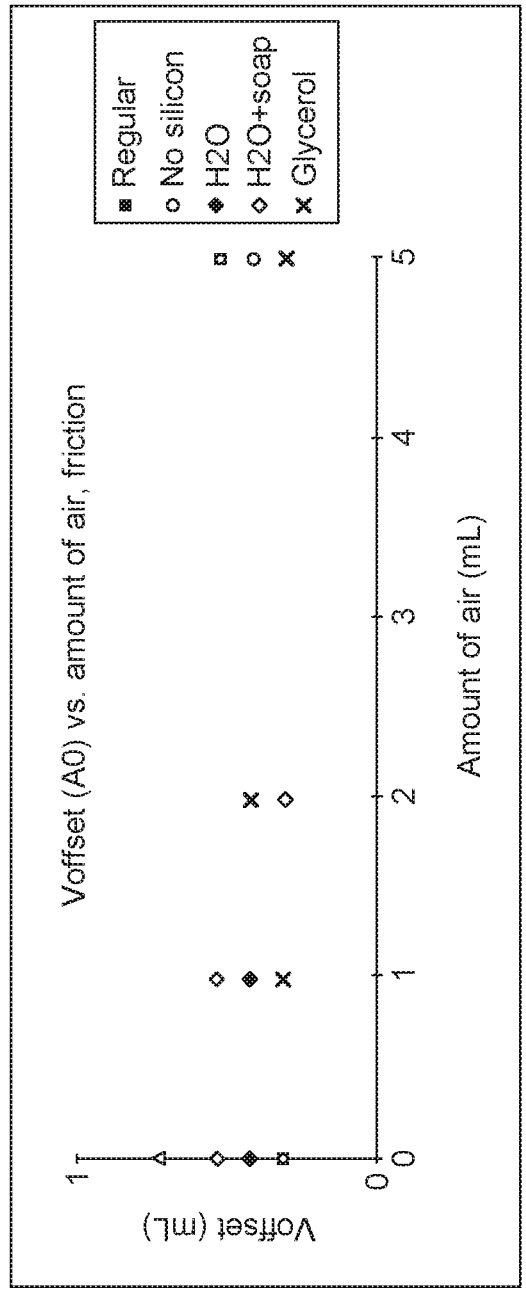
Figure 20A:
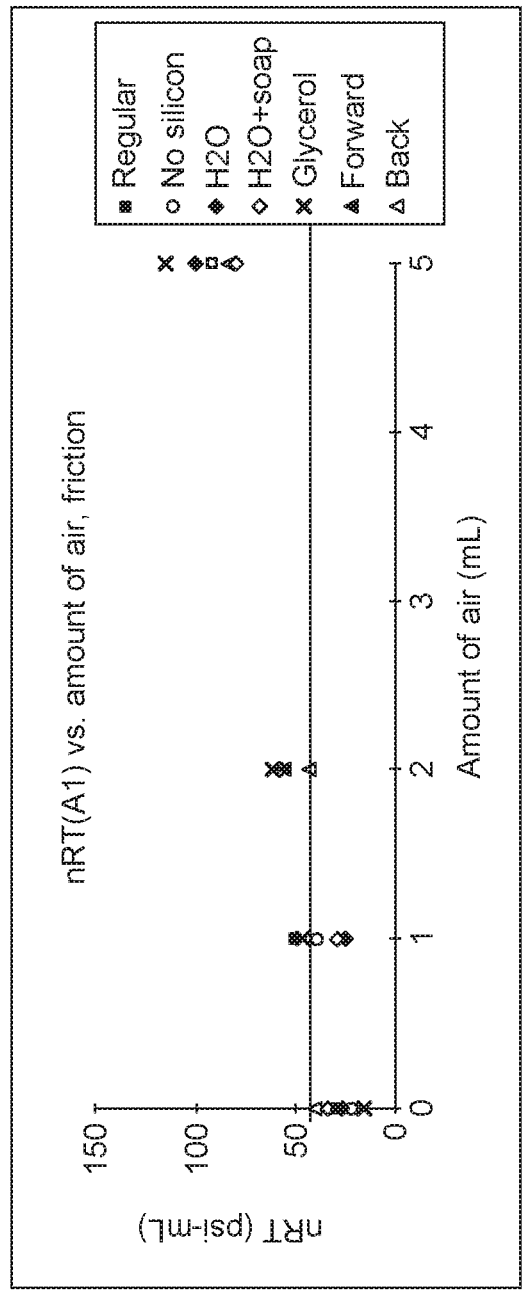
FIG. 20A-20B illustrate scatter plots of the coefficient nRT for different plunger positions.
Figure 20B:
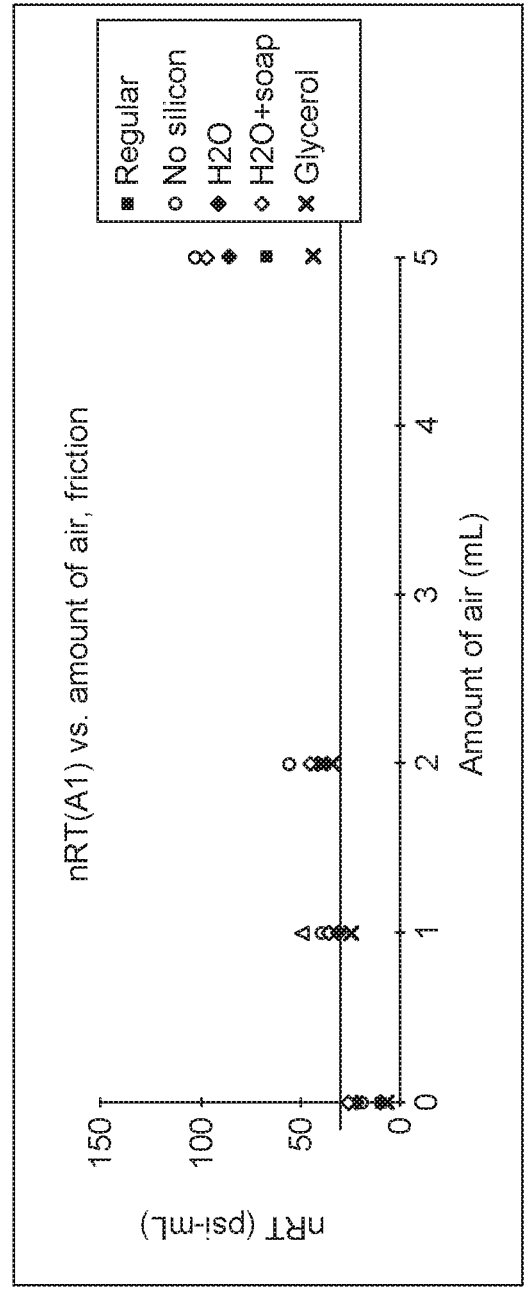

FIGS. 18A-18B show the fit between the equation and the experimental data. A0 (mL) represented the initial volume at time zero. This parameter did not vary with the amount of air in the syringe and changed only slightly with syringe friction, as shown in FIGS. 19A-19B. A1 (psi-mL) represented the amount of air in the syringe. A1 increased with the amount of air, varying slightly with syringe friction. On the scatter plots of FIGS. 20A-20B, it is possible to distinguish between cases with 2 or more mL of air even with different syringe frictions and plunger positions. At plunger position 150 mL, the maximum A1 value at 0 mL of air and the minimum A1 value at 2 mL air were 34.8 and 42.72, respectively. At plunger position 50 mL, these corresponding values for 0 mL air and 2 mL air were 26.16 and 33.36, respectively. Theoretically, at 0 mL of air, A1 should equal zero. However, measured A1 values for 0 mL resemble those for 1-2 mL of air. Possible explanations of this include air under the rubber cover of the plunger or expansion of the syringe under the increased pressure until it is constrained by the pressure jacket.

Figure 21A:
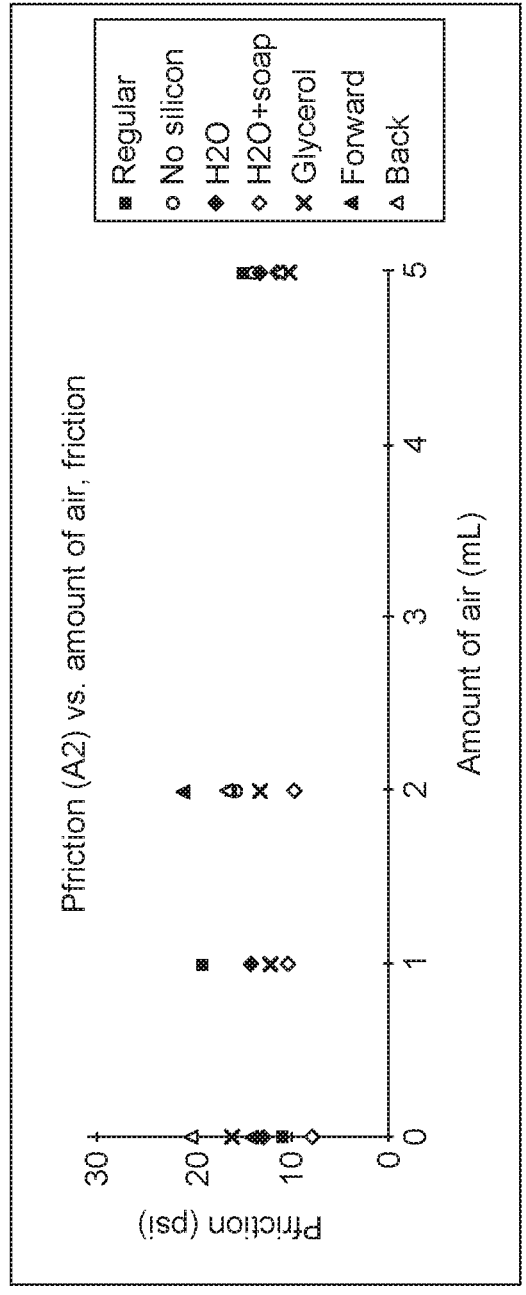
FIG. 21A-21B illustrate scatter plots of the coefficient A2 for different plunger positions.
Figure 21B:
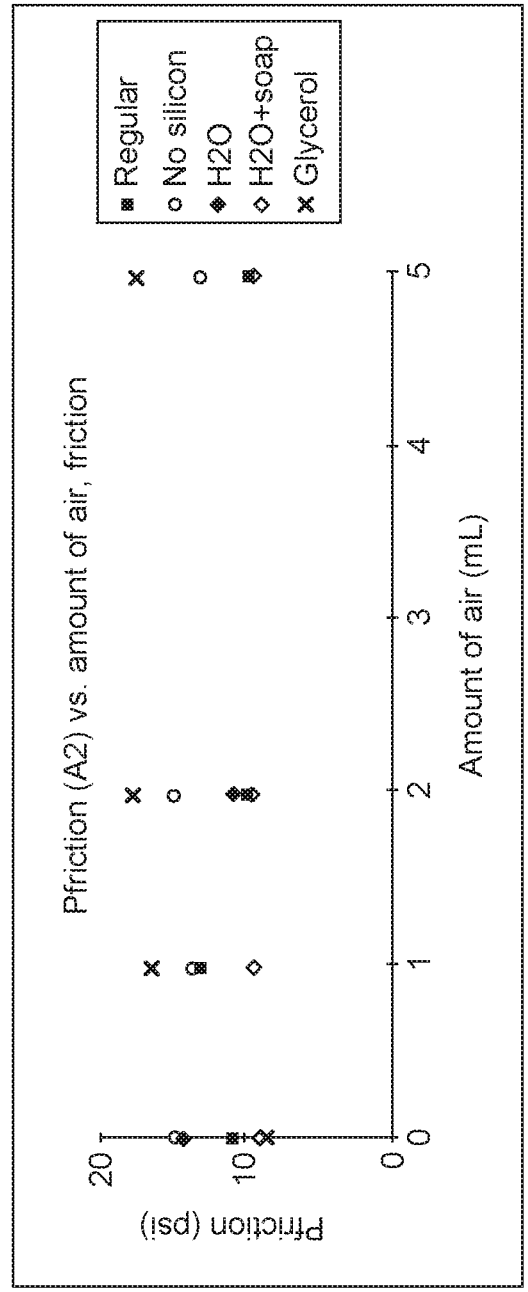
Figure 22A:
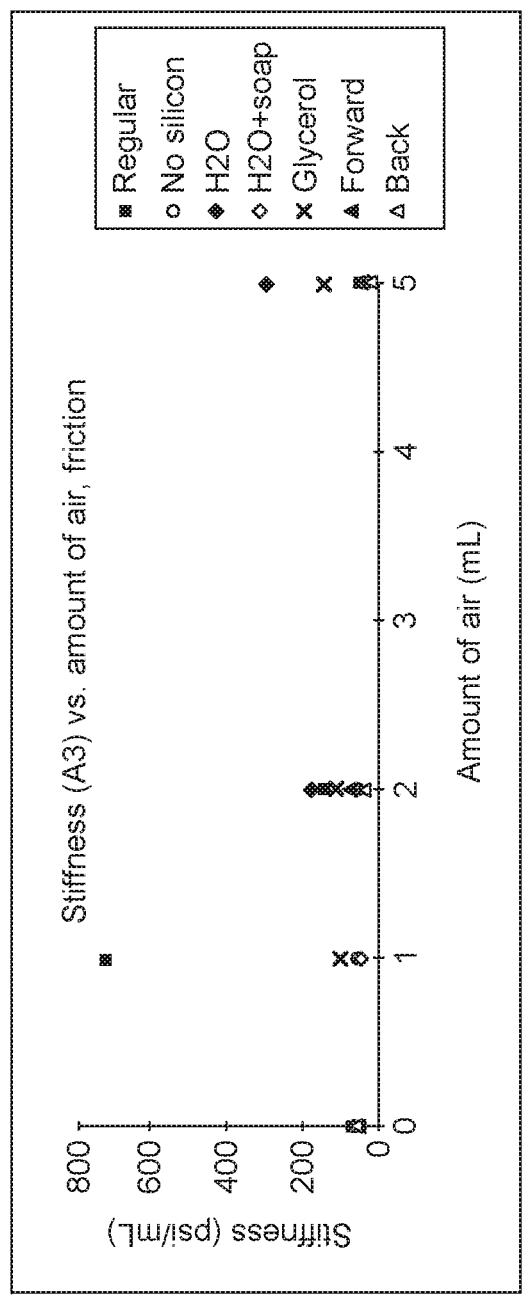
FIG. 22A-22B illustrate scatter plots of the coefficient A3 for different plunger positions.
Figure 22B:
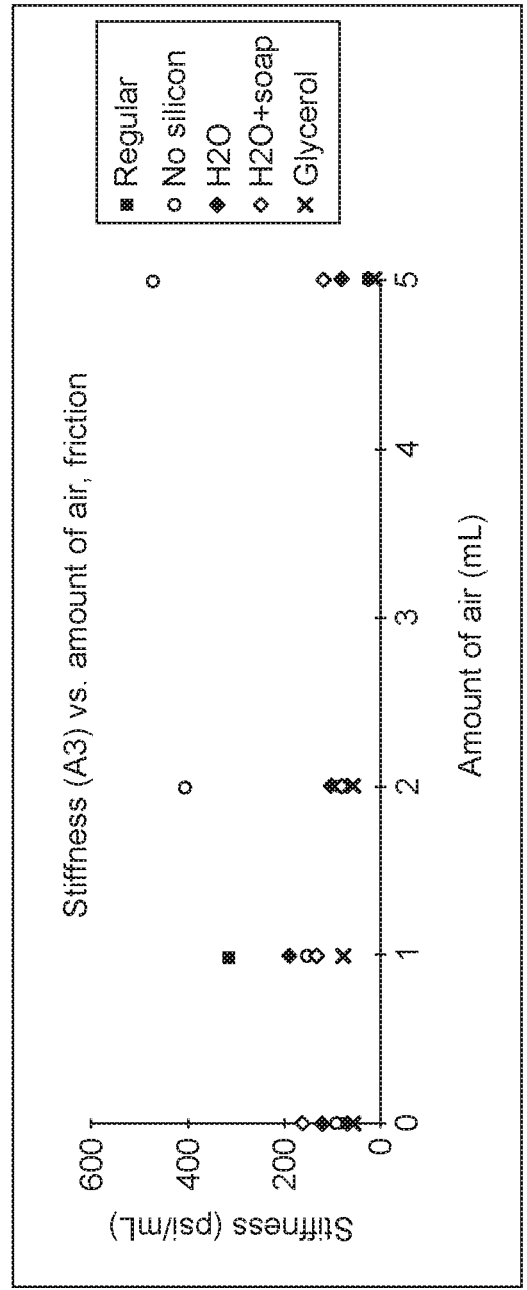

A2 (psi) was the pressure due to friction. On the scatter plot, A2 varied with syringe friction but did not change with the calculated amount of air in the syringe, as shown in FIGS. 21A-21B. A3 (psi/mL) was the stiffness of the system. It was difficult to draw conclusions regarding A3 from the scatter plots, see FIGS. 22A-22B. Scatter increased with the amount of air present in the system. The mean stiffness for the 150 mL and 50 mL plunger positions were 118.61 and 142.09, respectively.

Curve fitting data from previous bench tests was done over 25-100 psi to account for the mechanical slack in the head associated with different injector motions (forward/back). This strategy produced fitted parameters that were consistent with the above results. This indicates that A1 is capable of distinguishing air from other test variables.

As an alternative to curve fitting, the detection algorithm can be based on a slope calculation (mL/psi) of the pressure-volume curve. It is possible that a detection algorithm based on a slope calculation approach will require less processing time, though it may not offer as sensitive of detection as the curve fit approach. The slope calculation approach may serve as a check on the curve fit algorithm and as a more rapid method to determine if large amounts of air are present. A non-limiting example of the manner in which such a slope calculation algorithm can be developed follows.

Figure 23A:
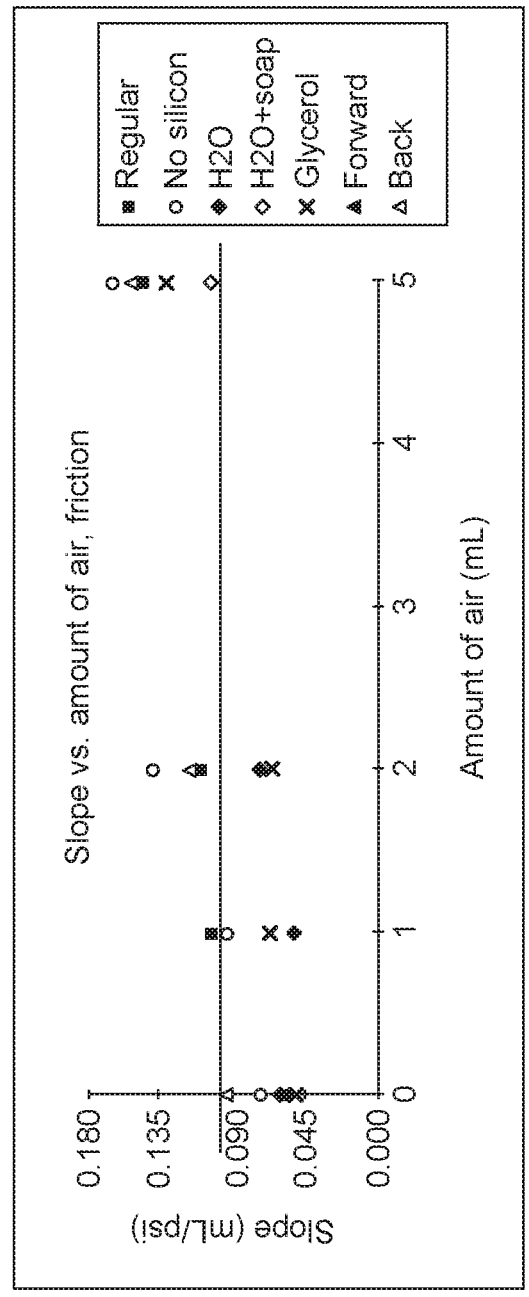
FIG. 23A-23B illustrate scatter plots of the slope versus the amount of air for different plunger positions.
Figure 23B:
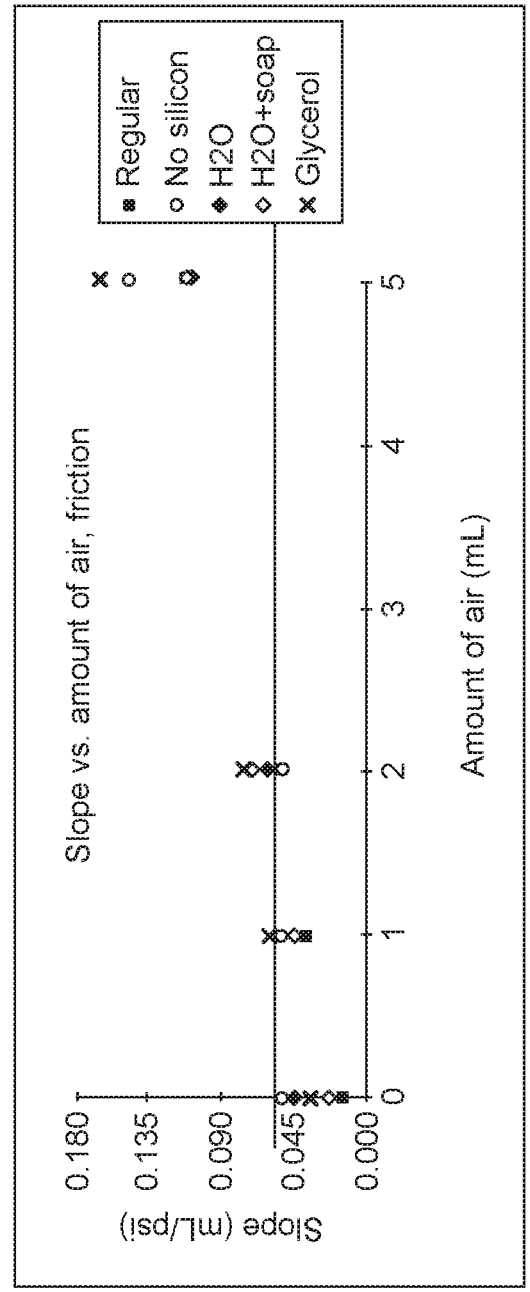

Slope calculations were performed on the p-v curves mentioned above. Slope was calculated between pressure values of 20 and 35 psi. This region was selected over several other regions (20-50 psi, 20-45 psi) because it was believed to be easier to observe data trends in the smaller region. Scatter plots of slope versus the amount of air at various syringe frictions were done to examine variability and trends, FIGS. 23A-23B. It was observed that slope was independent of operator manipulation and that the slope increased with increasing air. There was observed a threshold at about 0.095 mL/psi which differentiates the cases with 2 mL of air or more from the cases with 0 mL of air, as shown in the plot of FIG. 23A. This threshold was observed to be too high for cases where the starting plunger position is at the 50 mL position, as shown in the plot of FIG. 23B. For these cases, the threshold could be 0.060 mL/psi. Even so, fixing the threshold at 0.095 mL/psi differentiates the condition with 5 mL of air from 0 mL for both plunger positions.

Irrespective of the detection algorithm used, signals representing volume and pressure can be input to the processing unit 401. Volume signals can be represented by the piston plunger position. For example, piston plunger position can range from 0 to 10 V with a scale factor of 61.1 mV/mL for a 150 mL syringe. Pressure signal represents the pressure within the syringe. For example, the signal can range from 0 to 7.5 V with a scale factor of 6.25 mV/psi for a 150 mL syringe. Data can be sampled at intervals like those discussed herein, such as at a rate of about 50 samples per second with approximately 100 μsec sample intervals. Low pass anti-aliasing filters can be used with the input signals. Programmable gain amplifiers and/or programmable offsets may be included as well so that the input signal range and gain may be scaled for greater resolution. Alternatively, digital filtering or other processing may be used. From the results discussed herein, if it is desired to only detect relatively large amounts or volumes of air, algorithms with relatively simple or fixed adjustments may be used. If it is desired to detect smaller quantities of air, the algorithm may be more sophisticated, for example to take into account one or more of plunger position in the syringe, whether the last motion was forward (distal) or reverse (proximal), frictional characteristics of the syringe, flow rate, pressure, and capacitance of various fluid path elements. In certain embodiments, the algorithm may also or alternatively include a precalculated expectation path or curve based upon any of the factors expected to affect the curve, with the alarm being initiated if the actual pressure signal deviates from the curve by a predetermined amount.

Figure 24:
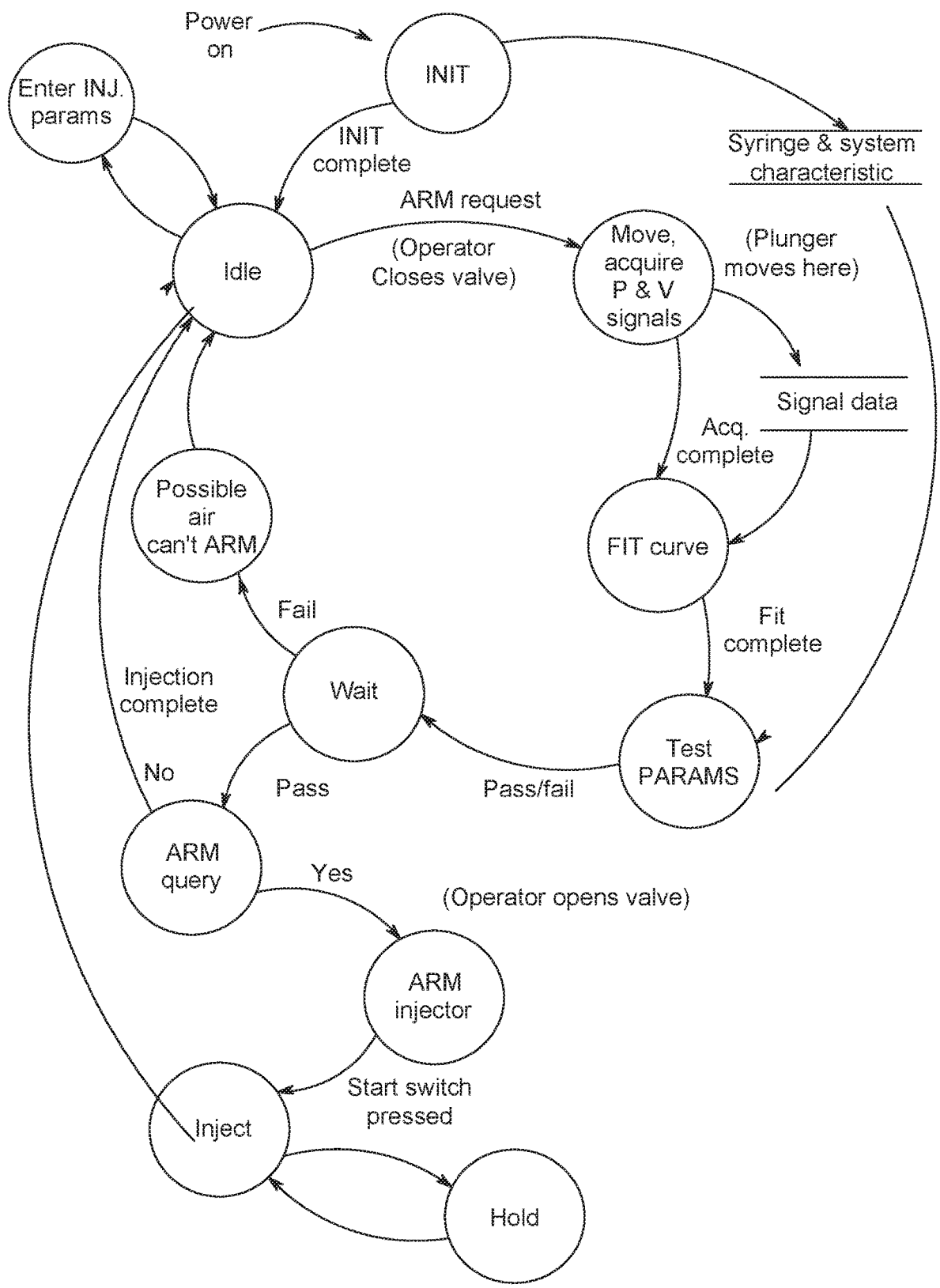
FIG. 24 illustrates a flow diagram of the operation of the fluid output verification mechanism according to one embodiment.

With reference to FIG. 24, a general description of this operation is provided. The detection algorithm can be coded to execute after signal data is collected when the operator initiates a request to "arm" the injector. The initialization process can include obtaining information about the syringe 14, 14*a*, 14*b*, and/or 114 and syringe characteristics from, for example, a database in communication with the processing unit 401 and/or from the injector. Information about the air threshold can also be obtained, for example from memory associated with the injector or from the user. According to an aspect, movement of the syringe 14, 14*a*, 14*b*, and/or 114 forces fluid against inline valve 1701 while inline valve 1701 remains closed, allowing for pressure to build against inline valve 1701. During this process, pressure and volume signals and measurements are received by processing unit 401. The detection algorithm can be applied using this information as well as information about the syringe 14, 14*a*, 14*b*, 114 and syringe characteristics described herein. If the fitted parameters and/or slope calculation indicate that the air volume exceeds a predefined threshold value for the particular syringe size and configuration, the operator can be alerted through an alarm function. If the threshold value is exceeded, the injector can be prevented from injecting and may return to idle state until the issue is corrected and a repeated measurement/calculation process is performed and indicates that the air volume is below the threshold value.

In the event of low volume injections, the additional volume it takes to inflate the syringe 114 at the valve opening pressure may not be delivered. To address this, the inflation volume can be excluded from the calculation of the injected volume.

Like with previously-described embodiments, this embodiment may have associated with it a processing unit programmed with a set of computer-readable operating instructions, one or more databases and/or memories housing information about the expected pressure rise or pressure versus time values for various system components and injection fluids, and an alarm unit programmed to alert an operator of any discrepancies between the measured and the expected pressure values as this would be indicative of the presence of air within the fluid path. Similarly, as described above with other embodiments, pressure measurements can be taken continuously or periodically during the relevant time periods.

Although the disclosure has been described in detail for the purpose of illustration, a flow restriction may include any fluid path element that controllably restricts flow, for example a narrowed section of fluid path, a filter, a valve with a higher than normal opening pressure, a valve with a specified crack pressure, for example as described in WO 2014/144651, a manually or automatically operated on/off valve, stopcock, or pinch valve. Further, assessment of fluid accuracy, suitability, and absence of air or gas above a suitable threshold may be made during one or more of a fill, delivery, and/or any other fluid motion stage of an overall fluid handling and delivery process.

Although the disclosure has been described in detail for the purpose of illustration based on what is currently considered to be the most practical and preferred embodiments, it is to be understood that such detail is solely for that purpose and that the disclosure is not limited to the disclosed embodiments, but, on the contrary, is intended to cover modifications and equivalent arrangements. For example, it is to be understood that the present disclosure contemplates that, to the extent possible, one or more features of any embodiment can be combined with one or more features of any other embodiment.

We claim:

1. A fluid delivery system, comprising:
   a syringe;
   a fluid injector comprising a drive shaft for drawing fluid into and dispensing fluid from the syringe;
   one or more strain sensors adapted to measure a force applied by the drive shaft to draw the fluid into the syringe;
   a processor in communication with the one or more strain sensors; and
   a non-transitory, computer-readable storage medium in operable communication with the processor,
   wherein the computer-readable storage medium contains one or more programming instructions that, when executed, cause the processor to receive from the one or more strain sensors one or more measurements of the force applied by the drive shaft to draw the fluid into the syringe during an onset period and after a steady state for the force applied to the drive shaft is reached and determine from the one or more measurements of the force applied by the drive shaft to draw the fluid into the syringe whether air is present in the syringe by a slope of a force applied by the drive shaft compared to a time for the onset period and whether a correct fluid is being drawn into the syringe by comparison with a predetermined steady state force value P for the correct fluid.

2. The system of claim 1, wherein the one or more programming instructions, when executed, cause the processor to determine from the one or more measurements of the force applied by the drive shaft to draw the fluid into the syringe whether air is present in the syringe by comparing at least one of the one or more measurements of the force applied by the drive shaft compared to the time to draw the fluid into the syringe during the onset period where the slope is less than when air is not present in the syringe during the onset time.

3. The system of claim 2, wherein the one or more programming instructions, when executed, cause the processor to trigger an alarm if at least one of the one or more measurements of the force applied by the drive shaft to draw the fluid into the syringe is sufficiently different than the predetermined steady state force value or when the slope of the force compared to time during the onset period indicates the presence of air in the syringe.

4. The system of claim 2, wherein the one or more programming instructions, when executed, cause the processor to stop operation of the fluid injector if at least one of the one or more measurements of the force applied by the drive shaft to draw the fluid into the syringe is sufficiently different than the predetermined steady state force value or when the slope of the force compared to time during the onset period indicates the presence of air in the syringe.

5. The system of claim 1, further comprising wherein the one or more strain sensors are adapted to measure a force applied by the drive shaft to dispense the fluid from the syringe, and wherein the one or more programming instructions, when executed, cause the processor to receive one or more measurements of the force applied by the drive shaft to dispense the fluid from the syringe and determine from the one or more measurements of the force applied by the drive shaft to dispense the fluid from the syringe whether the correct fluid is being dispensed from the syringe.

6. A method of verifying a content of a syringe in a fluid delivery system, comprising:
   drawing a fluid into the syringe by an injector comprising a drive shaft;
   obtaining, using one or more strain sensors, one or more measurements of a force applied by the drive shaft to draw the fluid into the syringe during an onset period and after a steady state for the force applied to the drive shaft is reached; and
   determining, from the one or more measurements of the force applied by the drive shaft to draw the fluid into the syringe, whether air is present in the syringe by a slope of a force applied by the drive shaft compared to a time for the onset period and whether the fluid is a correct fluid by comparison with a predetermined steady state force value P for the correct fluid.

7. The method of claim 6, wherein determining from the one or more measurements of the force applied by the drive shaft to draw the fluid into the syringe whether air is present in the syringe comprises comparing at least one of the one or more measurements of the force applied by the drive shaft compared to the time to draw the fluid into the syringe during the onset period where the slope is less than when air is not present in the syringe during the onset time.

8. The method of claim 7, further comprising receiving the predetermined steady state force value from a user interface associated with the fluid delivery system or from a database associated with the fluid delivery system.

9. The method of claim 6, further comprising triggering an alarm if it is determined that air is present in the syringe or the fluid is not the correct fluid.

* * * * *

UNITED STATES PATENT AND TRADEMARK OFFICE
CERTIFICATE OF CORRECTION

PATENT NO. : 12,263,326 B2
APPLICATION NO. : 16/349314
DATED : April 1, 2025
INVENTOR(S) : Uber, III et al.

Page 1 of 1

It is certified that error appears in the above-identified patent and that said Letters Patent is hereby corrected as shown below:

In the Specification

In Column 1, Line 12, delete "is" and insert -- are --, therefor.
In Column 7, Line 47, delete "FIG." and insert -- FIGS. --, therefor.
In Column 7, Line 50, delete "FIG." and insert -- FIGS. --, therefor.
In Column 7, Line 52, delete "FIG." and insert -- FIGS. --, therefor.
In Column 7, Line 54, delete "FIG." and insert -- FIGS. --, therefor.
In Column 7, Line 56, delete "FIG." and insert -- FIGS. --, therefor.
In Column 7, Line 58, delete "FIG." and insert -- FIGS. --, therefor.
In Column 11, Line 8, delete "measurements of" and insert -- measure --, therefor.
In Column 11, Line 65, delete "idea gas law" and insert -- ideal gas law --, therefor.
In Column 13, Line 65, delete "will" and insert -- will be --, therefor.
In Column 15, Line 33, delete "fill" and insert -- filling --, therefor.
In Column 15, Line 37, delete "pressure" and insert -- pressure of --, therefor.
In Column 17, Line 31, delete "in the" and insert -- and the --, therefor.
In Column 20, Line 1, delete "though" and insert -- through --, therefor.
In Column 20, Line 44, delete "gage" and insert -- gauge --, therefor.
In Column 24, Line 14, delete "in-lbs. of" and insert -- in-lbs of --, therefor.
In Column 24, Lines 44-45, delete "$V_{displaced}=A0+A1[(Pgauge)/(Pabs=Po)]+1/A3(Pguage),$" and insert -- $V_{displaced}=A0+A1[(Pgauge)/(Pabs \cdot Po)]+1/A3(Pguage)$, --, therefor.
In Column 24, Line 56, delete "$\Sigma[V_i-F(A0,A1,A2,A3,Pmotor]^2$" and insert -- $\Sigma[V_i-F(A0,A1, A2, A3, Pmotor)]^2$ --, therefor.
In Column 25, Line 12, delete "mL air" and insert -- mL of air --, therefor.

Signed and Sealed this
Third Day of June, 2025

Coke Morgan Stewart
*Acting Director of the United States Patent and Trademark Office*